(12) United States Patent
Dal Piaz et al.

(10) Patent No.: US 7,459,453 B2
(45) Date of Patent: Dec. 2, 2008

(54) PYRIDAZIN-3(2H)-ONE DERIVATIVES AS PDE4 INHIBITORS

(75) Inventors: Vittorio Dal Piaz, Impruneta (IT);
Maria Paola Giovannoni, Scandicci (IT); Claudia Vergelli, Florence (IT); Nuria Aguilar Izquierdo, Barcelona (ES)

(73) Assignee: Laboratorios Almirall, S.A. (ES)

( * ) Notice: Subject to any disclaimer, the term of this patent is extended or adjusted under 35 U.S.C. 154(b) by 143 days.

(21) Appl. No.: 10/513,219

(22) PCT Filed: May 14, 2003

(86) PCT No.: PCT/EP03/05056

§ 371 (c)(1),
(2), (4) Date: Jun. 29, 2005

(87) PCT Pub. No.: WO03/097613

PCT Pub. Date: Nov. 27, 2003

(65) Prior Publication Data

US 2006/0052379 A1   Mar. 9, 2006

(30) Foreign Application Priority Data

May 16, 2002   (ES) ............................... 200201111

(51) Int. Cl.
*A61K 31/501* (2006.01)
*C07D 401/04* (2006.01)
*C07D 403/04* (2006.01)
*C07D 405/04* (2006.01)
*C07D 409/04* (2006.01)
*C07D 237/10* (2006.01)
*A61P 17/00* (2006.01)

(52) U.S. Cl. ............. 514/247; 514/252.01; 514/252.03; 544/238; 544/239

(58) Field of Classification Search ................ 544/238, 544/239; 514/247, 252.01, 252.03
See application file for complete search history.

(56) References Cited

U.S. PATENT DOCUMENTS

| 5,804,588 | A | 9/1998 | Dyke et al. |
| 5,859,008 | A | 1/1999 | Jonas et al. |
| 5,972,936 | A | 10/1999 | Dyke et al. |
| 6,162,830 | A | 12/2000 | Connor et al. |
| 6,204,275 | B1 | 3/2001 | Friesen et al. |
| 6,699,890 | B2 | 3/2004 | Schumacher et al. |

FOREIGN PATENT DOCUMENTS

| SU | 405344 T | 8/1975 |
| WO | WO93/07146 A1 | 4/1993 |
| WO | WO01/94319 A1 | 12/2001 |

OTHER PUBLICATIONS

Lipworth, Lancet 2005, 365: 167-75.*
MacKenzie, Phosphodiesterase 4 cAMP phosphodiesterases as targets for novel anti-inflammatory therapeutics, Alergology International (2004) 53: 101-110.*
Griffiths, et al., British J. of Dermatology 2002: 147, 299-307.*
Wikipedia, Phosphodiesterase, <http://en.wikipediaa.org/wiki/Phosphodoesterase>, downloaded May 31, 2007.*
Wikipedia, COPD, <http://en.wikipedia.org/wiki/COPD>, downloaded May 30, 2007.*
Wikipedia,Inflammatory Bowel Disease, <http://en.wikipedia.org/wiki/IBD>, downloaded May 31, 2007.*
Spina, Drugs, 2003, 63, 23, pp. 2575-2594.*
Baumer, et al., Inflammation & Allergy—Drug Targets, vol. 6, No. 1, Mar. 2007.*
Implications for Rheumatoid Arthritis http://www.medscape.com/viewarticle/464104_4, downloaded Jul. 8, 2007.*
Phosphodiesterases: A Drug Target Family with Broad Therapeutic Impact, http://www.piribo.com/publications/drug_discovery/DMD054.html, downloaded Jul. 9, 2007.*
Dr. Andrew R. Marks, Columbia University Medical Center press release, Drugs in Trials for Asthma, Alzheimer's and Chronic Lung Disease May Cause Heart Disease, < http://www.cumc.columbia.edu/news/press_releases/Marks_Cell.html>, downloaded Jul. 9, 2007.*
Vittorio Dal Piaz et al.; J. of Pharmaceutical Sciences, 1991, V.80, N.4, pp. 341-348.
Luca Costantino et al.; J. Med. Chem., 1999, N.42, pp. 1894-1900.
Giovanna Ciciani et al.; Il Farmaco, 1991, V.46. N.7-8, pp. 873-885.
Daniela Barlocco et al.; J. Med. Chem., 2001, N.44, pp. 2403-2410.
Vittorio Dal Piaz et al.; Eur. J. Med. Chem.; 1996, N.31, pp. 65-70.
Margaretha Van Der Mey et al.; J. Med, Chem.; 2001, N. 44, pp. 2511-2522.
CAPLUS abstract for SU 405344, accession No. 1976:4988 dated May 12, 1984.

(Continued)

*Primary Examiner*—Mark L. Berch
*Assistant Examiner*—Cecilia M Jaisle
(74) *Attorney, Agent, or Firm*—Finnegan, Henderson, Farabow, Garrett & Dunner, LLP

(57) ABSTRACT

New pyridazin-3(2H)-one derivatives having the chemical structure of general formula (I) are disclosed; as well as process for their preparation, pharmaceutical compositions comprising them and their use in therapy as inhibitors of phosphodiesterase 4.

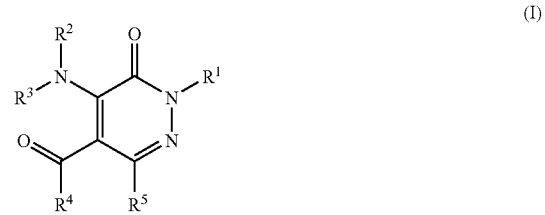

9 Claims, No Drawings

OTHER PUBLICATIONS

Essayan, David M., "Cyclic nucleotide phosphodiesterase (PDE) inhibitors and immunomodulation," Biochemical Pharmacology, 57:965-973 (1999).

Nyman, U., et al., "Amelioration of collagen II-induced arthritis in rats by the type IV phosphodiesterase inhibitor rolipram," Clin. Exp. Immunol, 108:415-419 (1997).

Gilhar, A., et al., "Antiproliferative effect of pentoxifylline on psoriatic and normal epidermis," Acta Derm Venereol, 76:437-441 (1996).

Hanifin, Jon M., et al., "Type 4 phosphodiesterase inhibitors have clinical and in vivo anti-inflammatory effects in atopic dermatitis," Journal of Investigative Dermatology, 107(1):51-56 (1996).

Diaz-Granados, Natalia et al., "Dextran sulfate sodium-induced colonic histopathology, but not altered epithelial ion transport, is reduced by inhibition of phosphodiesterase activity," American Journal of Pathology, 156(6):2169-2177 (2000).

Dyke, Hazel J., et al., "The therapeutic potential of PDE4 inhibitors," Exp. Opin. Invest. Drugs, 8(9):1301-1325 (1999).

Hartmann, Gunther et al., "Specific type IV phosphodiesterase inhibitor rolipram mitigates experimental colitis in mice," Journal of Pharmacology and Experimental Therapeutics, 292(1):22-30 (2000).

Stawiski, Marek A., et al., "Ro 20-1724: an agent that significantly improves psoriatic lesions in double-blind clinical trials," The Journal of Investigative Dermatology, 73(4):261-263 (1979).

Teixeira, Mauro M., et al., "Phosphodiesterase (PDE)4 inhibitors: anti-inflammatory drugs of the future?," TiPS, 18:164-170 (1997).

Ross, Susan E., et al., "Suppression of TNF-α expression, inhibition of Th1 activity, and amerlioration of collagen-induced arthritis by rolipram," Journal of Immunology, pp. 6253-6259 (1997).

Sekut, L., et al., "Anti-inflammatory activity of phosphodiesterase (PDE)-IV inhibitors in acute and chronic models of inflammation," Clin. Exp. Immunol, 100:126-132 (1995).

Nicholson, C. David, et al., "Differential modulation of tissue function and therapeutic potential of selective inhibitors of cyclic nucleotide phosphodiesterase isoenzymes," TiPS, 12:19-27 (1991).

Solomons, T. W. G., Organic Chemistry, John Wiley & Sons, Inc., pp. 463-468, 485-486 (1978).

* cited by examiner

PYRIDAZIN-3(2H)-ONE DERIVATIVES AS PDE4 INHIBITORS

This application is a national stage filing under 35 U.S.C. § 371 of International Application No. PCT/EP03/05056, filed on May 14, 2003. This application claims the benefit of priority under 35 U.S.C. § 119 to Spanish Patent Application No. P200201111 filed on May 16, 2002.

This invention relates to new pyridazin-3(2H)-one derivatives, to processes for their preparation and to pharmaceutical compositions containing them. These compounds are potent and selective inhibitors of phosphodiesterase 4 (PDE4) and are thus useful in the treatment, prevention or suppression of pathological conditions, diseases and disorders known to be susceptible of being improved by inhibition of PDE4.

Phosphodiesterases (PDES) comprise a superfamily of enzymes responsible for the hydrolysis and inactivation of the second messengers cyclic adenosine monophosphate. (CAMP) and cyclic guanosine monophosphate (cGMP). Eleven different PDE families have been identified to date (PDE1 to PDE11) which differ in substrate preference, catalytic activity, sensitivity to endogenous activators and inhibitors, and encoding genes.

The PDE4 isoenzyme family exhibits a high affinity for cyclic AMP but has weak affinity for cyclic GMP. Increased cyclic AMP levels caused by. PDE4 inhibition are associated with the suppression of cell activation in a wide range of inflammatory and immune cells, including lymphocytes, macrophages, basophils, neutrophils, and eosinophils. Moreover, PDE4 inhibition decreases the release of the cytokine Tumor Necrosis Factor α (TNFα). The biology of PDE4 is described in several recent reviews, for example M. D. Houslay, *Prog. Nucleic Acid Res. Mol. Biol.* 2001, 69, 249-315; J. E. Souness et al. *Immunopharmacol.* 2000 47,127-162; or M. Conti and S. L. Jin, *Prog. Nucleic Acid Res. Mol. Biol.* 1999, 63,1-38.

In view of these physiological effects, PDE4 inhibitors of varied chemical structures have been recently disclosed for the treatment or prevention of chronic and acute inflammatory diseases and of other pathological conditions, diseases and disorders known to be susceptible to amelioration by inhibition of PDE4. See, for example, U.S. Pat. No. 5,449,686, U.S. Pat. No. 5,710,170, WO 98/45268, WO 99/06404, WO 01/57025, WO 01/57036, WO 01/46184, WO 97/05105, WO 96/40636, U.S. Pat. No. 5,786,354, U.S. Pat. No. 5,773,467, U.S. Pat. No. 5,753,666, U.S. Pat. No. 5,728,712, U.S. Pat. No. 5,693,659, U.S. Pat. No. 5,679,696, U.S. Pat. No. 5,596,013, U.S. Pat. No. 5,541,219, U.S. Pat. No. 5,508,300, U.S. Pat. No. 5,502,072 or H. J. Dyke and J. G. Montana, *Exp. Opin. Invest Drugs* 1999, 8, 1301-1325.

We have now found that a novel series of pyridazin-3(2H)-one derivatives are potent and selective inhibitors of PDE4 and are therefore useful in the treatment or prevention of these pathological conditions, diseases and disorders, in particular asthma, chronic obstructive pulmonary disease, rheumatoid arthritis, atopic dermatitis, psoriasis or irritable bowel disease.

Accordingly, the present invention provides novel compounds of formula (I)

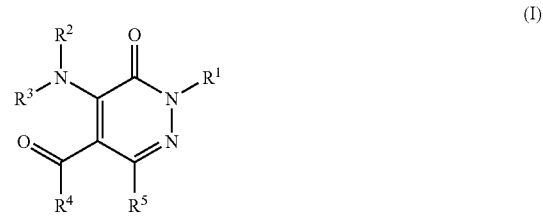

wherein
$R^1$ represents:
  a hydrogen atom;
  a group selected from acyl, alkoxycarbonyl, carbamoyl, monoalkylcarbamoyl or dialkylcarbamoyl;
  an alkyl group, which is optionally substituted by one or more, for example 1, 2, 3 or 4, substituents selected from halogen atoms and hydroxy, alkoxy, aryloxy, alkylthio, oxo, amino, mono- or di-alkylamino, acylamino, carbamoyl or mono- or di-alkylcarbamoyl groups;
  or a group of formula $-(CH_2)_n-R^6$ wherein n is an integer from 0 to 4 and $R^8$ represents:
  a cycloalkyl group;
  an aryl group, which is optionally substituted by one or more,-for example 1, 2, 3 or 4, substituents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
  or a 3- to 7-membered ring comprising from 1 to 4 heteroatoms selected from nitrogen, oxygen and sulphur, which ring is optionally substituted by one or more, for example 1, 2, 3 or 4, substituents selected from halogen atoms and alkyl, hydroxy, alkoxy, alkylenedioxy, amino, mono- or di-alkylamino, nitro, cyano or trifluoromethyl groups;
$R^2$ represents a substituent selected from $R^1$ and an alkyl group, which is substitued by a hydroxycarbonyl or an alkoxycarbonyl group.
$R^3$ and $R^5$ each independently represent a monocyclic or bicyclic aryl group, which is optionally substituted by one or more, for example 1, 2, 3 or 4, substituents selected from:
  halogen atoms;
  alkyl and alkylene groups, which are optionally substituted by one or more, for example 1, 2, 3 or 4, substituents selected from halogen atoms and phenyl, hydroxy, alkoxy, aryloxy, alkylthio, oxo, amino, mono- or di-alkylamino, acylamino, hydroxycarbonyl, alkoxycarbonyl, carbamoyl or mono- or di-alkylcarbamoyl groups;
  and phenyl, hydroxy, alkylenedioxy, alkoxy, cycloalkyloxy, alkylthio, alkylsulphinyl, amino, mono- or di-alkylamino, acylamino, nitro, acyl, hydroxycarbonyl, alkoxycarbonyl, carbamoyl, mono- or di-alkylcarbamoyl, ureido, N'-alkylureido, N',N'-dialkylureido, alkylsulphamido, aminosuphonyl, mono- or di-alkylaminosulphonyl, cyano, difluoromethoxy or trifluoromethoxy groups;
$R^4$ represents:
  a hydrogen atom;

a hydroxy, alkoxy, amino, mono- or di-alkylamino group;
an alkyl group which is optionally substituted by one or more, for example 1, 2, 3 or 4, substituents selected from halogen atoms and hydroxy, alkoxy, aryloxy, alkylthio, oxo, amino, mono- or di-alkylamino, acylamino, hydroxycarbonyl, alkoxycarbonyl, carbamoyl and mono- or di-alkylcarbamoyl groups;
or a group of formula

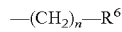

wherein n and $R^6$ are as defined above.
with the proviso that when $R^2$ is H and $R^3$ and $R^5$ are unsubstituted phenyl, $R^1$ is not methyl;
or a pharmaceutically acceptable salt thereof.

Certain pyridazin-3(2H)-one derivatives of similar structure, which do not fall within the scope of the present invention, have been disclosed in *J. Pharm. Sci.* 1991, 80, 341-348 and *J. Med. Chem.* 1999, 42, 1894-1900.

Further objectives of the present invention are to provide processes for preparing said compounds; pharmaceutical compositions comprising an effective amount of said compounds; the use of the compounds in the manufacture of a medicament for the treatment of diseases susceptible of being improved by inhibition of PDE4; and methods of treatment of diseases susceptible to amelioration by inhibition of PDE4, which methods comprise the administration of the compounds of the invention to a subject in need of treatment.

As used herein, an alkyl group can be straight or branched, and is typically a lower alkyl group. A lower alkyl group contains 1 to 6, preferably 1 to 4 carbon atoms. In particular it is preferred that such an alkyl group is represented by a methyl, ethyl, n-propyl, i-propyl, n-butyl, sec-butyl, tert-butyl, n-pentyl, 1-methylbutyl, 1-ethylpropyl, 1,2-dimethylpropyl, n-hexyl or 1-ethylbutyl group.

As used herein, an alkylene group or moiety is a divalent alkyl moiety typically having from 1 to 6 carbon atoms. Examples of $C_1$-$C_6$ alkylene groups include methylene, ethylene, propylene, butylene, pentylene and hexylene groups. When an alkylene or alkylenedioxy group is present as a substituent on another group it shall be deemed to be a single substituent, rather than a group formed by two substituents.

As used herein, the alkyl chains present in the alkoxy, alkylthio, monoalkylamino, dialkylamino, alkoxycarbonyl, monoalkylcarbamoyl, dialkylcarbamoyl, alkylenedioxy, alkylsulphinyl, monoalkylaminosulphonyl, dialkylaminosulphonyl, alkylsulphamido, N'-alkylureido, and N',N'-dialkylureido groups are typically straight or branched alkyl chains containing from 1 to 6 carbon atoms.

As used herein, an acyl group or moiety typically has from 2 to 7 carbon atoms. Thus, it is typically a group of formula —COR wherein R is a hydrocarbon chain group having from 1 to 6 carbon atoms. Preferably, it is a group of formula —COR wherein R is a $C_1$-$C_6$ alkyl group.

As used herein, a cycloalkyl group or moiety typically has from 3 to 6 carbon atoms. Examples include cyclopropyl, cyclobutyl, cyclopentyl and cyclohexyl. It is preferably cyclopropyl, cyclopentyl or cyclohexyl. When a cycloalkyl group or moiety carries 2 or more substituents, the substituents may be the same or different. As used herein, a cycloalkyloxy group is typically a said cycloalkyl group attached to an oxygen atom.

As used herein, an aryl group or moiety is typically a $C_6$-$C_{10}$ aryl group or moiety, which can be monocyclic or bicyclic, such as phenyl or naphthyl. When an aryl group or moiety carries 2 or more substituents, the substituents may be the same or different. As used herein, an aryloxy group is typically a said aryl group attached to an oxygen atom.

As used herein, a 3 to 7-membered ring comprising from 1 to 4 heteroatoms selected from nitrogen, oxygen and sulphur is typically a heteroaryl or a heterocyclyl group or moiety.

A heteroaryl group or moiety is typically a 3 to 7-membered aromatic ring, such as a 5- or 6- membered ring, containing at least one heteroatom selected from O, S and N. Examples include pyridyl, pyrazinyl, pyrimidinyl, pyridazinyl, furanyl, oxadiazolyl, oxazolyl, imidazolyl, thiazolyl, thiadiazolyl, thienyl, pyrazolidinyl, pyrrolyl and pyrazolyl groups. Oxadiazolyl, oxazolyl, pyridyl, pyrrolyl, imidazolyl, thiazolyl, thiadiazolyl. furanyl, thienyl, pyrazinyl and pyrimidinyl groups are preferred. When a heteroaryl group or moiety carries 2 or more substituents, the substituents may be the same or different.

A heterocyclyl group is typically a non-aromatic, saturated or unsaturated $C_3$-$C_7$ carbocyclic ring, in which one or more, for example 1, 2, 3 or 4, of the carbon atoms are replaced by a heteroatom selected from N, O and S. Saturated heterocyclyl groups are preferred. Examples of suitable heterocyclyl groups include piperidinyl, piperazinyl, morpholinyl, 4,5-dihydro-oxazolyl, 3-aza-tetrahydrofuranyl, imidazolidinyl and pyrrolidinyl groups. Where a heterocyclyl group carries 2 or more substituents, the substituents may be the same or different.

As used herein, a halogen atom, is typically a chlorine, fluorine or bromine atom.

As used herein, some of the atoms, groups, moieties, chains or cycles present in the general structures of the invention are "optionally substituted". This means that these atoms, groups, moieties, chains or cycles can be either unsubstituted or substituted by one or more, for example 1, 2, 3 or 4, substituents, whereby the hydrogen atoms bound to the unsubstituted atoms, groups, moieties, chains or cycles are replaced by chemically acceptable atoms, groups, moieties, chains or cycles.

Compounds of formula (I) containing one or more chiral centre may be used in enantiomerically or diastereoisomerically pure form, or in the form of a mixture of isomers.

As used herein, a pharmaceutically acceptable salt is a salt with a pharmaceutically acceptable acid or base. Pharmaceutically acceptable acids include both inorganic acids, for example hydrochloric, sulphuric, phosphoric, diphosphoric, hydrobromic, hydroiodic or nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, aralkyl amines and heterocyclic amines.

Preferred compounds of formula (I) are those wherein $R^1$ is a hydrogen atom; a straight or branched $C_1$-$C_4$ alkyl group, which is optionally substituted by halogen atoms and/or 1 or 2 substituents selected from hydroxy, alkoxy, amino, monalkylamino and dialkylamino groups; or a group of formula —$(CH_2)_n$—$R^6$, wherein n is an integer from 0 to 4 and $R^6$ is an optionally substituted phenyl, cycloalkyl or 5- to 6-membered heterocyclic ring comprising at least one nitrogen atom, preferably a pyridine ring. Most preferably, $R^1$ is an unsubstituted straight or branched $C_1$-$C_4$ alkyl group, or a group of formula —$(CH_2)_n$—$R^6$, wherein n is 0 or 1 and $R^6$ is cyclopropyl, phenyl or pyridyl.

Further preferred compounds of formula (I) are those wherein $R^2$ is a hydrogen atom or a group selected from alkoxycarbonyl; carbamoyl; a straight $C_1$-$C_4$ alkyl group, which is optionally substituted by a hydroxy group; or a group of formula —(CH$_2$)$_n$—R$^6$, wherein n is 0 and R$^6$ is a phenyl ring, which is optionally substituted by 1 or 2 substituents selected from halogen, alkyl, acyl, alkoxy, alkylthio and alkoxycarbonyl. Most preferably, R$^2$ is a hydrogen atom, an unsubstituted straight C$_1$-C$_4$ alkyl group or a phenyl ring, which is optionally substituted by 1 or 2 substituents selected from halogen, alkyl, acyl, alkoxy, alkylthio and alkoxycarbonyl.

Also preferred are compounds wherein R$^3$ is a phenyl or naphthyl group, which is optionally substituted by 1 or 2 substituents selected from halogen, hydroxy, alkoxy, cycloalkyloxy, alkylthio, cyano, nitro, acyl, hydroxycarbonyl, alkoxycarbonyl, acylamino, aminosulphonyl, carbamoyl, trifluoromethoxy, alkylenedioxy, alkyl and alkylene group, wherein said alkyl and alkylene groups are optionally substituted by halogen atoms or by a group selected from hydroxy, oxo, phenyl, amino and hydroxycarbonyl.

R$^4$ is in the preferred embodiments of the invention a substituent selected from hydrogen; hydroxy; alkoxy; amino; monoalkylamino; dialkylamino; a straight or branched C$_1$-C$_6$ alkyl group, which is optionally substituted by hydroxy, alkoxy, amino, monoalkylamino or dialkylamino groups; or a group of formula —(CH$_2$)$_n$—R$^6$, wherein n is 0, 1 or 2 and R$^6$ is a phenyl group. Most preferably, R$^4$ is a substituent selected from hydrogen, methoxy, unsubstituted straight or branched C$_1$-C$_6$ alkyl and phenyl.

In further preferred embodiments R$^5$ is a phenyl group, which is optionally substituted by 1 or 2 substituents selected from halogen, hydroxy, alkoxy, cycloalkyloxy, alkylthio, alkylsulphinyl, nitro, cyano, hydroxycarbonyl, alkoxycarbonyl, carbamoyl, monalkylcarbamoyl, dialkylcarbamoyl, ureido, N'-alkylureido, N',N'-dialkylureido and an optionally substituted straight or branched C$_1$-C$_6$ alkyl group. Most preferably, R$^5$ is a phenyl group, which is optionally substituted by 1 or 2 substituents selected from halogen, alkoxy, cycloalkyloxy, alkylthio, alkylsulphinyl and nitro.

Particular individual compounds of the invention include:
5-Acetyl-2-ethyl4-[(3-fluorophenyl)amino]-6-phenylpyridazin-3(2H)-one
5-Acetyl-4-[(3,5-difluorophenyl)amino]-2-ethyl-6-phenylpyridazin-3(2H)-one
5-Acetyl-4-[(3,5-dichlorophenyl)amino]-2-ethyl-6-phenylpyridazin-3(2H)-one.
5-Acetyl-2-ethyl-4-[(3-nitrophenyl)amino]-6-phenylpyridazin-3(2H)-one
5-Acetyl-2-ethyl-4-[(4methylphenyl)amino]-6-phenylpyridazin-3(2H)-one
5-Acetyl-2-ethyl-4-[(2-methylphenyl)amino]-6-phenylpyridazin-3(2H)-one
5-Acetyl-2-ethyl-4-[(2-methoxyphenyl)amino]-6-phenylpyridazin-3(2H)-one
5-Acetyl-2-ethyl-4-(1-naphthylamino)-6-phenylpyridazin-3(2H)-one
5-Acetyl-2-ethyl-4{[(methylthio)phenyl]amino}-phenylpyridazin-3(2H)-one
5-Acetyl-4-[(4-acetylphenyl)amino]-2-ethyl-6-phenylpyridazin-3(2H)-one
5-Acetyl-4-{[4-(dimethylamino)phenyl]amino}-2-ethyl-6-phenylpyridazin-3(2H)-one
5-Acetyl-2-ethyl-4-(2-naphthylamino)-6-phenylpyridazin-3(2H)-one
5-Acetyl-4-[(2-chlorophenyl)amino]-2-ethyl-6-phenylpyridazin-3(2H)-one
5-Acetyl-2-ethyl-6-phenyl-4-([3-(trifluoromethoxy)phenyl]amino)pyridazin-3(2H)-one
5-Acetyl-2-ethyl-6-phenyl-4-([2-(trifluoromethyl)phenyl]amino)pyridazin-3(2H)-one 5-Acetyl-2-ethyl-4-[(2,5-dimethoxyphenyl)amino]-6-phenylpyridazin-3(2H)-one
5-Acetyl-2-ethyl-4-[(2-fluoro-3-methoxyphenyl)amino]6-phenylpyridazin-3(2H)-one
5-Acetyl-4-[(2,3-dichlorophenyl)amino]-2-ethyl-6-phenylpyridazin-3(2H)-one
5-Acetyl-4-[(5-chloro-2-methoxyphenyl)amino]-2-ethyl-6-phenylpyridazin-3(2H)-one
5-Acetyl-2-ethyl4[(5-fluoro-2-methoxyphenyl)amino]-6-phenylpyridazin-3(2H)-one
Methyl 4-({5-acetyl-2-ethyl-6-[4(methylthio)phenyl]-3-oxo-2,3-dihydropyridazin-4-yl}amino)benzoate
5-Acetyl-2-ethyl[(3-fluorophenyl)amino]-6-[4-(methylthio)phenyl]pyridazin-3(2H)-one
4-({5-Acetyl-2-ethyl-6-[(methylthio)phenyl]-3-oxo-2,3-dihydropyridazin-4-yl}amino)benzoic acid
5-Acetyl-2-ethyl-6-[4-(methylthio)phenyl-4-(1-naphthylamino)pyridazin-3(2H)-one
5-Butyryl-2-ethyl-4-[(3-fluorophenyl)amino]-[4-(methylthio)phenyl]pyridazin-3(2H)-one
2-Ethyl-5-(2-ethylbutanoyl)-4-[(3-fluorophenyl)amino]-6-[4-(methylthio)phenyl]pyridazin-3(2H)-one
2-Ethyl-5-(2-ethylbutanoyl)-6-[4-(methylthio)phenyl]-4-(naphth-1-ylamino)pyridazin-3(2H)-one
Methyl 4-({5-acetyl-2-ethyl-4-6-[4-(methylsulphinyl)phenyl]-3-oxo-2,3-dihydropyrida-zin-4-yl}amino)benzoate
5-Acetyl-2-ethyl-4-[(3-fluorophenyl)amino]-6-[4-(methylsulphinyl)phenyl]pyridazin-3(2H)-one
5-Acetyl-4-[(3-chlorophenyl)amino]-2-ethyl+[4-(methylsulphinyl)phenyl]pyridazin-3(2H)-one
5-Acetyl-2-ethyl-4-[(2-methylphenyl)amino]-6[(methylsulphinyl)phenylpyridazin-3(2H)-one
5-Acetyl-2-ethyl-6-[4-(methylsulphinyl)phenyl]-4-(1-naphthylamino)pyridazin-3(2H)-one
5-Acetyl-2-ethyl-6-[4-(methylsulphinyl)phenyl]-4-(3-nitrophenyl)amino]pyridazin-3(2H)-one
5-Acetyl-2-ethyl-6-[4-(methylsulphinyl)phenyl]-4-[(2-methoxyphenyl)amino]pyridazin-3(2H)-one
5-Acetyl-2-ethyl-6-[4-(methylsulphinyl)phenyl]-4-1(3-methoxyphenyl)amino]pyridazin-3(2H)-one
5-Acetyl-6-[3-(cyclopentyloxy)-4-methoxyphenyl-2-ethyl-4-[(3-fluorophenyl)amino]pyridazin-3(2H)-one
5-Acetyl-6-[3-(cyclopentyloxy)-4-methoxyphenyl]-2-ethyl4-(1-naphthylamino)pyridazin-3(2H)-one
5-Acetyl-2-methyl-4-(1-naphthylamino)-6-phenylpyridazin-3(2H)-one
5-Acetyl-4-[(3,5-difluorophenyl)amino]-2-methyl-6-phenylpyridazin-3(2H)-one
5-Acetyl-4-[(3-chlorophenyl)amino]-2-methyl-6-phenylpyridazin-3(2H)-one
5-Acetyl-2-benzyl-4-[(3,5-difluorophenyl)amino]-6-phenylpyridazin-3(2H)-one
5-Acetyl-2-benzyl-4-[(3-fluorophenyl)amino]-phenylpyridazin-3(2H)-one
5-Acetyl-2-benzyl-4-[(3-chlorophenyl)amino]-phenylpyridazin-3(2H)-one
5-Acetyl-2-(cyclopropylmethyl)-4-(1-naphthylamino)-6-phenylpyridazin-3(2H)-one
5-Acetyl-2-(cyclopropylmethyl)-4-[(3-fluorophenyl)amino]-6-phenylpyridazin-3(2H)-one
5-Acetyl-4-[(3-chlorophenyl)amino]-2-(cyclopropylmethyl)-6-phenylpyridazin-3(2H)-one
5-Acetyl-4-(1-naphthylamino)-6-phenyl-2-pyridin-4-ylmethylpyridazin-3(2H)-one
5-Acetyl-4[(3-fluorophenyl)amino]-6-phenyl-2-pyridinylmethylpyridazin-3(2H)-one 5-Acetyl-2-ethyl-4-[(3-methylphenyl)amino]-6-phenylpyridazin-3(2H)-one
4-[(5-Acetyl-2-ethyl-3-oxo-6-phenyl-2,3-dihydropyridazin-4-yl)amino]benzoic acid
2-[(5-Acetyl-2-ethyl-3-oxo-6-phenyl-2,3-dihydropyridazinyl)amino]benzoic acid
5-Acetyl-4-[(3-chlorophenyl)amino]-2-ethyl-6-phenylpyridazin-3(2H)-one
5-Acetyl-4-[(3-bromophenyl)amino]-2-ethyl-6-phenylpyridazin-3(2H)-one
5-Acetyl-4-[(3,4dimethoxyphenyl)amino]-2-ethyl-6-phenylpyridazin-3(2H)one
5-Acetyl-2-ethyl-4-{[4-(hydroxymethyl)phenyl]amino}-6-phenylpyridazin-3(2H)-one
5-Acetyl-4-(1,1'-biphenyl-4-ylamino)-2-ethyl-6-phenylpyridazin-3(2H)-one
5-Acetyl-2-ethyl-6-phenyl4-(5,6,7,8-tetrahydronaphthalen-1-ylamino)pyridazin-3(2H)-one
5-acetyl-4{[3-(cyclopentyloxy)-4-methoxyphenyl]amino})-2-ethyl-6-phenylpyridazin-3(2
5-Acetyl-2-ethyl-4-[N-methyl-N-phenylamino]-6-phenylpyridazin-3(2H)-one
5-Acetyl-4-(1,3-benzodioxol-5-ylamino)-2-ethyl-6-phenylpyridazin-3(2H)-one
5-Acetyl-2-ethyl-4-[(4-methoxyphenyl)amino]-6-phenylpyridazin-3(2H)-one
5-Acetyl-4-[(4-chlorophenyl)amino]-2-ethyl-6-phenylpyridazin-3(2H)-one
5-Acetyl-4-[(4-bromophenyl)amino]-2-ethyl-6-phenylpyridazin-3(2H)-one
5-Acetyl-2-ethyl-6-phenyl-4-{[3-(trifluoromethyl)phenyl]amino}pyridazin-3(2H)-one
5-Acetyl-4-[(3-chloromethoxyphenyl)amino]-2-ethyl-6-phenylpyridazin-3(2H)-one
5-Acetyl-2-ethyl-4-[(3-hydroxyphenyl)amino]-6-phenylpyridazin-3(2-one
3-[(5-Acetyl-2-ethyl-3-oxo-6-phenyl-2,3-dihydropyridazin-4-yl)amino]benzoic acid
5-Acetyl-2-ethyl-4-[(2-fluorophenyl)amino]-6-phenylpyridazin-3(2H)-one
4-(5-Acetyl-2-ethyl-3-oxo-6-phenyl-2,3-dihydro-pyridazin-4-ylamino)-benzoic acid ethyl ester
5-Acetyl-2-ethyl-4-[(4-fluorophenyl)amino]phenylpyridazin-3(2H)-one
2-[(5-acetyl-2-ethyl-3-oxo-6-phenyl-2,3-dihydropyridazin-4-yl)amino]-4-fluorobenzoic acid
3-[(5-Acetyl-2-ethyl-3-oxo-6-phenyl-2,3-dihydropyridazin-4-yl)amino]-4-benzonitrile
4-[(5-Acetyl-2-ethyl-3-oxo-6-phenyl-2,3-dihydropyridazinyl)amino]-2-hydroxybenzoic acid
5-Acetyl-2-ethyl-4-[(3-hydroxy-4-methoxyphenyl)amino]-6-phenylpyridazin-3(2H)-one
4-[(5-Acetyl-2-ethyl-3-oxo-6-phenyl-2,3-dihydropyridazin-4-yl)amino]benzamide
5-Acetyl-2-ethyl-4-{[-(methylthio)phenyl]amino}-6-phenylpyridazin-3(2H)-one
5-Acetyl-2-ethyl-4-(3-methoxyphenyl)amino]-6-phenylpyridazin-3(2H)-one
5-Acetyl-4-[(3-acetylphenyl)amino]-2-ethyl-6-phenylpyridazin-3(2H)-one
{4-[(5-Acetyl-2-ethyl-3-oxo-6-phenyl-2,3-dihydropyridazinyl)amino]phenyl}acetic acid
5-Acetyl-4-[4-(tert-butylphenyl)amino]-2-ethyl-6-phenylpyridazin-3(2H)-one
4-[(5-Acetyl-2-ethyl-3-oxo-6-phenyl-2,3-dihydropyridazin-4-yl)amino]benzenesulphonamide
4-{4-[(5-Acetyl-2-ethyl-3-oxo-6-phenyl-2,3-dihydropyridazinyl)amino]phenyl}-4-oxobutanoic acid
3-[(5-Acetyl-2-ethyl-3-oxo-6-phenyl-2,3-dihydropyridazin-4-yl)amino]-N-butylbenzenesulphonamide
5-Acetyl-2-ethyl-4-[(1-oxo-2,3-dihydro-1H-inden-5-yl)amino]-6-phenylpyridazin-3(2H)-one
N-{4-[(5-Acetyl-2-ethyl-3-oxo-6-phenyl-2,3-dihydropyridazin-4-yl)amino]phenyl}acetamide
4-[5-Acetyl-6-(3-chlorophenyl)-2-ethyl-3-oxo-2,3-dihydropyridazin-4-ylamino]benzoic acid
5-Acetyl-6-(3-chlorophenyl)-4-[(3-chlorophenyl)amino]-2-ethylpyridazin-3(2H)-one
5-Acetyl-6-(3-chlorophenyl)-2-ethyl-4-[(3-fluorophenyl)amino]pyridazin-3(2H)-one
5-Acetyl-4-[(3-chlorophenyl)amino]-2-ethyl-6-(4-fluorophenyl)pyridazin-3(2H)-one
5-Acetyl-4-[(3-bromophenyl)amino]-2-ethyl-6-(3-fluorophenyl)pyridazin-3(2H)-one
5-Acetyl-2-ethyl-4-[(3-fluorophenyl)amino]-6-(3-fluorophenyl)pyridazin-3(2H)-one
5-Acetyl-4-[(3-chlorophenyl)amino]-2-ethyl-6-(3-fluorophenyl)pyridazin-3(2H)-one
5-Acetyl-4-[(3-chlorophenyl)amino]-2-ethyl-6-(3-nitrophenyl)pyridazin-3(2H)-one
5-Acetyl-2-ethyl-4-[(3-fluorophenyl)amino]-6-(3-nitrophenyl)pyridazin-3(2H)-one
4-{[5-Acetyl-2-ethyl-6-(3-nitrophenyl)-3-oxo-2,3-dihydropyridazin4-yl]amino}benzoic acid
5-Acetyl-4-[(3-bromophenyl)amino]-2-ethyl-6-(3-nitrophenyl)pyridazin-3(2H)-one
5-Acetyl-2-ethyl-4-(naphthalen-1-ylamino)-6-(3-nitrophenyl)pyridazin-3(2H)-one
5-Butyryl-4-[(3-chlorophenyl)amino]-2-ethyl-6-phenylpyridazin-3(2H)-one
5-Acetyl-4-[(3-chlorophenyl)amino]-6-phenyl-2-propylpyridazin-3(2H)-one
5-Acetyl-2-butyl-4-[(3-chlorophenyl)amino]-6-phenylpyridazin-3(2H)-one
5-Acetyl-4-[(3-bromophenyl)amino]-2-butyl-6-phenylpyridazin-3(2H)-one
5-Acetyl-4-[N-(3,5dichlorophenyl)-N-(3-fluorophenyl)amino]-2-ethyl-6-phenylpyridazin-3(2H)-one
5-Acetyl-4-[bis(3-fluorophenyl)amino]-2-ethyl-6-phenylpyridazin-3(2H)-one
5-Acetyl-4-[bis(3-chlorophenyl)amino]-2-ethyl-6-phenylpyridazin-3(2H)-one
5-Acetyl-2-ethyl-4-[bis(3-methylsulphanylphenyl)amino]-6-phenylpyridazin-3(2H)-one
5-Acetyl-4-[bis(3-acetylphenyl)amino]-2-ethyl-6-phenylpyridazin-3(2H)-one
5-Acetyl-4-[bis-(3,5dichlorophenyl)amino]-2-ethyl-6-phenyl-2H-pyridazin-3-one
methyl 4-{N-(5-acetyl-2-ethyl-6-(4-methylsulphinylphenyl)-3-oxo-2,3-dihydropyri-dazin-4-yl)-N-[4-(methoxycarbonyl)phenyl]amino}benzoate
5-Acetyl-2-(cyclopropylmethyl)-4-[(3,5-difluorophenyl)amino]-6-phenylpyridazin-3(2H)-one
5-Acetyl-4-[(3-fluorophenyl)amino]-2-methyl-6-phenylpyridazin-3(2H)-one
4-[(5-Acetyl-2-methyl-3-oxo-6-phenyl-2,3-dihydropyridazin-4-yl)amino]benzoic acid
5-Acetyl-4-[(3,5-dichlorophenyl)amino]-2,6-diphenylpyridazin-3(2H)-one
5-Acetyl-4-[(3-fluorophenyl)amino]-2,6-diphenylpyridazin-3(2H)-one
5-Acetyl-4-(1-naphthylamino)-2,6-diphenylpyridazin-3(2H)-one 5-Acetyl-4-[(3,5-difluorophenyl)amino]-2,6-diphenylpyridazin-3(2H)-one
5-Acetyl-4-[(3-chlorophenyl)amino]-2,6-diphenyipyridazin-3(2H)-one
5-Benzoyl-4-[(3-chlorophenyl)amino]-2-ethyl-6-methylpyridazin-3(2H)-one
5-[(3-Chlorophenyl)amino]-1-ethyl-6-oxo-3-phenyl-1,6-dihydropyridazine-4-carbaldehyde
Methyl 5-[(3-chlorophenyl)amino]-1-ethyl-6-oxo-3-phenyl-1,6-dihydropyridazine-4-carboxylate
5-Acetyl-2-cyclobutyl-4-[(3,5-dichlorophenyl)amino]-6-phenylpyridazin-3(2H)-one
5-Acetyl-4-[(3-chlorophenyl)(2-hydroxyethyl)amino]-2-ethyl-6-phenylpyridazin-3(2H)-one
4-[(3-Chlorophenyl)amino]-5-[(dimethylamino)acetyl]-2-ethyl-6-phenylpyridazin-3(2H)-one.
4-{[2-Ethyl-5-(methoxyacetyl)-6-phenyl-3-oxo-2,3-dihydropyridazin-4-yl]amino}benzoic acid
5-[(3-Cyanophenyl)amino]-1-ethyl-6-oxo-3-phenyl-1,6-dihydropyridazine-4-carboxamide
5-[(3-Cyanophenyl)amino]-1-ethyl-6-oxo-3-phenyl-1,6-dihydropyridazine-4-carboxylic acid
3-{4-Acetyl-5-[(3,5-difluorophenyl)amino]-1-ethyl-6-oxo-1,6-dihydropyridazin-3-yl}benzoic acid
3-{4-Acetyl-5-[(3,5-difluorophenyl)amino]-1-ethyl-6-oxo-1,6-dihydropyridazin-3-yl}benzonitrile
N-(3-{4-Acetyl-5-[(3,5-difluorophenyl)amino]-1-ethyl-6-oxo-1,6-dihydropyridazin-3-yl}phenyl)urea
5-Acetyl-4-[(3-chlorophenyl)amino]-6-phenylpyridazin-3(2H)-one
N-Benzyl-5-[(3-chlorophenyl)amino]-1-ethyl-6-oxo-3-phenyl-1,6-dihydropyridazine-4-carboxamide
4-[(3-Chlorophenyl)amino]-2ethyl-5-(phenoxyacetyl)-6-phenylpyridazin-3(2H)-one
Of outstanding interest are:
5-Acetyl-2-ethyl-4-[(3-fluorophenyl)amino]-6-phenylpyridazin-3(2H)-one
5-Acetyl-4-[(3,5-difluorophenyl)amino]-2-ethyl-6-phenylpyridazin-3(2H)-one
5-Acetyl-2-ethyl-4-(1-naphthylamino)-6-phenylpyridazin-3(2H)-one
5-Acetyl-4-[(2-chlorophenyl)amino]-2-ethyl-6-phenylpyridazin-3(2H)-one
4-({5-Acetyl-2-ethyl-6-[(methylthio)phenyl]-3-oxo-2,3-dihydropyridazine-4-yl}amino)benzoic acid
5-Acetyl-2-ethyl-4-[(2-methylphenyl)amino]-6-[4-(methylsulphinyl)phenyl]pyridazin-3(2H)-one
5-Acetyl-6-[3-(cyclopentyloxy)-4-methoxyphenyl]-2-ethyl-4-[(3-fluorophenyl)amino]pyridazin-3(2H)-one
5-Acetyl-4-[(3,5-difluorophenyl)amino]-2-methyl-6-phenylpyridazin-3(2H)-one
5-Acetyl-2-(cyclopropylmethyl)-4-[(3-fluorophenyl)amino]-6-phenylpyridazin-3(2H)-one
5-Acetyl-4-[(3-chlorophenyl)amino]-2-(cyclopropylmethyl)-6-phenylpyridazin-3(2)-one
4-[(5-Acetyl-2-ethyl-3-oxo-6-phenyl-2,3-dihydropyridazin-4-yl)amino]benzoic acid
5-Acetyl-4-[(3-chlorophenyl)amino]-2-ethyl-6-phenylpyridazin-3(2H)-one
3-[(5-Acetyl-2-ethyl-3-oxo-6-phenyl-2,3-dihydropyridazin-4-yl)amino]benzonitrile
4-[5-Acetyl-6-(3-chlorophenyl-2-ethyl-3-oxo-2,3-dihydropyridazin-4-ylamino]benzoic acid
5-Acetyl-6-(3-chlorophenyl)-2-ethyl-4-[(3-fluorophenyl)amino]pyridazin-3(2H)-one
5-Acetyl-2-ethyl-4-[(3-fluorophenyl)amino]-6-(3-fluorophenyl)pyridazin-3(2H)-one
5-Acetyl-4-[(3-chlorophenyl)amino]-2-ethyl-6-(3-fluorophenyl)pyridazin-3(2H)-one
5-Acetyl-2-ethyl-4-(naphthalen-1-ylamino)-6-(3-nitrophenyl)pyridazin-3(2H)-one
5-Acetyl-2-(cyclopropylmethyl)-4-[(3,5-difluorophenyl)amino]-6-phenylpyridazin-3(2H)-one In accordance with another embodiment, the present invention provides processes for preparing the novel pyridazin-3(2H)-one derivatives of formula (I). These compounds may be prepared following one of the processes described below.

When $R^2$ is H, the compounds of formula (I) are obtained by reaction of the corresponding 4-aminopyridazin-3(2M-one derivative (II)

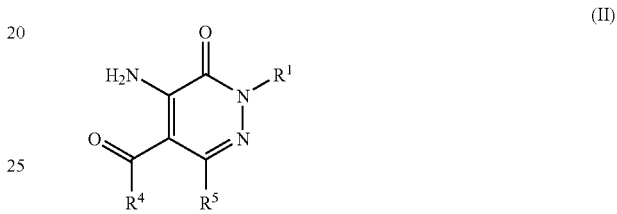

(II)

wherein $R^1$, $R^4$ and $R^5$ are as defined above and the corresponding boronic acid (IIIa)

(IIIa)

wherein $R^3$ is as defined above. The reaction is carried out in the presence of a copper salt such as cupric acetate and an organic base, preferably an amine base such as triethylamine, in an inert solvent such as dioxane, methylene chloride or tetrahydrofuran, at a temperature from −20° C. to the boiling point of the solvent.

When $R^2$ is aryl or substituted aryl, the compounds of formula (I) are obtained by reaction of the corresponding 4-aminopyridazin-3(2H)-one derivative (IV):

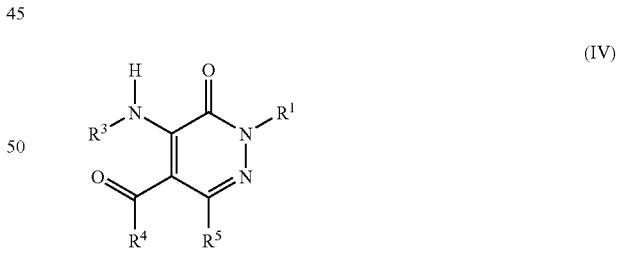

(IV)

wherein $R^1$, $R^3$, $R^4$ and $R^5$ are as defined above and the corresponding boronic acid (IIIb)

(IIIb)

wherein $R^2$ is an aryl or substituted aryl group. The reaction is carried out in the presence of a copper salt such as cupric acetate and an organic base, preferably an amine base such as triethylamine, in an inert solvent such as dioxane, methylene chloride or tetrahydrofuran, at a temperature from −20° C. to the boiling point of the solvent.

Alternatively, the compounds of formula (I) may be obtained by reaction of the corresponding 4-nitropyridazin-3(2M-one derivative (V):

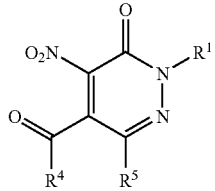

wherein $R^1$, $R^4$ and $R^5$ are as defined above and the corresponding amine (VI)

wherein $R^2$ and $R^3$ are as defined above, by methods known per se, e.g. G. Ciciani et al. *Farmaco* 1991, 46, 873.

When R4 is alkoxy, aryloxy or-mono- or di-alkylamino or mono- or di-arylamino, the compounds of formula (I) can be obtained by reaction of the corresponding 4-aminopyridazin-3(2H)-one derivative (XVII):

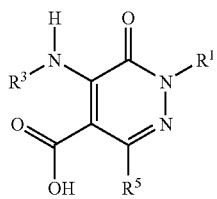

wherein R1, R3 and R5 are as defined above and the corresponding alcohol or amine in the presence of a coupling agent such as dicyclohexylcarbodiimide, O-7-(azabenzotriazol-1-yl)-1,1,3,3-tetramethyluronium hexafluorofosfate (HATU) or benzotriazol-1-yloxytris-(dimethylamino)fosfonium hexafluorofosfate (BOP) in an inert solvent such as dichloromethane, tetrahydrofurane, dioxane, N,N-dimethylformamide and in the presence of an organic base such as triethylamine or ethyldiisopropylamine when required, at a temperature from −20° C. to the boiling point of the solvent.

When R4 is alkoxy the compounds of formula (I) can also be obtained from the corresponding 4-aminopyridazin-3(2H)-one derivative (XVII) and the corresponding alkylating agent in the presence of an inorganic base such as potassium carbonate in an inert solvent such as N,N-dimethylformamide or acetone at a temperature from −20° C. to the boiling point of the solvent.

The 4-aminopyridazin-3(2H)-one derivatives of general formula (II) may be prepared by hydrogenation of an isoxazolo[3,4-d]pyridazin-7(6H)-one of formula (VII)

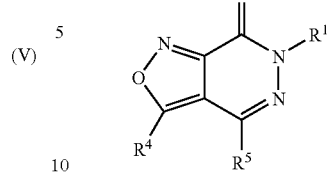

wherein $R^1$, $R^4$ and $R^5$ are as defined above. The hydrogenation may be performed using for example hydrogen in the presence of a catalyst by methods known per se, e.g. V. Dal Piaz et al. *Heterocycles*, 1991, 32, 1173. Alternatively, the reaction may be accomplished by transfer hydrogenation using an organic hydrogen donor and a transfer agent, such as ammonium formate or hydrazine by methods known per se, e.g. V. Dal Piaz et al. *Heterocycles*, 1991, 32, 1173.

Alternatively, when $R^1$ is not H, the 4-aminopyridazin-3(2H)-one derivatives of formula (II) may be prepared by reaction of a compound of general formula (VIII)

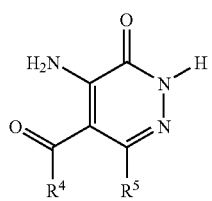

wherein $R^4$ and $R^5$ are as defined above, with an alkylating agent of formula (IX)

$$R^1-X \quad (IX)$$

wherein $R^1$ is as defined above and X is a leaving group such as a chlorine or a bromine atom or a methanesulphonate, p-toluenesulphonate or a benzenesulphonate group, by methods known per se, e.g. V. Dal Piaz et al. *Eur. J. Med. Chem.* 1996, 31, 65.

The 4-nitropyridazin-3(2H)-one derivatives of formula (V) may be prepared by oxidation of an isoxazolo[3,4-d]pyridazin-7(6H)-one of formula (VII)

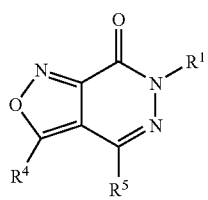

wherein $R^1$, $R^4$ and $R^5$ are as defined above. The oxidation may be performed using for example cerium ammonium nitrate under acidic conditions by methods known per se, e.g. V. Dal Piaz et al. *Synthesis,* 1989, 213.

When $R^1$ is not H, isoxazolo[3,4-d]pyridazin-7(6H)-ones of formula (VII) may be obtained by reaction of a compound of general formula (X)

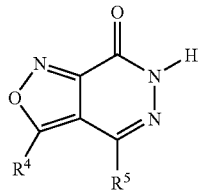
(X)

wherein $R^4$ and $R^5$ are as defined above with an alkylating agent of formula (IX)

R¹—X  (IX)

wherein $R^1$ is as hereinbefore defined and X is a leaving group such as a chlorine or a bromine atom or a methanesulphonate, p-toluenesulphonate or a benzenesulphonate group, by methods known per se, e.g. V. Dal Piaz et al. *Drug Des. Discovery* 1996, 14, 53.

The 4-aminopyridazin-3(2H)-one derivatives of general formula (II) may alternatively be

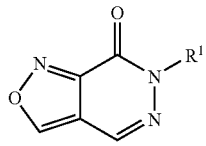

obtained by reaction of a compound of formula (XVIII) wherein R1 and R5 are as defined above with an aldehyde or a ketone, by methods known per se, eg. G. Ciciani et al. *Il Farmaco* 1991, 46, 873. The resulting substituted vinyl derivative is then reduced using for example hydrogen in the presence of a catalyst such as palladium on charcoal in a solvent such as methanol, ethanol or ethyl acetate to yield the corresponding 4aminopyridazin-3(2H)-one (II).

The isoxazolo[3,4-d]pyridazin-7(6H)-one of formula (VII) can be obtained from a 3-(bromomethyl)isoxazolo[3,4-d]pyridazin-7(6H)-one of formula (XIX)

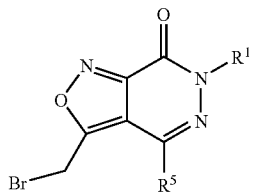
(XIX)

by reaction with a nucleofile such as an alkoxide, an amine or a thiol by methods known per se, e.g. F. Montesano et al. *Bioorg. Med. Chem. Lett.* 1998, 6, 925.

The 4-aminopyridazin-3(2H)-one derivatives of general formula (XVII) may be prepared by hydrogenation of an isoxazolo[3,4-d]pyridazin-3,7-dione of formula (XX)

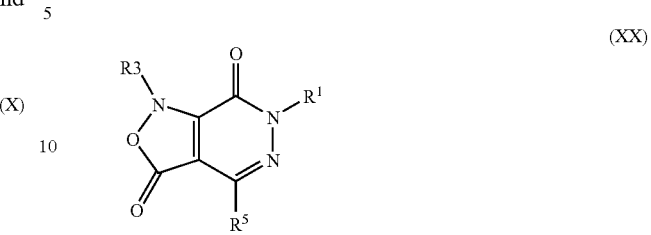
(XX)

wherein $R^1$ and $R^5$ are as defined above. The hydrogenation may be performed using for example hydrogen in the presence of a catalyst by methods known per se, e.g. V. Dal Piaz et al. *Heterocycles,* 1991, 32, 1173. Alternatively, the reaction may be accomplished by transfer hydrogenation using an organic hydrogen donor and a transfer agent, such as ammonium formate or hydrazine by methods known per se, e.g. V. Dal Piaz et al. *Heterocycles,* 1991, 32, 1173.

The isoxazolo[3,4-d]pyridazin-3,7dione of formula (XX) may be obtained by reaction of the corresponding isoxazolo[3,4-d]pyridazin-7(6H)-one of formula (XXI)

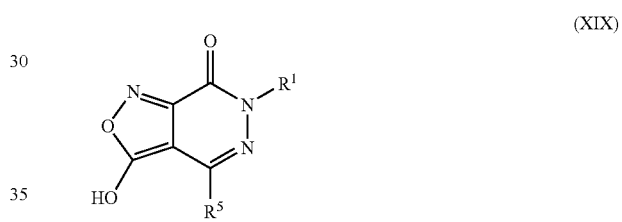
(XIX)

wherein $R^1$ and $R^5$ are as defined above and the corresponding boronic acid (IIIa)

R³—B(OH)₂  (IIIa)

wherein $R^3$ is as defined above. The reaction is carried out in the presence of a copper salt such as cupric acetate and an organic base, preferably an amine base such as triethylamine, in an inert solvent such as dioxane, methylene chloride or tetrahydrofuran, at a temperature from −20° C. to the boiling point of the solvent.

The isoxazolo[3,4-d]pyridazin-7(6H)-ones of formulas (VII) and (XXI) may also be obtained alternatively by reaction of a compound of general formula (XI)

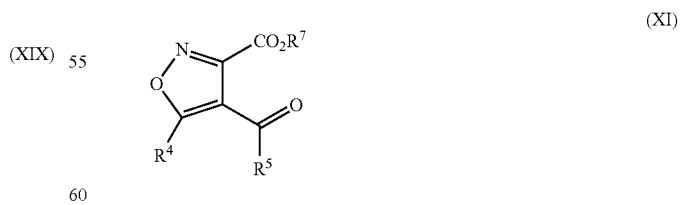
(XI)

wherein $R^4$ and $R^5$ are as defined above and $R^7$ is an alkyl substituent with a hydrazine of general formula (XII)

R¹—NHNH₂  (XII)

wherein $R^1$ is as defined above by methods known per se, e.g. G. Renzi et al., *Gazz. Chim. Ital.* 1965, 95, 1478.

The isoxazole derivatives of formula (XI) may be obtained by reaction of a 1,3-dicarbonylic compound of general formula (XIII)

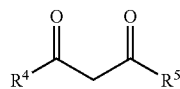

(XIII)

wherein $R^4$ and $R^5$ are as defined above and a compound of formula (XIV)

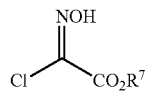

(XIV)

wherein $R^7$ is as defined above by methods known per se, e.g. G. Renzi et al., *Gazz. Chim. Ital.* 1965, 95, 1478.

The dicarbonylic compounds of formula (XIII) may be obtained by reaction of a methyl ketone of formula (XV)

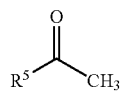

(XV)

wherein $R^5$ is as defined above and an ester of formula (XVI)

 (XVI)

wherein $R^8$ is alkyl and $R^4$ is as defined above by methods known per se, e.g. V. V. Popic et al., *Synthesis* 1991, 195.

When the defined groups $R^1$ to $R^5$ are susceptible to chemical reaction under the conditions of the hereinbefore described processes or are incompatible with said processes, conventional protecting groups may be used in accordance with standard practice, for example see T. W. Greene and P. G. M. Wuts in 'Protective Groups in Organic Chemistry', 3$^{rd}$ Edition, John Wiley & Sons (1999). It may be that deprotection will form the last step in the synthesis of compounds of formula (I).

The pharmaceutically acceptable salts of the compounds of the present invention represented by formula (I) may be acid addition salts or alkali addition salts. Examples of the acid addition salts include mineral acid addition salts such as, for example, hydrochloride, hydrobromide, hydroiodide, sulphate, nitrate, phosphate, diphosphate, and organic acid addition salts such as, for example, acetate, benzoate, maleate, fumarate, citrate, oxalate, ascorbate, succinate, tartrate, malate, mandelate, methanesulphonate, ethanesulphonate, benzenesulphonate and p-toluenesulphonate. Examples of the alkali addition salts include inorganic salts such as, for example sodium, potassium, calcium, magnesium and ammonium salts and organic alkali salts such as, for example, ethylenediamine, ethanolamine, N,N-dialkylenethanolamine, triethanolamine and basic amino acid salts.

The compounds of the present invention represented by the above described formula (I) may include enantiomers depending on their asymmetry or diastereoisomers. The single isomers and mixtures of the isomers fall within the scope of the present invention.

PDE4 Assay Procedure

Compounds to be tested were resuspended in DMSO at a stock concentration of 1 mM. The compounds were tested at different concentrations varying from 10 μM to 10 pM to calculate an $IC_{50}$. These dilutions were done in 96-well plates. In some cases, plates containing diluted compounds were frozen before being assayed. In these cases, the plates were thawed at room temperature and stirred for 15 minutes.

Ten microliters of the diluted compounds were poured into a "low binding" assay plate. Eighty microliters of reaction mixture containing 50 mM Tris pH 7.5, 8.3 mM $MgCl_2$, 1.7 mM EGTA, and 15 nM [3H]-cAMP were added to each well. The reaction was initiated by adding ten microliters of a solution containing PDE4. The plate was then incubated under stirring for 1 hour at room temperature. After incubation the reaction was stopped with 50 microliters of SPA beads, and the reaction was allowed to incubate for another 20 minutes at room temperatures before measuring radioactivity using standard instrumentation.

The reaction mixture was prepared by adding 90 ml of $H_2O$ to 10 ml of 10× assay buffer (500 mM Tris pH 7.5, 83 mM $MgCl_2$, 17 mM EGTA), and 40 microliters 1 μCi/μL [3H]-cAMP. SPA beads solution was prepared by adding 500 mg to 28 ml $H_2O$ for a final concentration of 20 mg/ml beads and 18 mM zinc sulphate.

The results are shown in Table 1.

TABLE 1

| Example | $IC_{50}$ PDE4 (nM) |
|---|---|
| 1 | 7.7 |
| 2 | 3.1 |
| 8 | 2 |
| 13 | 9.3 |
| 23 | 9.5 |
| 31 | 20 |
| 36 | 13 |
| 39 | 16 |
| 45 | 7.8 |
| 46 | 8.9 |
| 50 | 14 |
| 52 | 12 |
| 72 | 6.0 |
| 86 | 14 |
| 88 | 6.1 |
| 91 | 5.9 |
| 92 | 8.7 |
| 97 | 0.5 |
| 109 | 0.26 |
| 120 | 7.1 |
| 176 | 19 |
| 181 | 25 |
| 190 | 9.3 |
| 231 | 20 |
| 232 | 13 |
| 263 | 15 |
| 264 | 11 |
| 274 | 5.5 |

The results in table 1 show that the compounds of formula (I) are potent inhibitors of phosphodiesterase 4 (PDE 4). Preferred pyridazin-3(2H)-one derivatives of the invention possess an $IC_{50}$ value for the inhibition of PDE4 (determined as defined above) of less than 100 nM, preferably less than 50 nM and most preferably less than 20 nM. The compounds are also capable of blocking the production of some pro-inflammatory cytokines such as, for example, TNFα.

Thus, they can be used in the treatment of allergic, inflammatory and immunological diseases, as well as those diseases or conditions where the selective inhibition of PDE4 and the blockade of pro-inflammatory cytokines is known to be of benefit. These disease states include (see, for example, U.S. Pat. No. 5,449,686, U.S. Pat. No. 5,710,170, WO 98/45268, WO 99/06404, WO 01/57025, WO 01/57036, WO 01/46184, WO 97105105, WO 96/40636, U.S. Pat. No. 5,786,354, U.S. Pat. No. 5,773,467, U.S. Pat. No. 5,753,666, U.S. Pat. No. 5,728,712, U.S. Pat. No. 5,693,659, U.S. Pat. No. 5,679,696, U.S. Pat. No. 5,596,013, U.S. Pat. No. 5,541,219, U.S. Pat. No. 5,508,300, U.S. Pat. No. 5,502,072 or H. J. Dyke and J. G. Montana, *Exp. Opin. Invest. Drugs* 1999, 8,1301-1325) asthma, chronic obstructive pulmonary disease, allergic rhinitis, rheumatoid arthritis, osteoarthritis, osteoporosis, bone-formation disorders, glomerulonephritis, multiple sclerosis, ankylosing spondylitis, Graves ophtalmopathy, myasthenia gravis, diabetes insipidus, graft rejection, gastrointestinal disorders such as ulcerative colitis or Crohn disease, septic shock, adult distress respiratory syndrome, and skin diseases such as atopic dermatitis, contact dermatitis, acute dermatomyositis and psoriasis. They can also be used as improvers of cerebrovascular function as well as in the treatment of other CNS related diseases such as dementia, Alzheimer's disease, depression, and as nootropic agents.

The PDE4 inhibitors of the invention are also of benefit when administered in combination with other drugs such as steroids and immunosuppressive agents, such as cyclosporin A, rapamycin or T-cell receptor blockers. In this case the administration of the compounds allows a reduction of the dosage of the other drugs, thus preventing the appearance of the undesired side effects associated with both steroids and immunosuppressants.

Like other PDE4 inhibitors (see references above) the compounds of the invention can also be used for blocking the ulcerogenic effects induced by a variety of etiological agents, such as antiinflammatory drugs (steroidal or non-steroidal antiinflammatory agents), stress, ammonia, ethanol and concentrated acids. They can be used alone or in combination with antacids and/or antisecretory drugs in the preventive and/or curative treatment of gastrointestinal pathologies like drug-induced ulcers, peptic ulcers, H. Pylori-related ulcers, esophagitis and gastro-esophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, another embodiment of he invention is the use of the pyridazin-3(2H)-one derivatives of formula (I) in the manufacture of a medicament for the treatment of pathological conditions or diseases susceptible to amelioration by inhibition of phosphodiesterase 4 (PDE4), as well as a method for treating a subject afflicted with a pathological condition or disease susceptible to amelioration by inhibition of PDE4, which comprises administering to said subject an effective amount of a compound of formula (I).

The present invention also provides pharmaceutical compositions which comprise, as an active ingredient, at least a pyridazin-3(2M)-one derivative of formula (I) or a pharmaceutically acceptable salt thereof in association with a pharmaceutically acceptable excipient such as a carrier or diluent.

The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent and a flavouring agent Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 10-600 mg of active ingredient per day. Daily dosage may be administered in one or more treatments, preferably from 1 to 4 treatments, per day.

The present invention will be further illustrated by the following examples. The examples are given by way of illustration only and are not to be construed as a limiting.

$^1$H Nuclear Magnetic Resonance Spectra were recorded on a Varian Gemini 300 spectrometer. Low Resolution Mass Spectra (m/z) were recorded on a Micromass ZMD mass spectrometer using ESI ionization. Melting points were recorded using a Perkin Elmer DSC-7 apparatus. The chromatographic separations were obtained using a Waters 2690 system equipped with a Symmetry C18 (2.1×10 mm, 3.5 mM) column. The mobile phase was formic acid (0.4 ml), ammonia (0.1 ml), methanol (500 ml) and acetonitrile (500 ml) (B) and formic acid (0.46 ml), ammonia (0.115 ml) and water (1000 ml) (A): initially from 0% to 95% of B in 20 min, and then 4 min. with 95% of B. The reequilibration time between two injections was 5 min. The flow rate was 0.4 ml/min. The injection volume was 5 microliter. Diode array chromatograms were collected at 210 nM.

PREPARATION EXAMPLES

Preparation 1

1-[3-(Cyclopentyloxy)-4-methoxyphenyl]butane-1,3dione

To a stirred suspension of 60% sodium hydride (200 mg, 5 mmol) and ethyl acetate (0.49 ml, 5 mmol) in tetrahydrofuran (25 ml) were sequentially added a solution of 1-[3-(cyclopentyloxy)-4-methoxyphenyl]ethanone (European Patent Application EP470805) (590 mg, 2.5 mmol) in tetrahydrofuran (5 ml), two drops of ethanol and a solution of dibenzo-18-crown (15 mg, 0.04 mmol) in tetrahydrofuran (5 ml). The reaction mixture was refluxed for 5 h, allowed to cool to room temperature and finally quenched with aqueous 10% sulphuric acid solution (5 ml). The resulting mixture was diluted with diethyl ether, washed with saturated ammonium chloride solution, dried and concentrated under reduced pressure to yield a crude product which was purified by column chromatography (SiO2, hexane-ethyl acetate 4:1) to afford the title compound (610 mg, 86% yield) as a pale yellow oil.

$\delta(CDCl_3)$: 1.62 (m, 2H), 1.85 (m, 6H), 2.16 (s, 3H), 3.98 (s, 3H), 4.82 (m, 1H), 6.10 (s, 1H), 6.85 (d, 1H), 7.42 (m, 2H).

Preparation 2

Ethyl 5-methyl[l4-(methylthio)benzoyl]isoxazole-3-carboxylate

To an ice-cooled solution of sodium ethoxide (3.2 g, 59 mmol) in absolute ethanol (125 ml) was added portionwise 1-[4-(methylthio)phenyl]butane-1,3-dione (Goerlitz, G., Hartmann, H. *Heteroat. Chem.*, 1997, 8, 147-55) (11.2 g, 54 mmol) and the mixture was stirred at 0° for 30 min. A solution of ethyl chloro(hydroximino)acetate (9.0 g, 59 mol) in absolute ethanol (25 ml) was added dropwise and the final mixture was stirred at room temperature overnight. The resulting mixture was acidified with acetic acid to pH 5-6 and concentrated. The residue thus obtained was partitioned between ethyl acetate and water, washed with brine, dried and concentrated under reduced pressure to yield the title compound (13.0 g, 70% yield) as a yellow solid.

$\delta(CDCl_3)$: 1.02 (t, 3H), 2.56 (s, 6H), 4.07 (q, 2H), 7.42 (d, 2H), 7.65 (d, 2H).

Preparation 3

Ethyl 4-[3-(cyclopentyloxy)-4methoxybenzoyl]-5-methylisoxazole-3-carboxylate

Obtained as a yellow solid (91%) from 1-[3-(cyclopentyloxy)-4-methoxyphenyl]butane-1,3-dione (Preparation 1) and ethyl chloro(hydroximino)acetate following the experimental procedure described in Preparation 2.

$\delta(CDCl_3)$: 1.02 (t, 3H),1.61 (m, 4H), 1.85 (m, 4H), 2.56 (s, 3H), 3.98 (s, 3H), 4.07 (q, 2H), 4.82 (m,1H), 6.85 (d,1H), 7.23 (d, 1H), 7.42 (s, 1H).

Preparation 4

Ethyl 4-(4-fluorobenzoyl)-5-methylisoxazole-3-carboxylate

Obtained (95%) from 1-(4-fluorophenyl)butane-1,3-dione (Joshi, K. C.; Pathak, V. N.; Garg, U. *J. Indian Chem. Soc.* 1983, 60, 1074-1076) and ethyl chloro(hydroximino)acetate following the experimental procedure described in Preparation 2.

$\delta(CDCl_3)$: 1.1 (t, 3H), 2.50 (s, 3H), 4.20 (q, 2H), 7.20 (m, 2H), 7.80 (m, 2H).

Preparation 5

Ethyl 4-(3-fluorobenzoyl)-5-methylisoxazole-3-carboxylate

Obtained (79%) from 1-(3-fluorophenyl)butane-1,3-dione (Joshi, K. C.; Pathak, V. N.; Garg, U. *J. Indian Chem. Soc.* 1983, 60, 1074-1076) and ethyl chloro(hydroximino)acetate following the experimental procedure described in Preparation 2.

$\delta(CDCl_3)$: 1.10 (t, 3H), 2.60 (s, 3H), 4.15 (q, 2H), 7.30 (m, 4H).

Preparation 6

Ethyl 4-benzoyl-5-propylisoxazole-3-carboxylate

Obtained (70%) from 1-phenylhexane1,3-dione (Levine et al. *J. Amer. Chem. Soc.* 1945, 67, 1510) and ethyl chloro(hydroximino)acetate following the experimental procedure described in Preparation 2.

$\delta(CDCl_3)$: 1.00 (t, 6H), 1.80 (m, 2H), 2.90 (t, 2H), 4.10 (q. 2H), 7.50 (m, 5H).

Preparation 7

3-Methyl4-[4-(methylthio)phenyl]isoxazolo[3,4-d]pyridazin-7(6H)-one

Hydrazine monohydrate (1.70 g, 35 mmol) was added dropwise to a solution of the title compound of Preparation 2 (7.11 g, 23 mmol) in dry ethanol (500 ml) and the resulting mixture was stirred overnight After cooling with an ice bath, a precipitate was formed which was collected by filtration and washed with diethyl ether to yield the title compound (3.31 g, 53% yield) as a yellow solid.

$\delta(CDCl_3)$: 2.57 (s, 3H), 2.58 (s, 3H), 7.25 (d, 2H), 7.42 (d, 2H), 11.35 (bs, 1H).

Preparation 8

4-[3-(Cyclopentyloxy)-4-methoxyphenyl]-3-methylisoxazolo[3,4-d]pyridazin-7(6H)-one Obtained as a yellow solid (93%) from the title compound of Preparation 3 using the experimental procedure described in Preparation 7.

$\delta(CDCl_3)$: 1.61-2.01 (m, 8H), 2.56 (s, 3H), 3.98 (s, 3H), 4.83 (m, 1H), 7.03 (m, 3H), 9.62 (bs, 1H).

Preparation 9

4-(4-Fluorophenyl)-3-methylisoxazolo[3,4-d]pyridazin-7(6H)-one

Obtained (87%) from the title compound of Preparation 4, using the experimental procedure described in Preparation 7.

$\delta(CDCl_3)$: 2.55 (s, 3H), 7.30 (m, 2H), 7.60 (m,2H).

Preparation 10

4-(3-Fluorophenyl)-3-methylisoxazolo[3,4-d]pyridazin-7(6H)-one

Obtained (81%) from the title compound of Preparation 5, following the experimental procedure described in Preparation 7.

δ(CDCl$_3$): 2.60 (s, 3H), 7.3 (m, 4H), 9.90 (s, 1H).

Preparation 11

4-Phenyl-3-propylisoxazolo[3,4-d]pyridazin-7(6H)-one

Obtained (40%) from the title compound of Preparation 6 following the experimental procedure described in Preparation 7.

δ(CDCl$_3$): 0.90 (t, 3H), 1.80 (m, 2H), 2.80 (t, 2H), 7.50 (m, 5H), 10.0 (s, 1H).

Preparation 12

6-Ethyl-3-methyl-4-[4-(methylthio)phenyl]isoxazolo[3,4-d]pyridazin-7(6H)-one Cesium carbonate (17.2 g, 53 mmol) was added to a solution of the title compound of Preparation 7 (2.4 g, 8.8 mmol) in dry dimethylformamide (30 ml) and the resulting suspension was stirred for 15 minutes. Then ethyl bromide (4.6 ml, 62 mmol) was added dropwise and the final mixture was stirred at room temperature overnight and then at 50° C. for 5 h. The mixture was concentrated and the residue thus obtained was suspended in ethyl acetate, washed with water and brine, dried and concentrated to yield the title compound (1.44 g, 54% yield) as a yellow solid.

δ(CDCl$_3$): 1.38 (t, 3H), 2.57 (s, 3H), 2.58 (s, 3H), 4.23 (q, 2H), 7.35 (d, 2H), 7.48 (d, 2H).

Preparation 13

6-Ethyl-4-[4-(methylthio)phenyl]-3-propylisoxazolo[3,4-d]pyridazin-7(6H)-one To a stirred solution of the title compound of Preparation 7 (1.5 g, 5.4 mmol) in dry dimethylformamide (10 ml) was added a solution of sodium hydroxyde (0.43 g, 10.8 mmol) in dry dimethylformamide (5 ml) and the resulting mixture was stirred for 15 minutes. Then ethyl bromide (1.21 ml, 16.2 mmol) was added dropwise and the final mixture was stirred at room temperature for 2 h, poured onto dichloromethane and washed with water and brine. The organic layer was dried and the solvent removed to yield a crude product that was purified by flash column chromatography (SiO$_2$, hexane-ethyl ether 4:1) to afford the title compound (0.20 g, 12% yield).

δ(CDCl$_3$): 0.82 (t, 3H), 1.39 (t, 3H), 1.68(m, 2H), 2.57 (s, 3H), 2.82 (t, 2H), 4.23 (q, 2H), 7.35 (d, 2H), 7.42 (d, 2H).

Preparation 14

6-Ethyl-3-(1-ethylpropyl)-4-[4-(methylthio)phenyl]isoxazolo[3,4-d]pyridazin-7(6H)-one Obtained as a subproduct (7%) in Preparation 13.

δ(CDCl$_3$): 0.62 (t; 6H), 1.39 (t, 3H), 1.75(m, 4H), 2.59 (s, 3H), 2.78 (m, 1H), 4.24 (q, 2H), 7.38 (m, 4H).

Preparation 15

6-Ethyl-3-methyl-4-[4(methylsulphinyl)phenyl]isoxazoio[3,4-d]pyridazin-7(6H)-one To an ice cooled stirred solution of the title compound of Preparation 12 (1.0 g, 3.32 mmol) in methanol (8 ml) was added dropwise a solution of sodium periodate (0.71 g, 3.35 mmol) in water (8 ml). The resulting mixture was stirred at 0° C. for 2 h and then at room temperature overnight. The solvent was removed and the resulting slurry was suspended in water and extracted with ethyl acetate. The organic layer was dried and the solvent removed to yield the title product (0.70 g, 66%) as a pale yellow solid.

δ(CDCl$_3$): 1.42 (t, 3H), 2.57 (s, 3H), 2.81 (s, 3H), 4.30 (q, 2H), 7.75 (d, 2H), 7.85 (d, 2H).

Preparation 16

4-[3-(Cyclopentyloxy)-4-methoxyphenyl]-6-ethyl-3-methylisoxazolo[3,4-d]pyridazin-7(6H)-one Obtained (38%) from the title compound of Preparation 8 following the experimental procedure described in Preparation 12.

δ(CDCl$_3$): 1.42 (t, 3H), 1.61 (m, 2H); 1.91 (m, 6H), 2.58 (s, 3H), 3.98 (s, 3H), 4.17 (q, 2H), 4.83 (m, 1H), 7.03 (m, 3H).

Preparation 17

6-Ethyl-4-(4-fluorophenyl)-3-methylisoxazolo[3,4-d]pyridazin-7(6H)-one

To a suspension of the title compound of Preparation 9 (0.49 g, 2.0 mmol) and anhydrous potassium carbonate (0.55 g, 4.0 mmol) in dry dimethylformamide (5.3 ml) was added ethyl bromide (0.44 g, 4.0 mmol) and the resulting mixture heated at 110° C. for 40 minutes. Then ice-water was added (30 ml) and the resulting precipitate collected by filtration to afford the title compound (0.47 g, 86%) as a yellow solid.

δ(CDCl$_3$): 1.40 (t, 3H), 2.58 (s, 3H), 4.23 (q, 2H), 7.20 (m,2H), 7.58 (m,2H).

Preparation 18

6-Ethyl-4(3-fluorophenyl)-3-methylisoxazolo[3,4-d]pyridazin-7(6H)-one

Obtained (84%) from the title compound from Preparation 10 following the experimental procedure described in Preparation 17.

δ(CDCl$_3$): 1.40 (t, 3H), 2.58 (s, 3H), 4.30 (q, 2H), 7.30 (m, 3H), 7.50 (m, 1H).

Preparation 19

6-Ethyl-4-phenyl-3-propylisoxazolo[3,4-d]pyridazin-7(6H)-one

Obtained (90%) from the title compound from Preparation 11 following the experimental procedure described in Preparation 17.

δ(CDCl$_3$): 0.90 (t, 3H), 1.50 (t, 3H), 1.80 (m, 2H), 2.80 (m, 2H), 4.25 (m, 2H), 7.50 (s, 5H).

Preparation 20

6-(Cyclopropylmethyl)-3-methyl-4-phenylisoxazolo[3,4-d]pyridazin-7(6H)-one

Obtained as a light brown solid (70%) from 3-methyl-4-phenylisoxazolo[3,4-d]pyridazin-7(6H)-one (Renzi, G.; Pinzauti, S., *Il Farmnaco Ed. Sci.* 1969, 24, 885-889) and cyclopropylmethyl bromide following the experimental procedure described in Preparation 17.

$\delta(CDCl_3)$: 0.42 (m, 4H), 1.38 (m, 1H), 2.55 (s, 3H), 4.08 (d, 2H), 7.61 (m, 5H).

Preparation 21

3-Methyl-4-phenyl-6-(pyridin-4-ylmethyl)isoxazolo[3,4-d]pyridazin-7(6H)-one To a stirred suspension of 3-methyl-4-phenylisoxazolo[3,4-d]pyridazin-7(6H)-one (1.5 g, 6.6 mmol) (Renzi, G.; Pinzauti, S., *Il Farmaco Ed. Sci.* 1969, 24, 885-889), 60% sodium hydride (0.63 g, 15.8 mmol) was added portionwise and the mixture stirred for 15 minutes. Then 4-(chloromethyl) pyridine hydrochloride (1.3 g, 7.9 mmol) was added portionwise and the final mixture was stirred at 50° C. for 7 h, then poured onto water and extracted with ethyl acetate. The organic layer was washed with brine, dried and concentrated in vacuo to yield a crude product that was crystallized from isopropyl ether/petroleum ether to yield the title compound (1.66 g, 79% yield) as a light brown solid.

$\delta(CDCl_3)$: 2.55 (s, 3H), 5.38 (s, 2H), 7.38 (d, 2H), 7.57 (m, 5H), 8.58 (m, 2H).

Preparation 22

5-Acetyl-4-amino-2-ethyl-6-phenylpyridazin-3(2H)-one

A mixture of 6-ethyl-3-methyl-4-phenylisoxazolo[3,4-d]pyridazin-7(6H)-one (Dal Piaz, V et al, *J. Med. Chem.* 1997, 40, 1417) (2.0 g, 7.83 mmol) and, 10% palladium on charcoal (400 mg) in ethanol (400 ml) was shaken under hydrogen at room temperature and 2 bar for 3 h. The catalyst was filtered off and the solvent was removed under reduced pressure to yield the title compound (1.97 g, 98% yield).

m.p. 150.8-152.7° C. $\delta(CDCl_3)$: 1.43 (t, 3H), 1.67 (bs, 2H), 1.78 (s, 3H), 4.26 (q, 2H), 7.45 (s, 5H).

Preparation 23

5-Acetyl-4-amino-2-ethyl-6-[4-(methylthio)phenyl]pyridazin-3(2H)-one

A mixture of the title compound of Preparation 12 (0.5 g, 1.66 mmol), 10% palladium on charcoal (106 mg) and ammonium formate (2.3 g, 39 mmol) in ethanol (20 ml) was refluxed overnight. An extra amount of catalyst (213 mg) was added and the mixture was refluxed for another 24 h. Finally, the catalyst was filtered off and the solvent was removed under reduced pressure. The resulting residue was purified by flash column chromatography ($SiO_2$, dichloromethane) to yield the title compound (190 mg, 37%).

$\delta(CDCl_3)$: 1.42 (t, 3H), 1.81 (s, 3H), 2.50 (s, 3H), 4.24 (q, 2H), 7.35 (m, 4H).

Preparation 24

4-Amino-5-butyryl-2-ethyl-6-[4-(methylthio)phenyl]pyridazin-3(2H)-one

Obtained (27%) from the title product of Preparation 13 following the procedure described in Preparation 23.

$\delta(CDCl_3)$: 0.65 (t, 3H), 1.39 (m, 5H), 2.02 (t, 2H), 2.50(s, 3H), 4.23 (q, 2H), 7.12 (bs, 2H), 7.35 (m, 4H).

Preparation 25

4-Amino-2-ethyl-5-(2-ethylbutanoyl)-6-[4-(methylthio)phenyl]pyridazin-3(2H)-one Obtained (56%) from the title product of Preparation 14 following the procedure described in Preparation 23.

$\delta(CDCl_3)$: 0.52 (t, 6H), 1.35 (m, 7H), 2.10 (m, 1H), 2.51 (s, 3H), 4.24 (q, 2H), 7.01 (bs, 2H), 7.38 (m, 4H).

Preparation 26

5-Acetyl-4-amino-2-ethyl-6-[4-(methylsulphinyl)phenyl]pyridazin-3(2H)-one

Obtained (70%) from the title product of Preparation 15 following the procedure described in Preparation 23.

$\delta(CDCl_3)$: 1.41 (t, 3H), 1.80 (s, 3H), 2.77 (s, 3H), 4.30 (q, 2H), 7.65 (d, 2H), 7.77 (d, 2H).

Preparation 27

5-Acetyl-4-amino-6-(3-cyclopentyloxy-4methoxyphenyl)-2-ethylpyridazin-3(2H)-one Obtained (40%) from the title product of Preparation 16 following the procedure described in Preparation 23.

$\delta(CDCl_3)$: 1.42 (t, 3H), 1.61-2.01 (m, 11H), 3.98 (s, 3H), 4.23 (q, 2H), 4.83 (m, 1H), 6.98 (m, 3H), 7.32 (bs, 2H).

Preparation 28

5-Acetyl-4-amino-2-benzyl-6-phenylpyridazin-3(2H)-one

Obtained (92%) from 6-benzyl-3-methyl-4-phenylisoxazolo[3,4-d]pyridazin-7(6H)-one (Dal Piaz, V.; Ciciani, G.; Giovannoni, M P, *Farmaco,* 1991, 46, 435-47) following the procedure described in Preparation 23.

$\delta(CDCl_3)$: 1.78 (s, 3H), 5.38 (s, 2H), 7.21-7.55 (m, 10H).

Preparation 29

5-Acetyl-4-amino-2-(cyclopropylmethyl)-6-phenylpyridazin-3(2H)-one

Obtained (90%) from the title compound of Preparation 20 following the procedure described in Preparation 23.

$\delta(CDCl_3)$: 0.51 (m, 4H), 1.40 (m, 1H), 1.78 (s, 3H), 4.02 (d, 2H), 7.43 (m, 5H).

Preparation 30

5-Acetyl-4-amino-6-phenyl-2-(pyridin-4-ylmethyl)pyridazin-3(2H)-one

Obtained (85%) from the title compound of Preparation 21 following the procedure described in Preparation 23.

δ(CDCl$_3$): 1.77 (s, 3H), 5.36 (s, 2H), 7.27 (d, 2H), 7.43 (m, 5H), 8.59 (d, 2H).

Preparation 31

5-Acetyl-2-ethyl-6-(4-fluorophenyl)-4-nitropyridazin-3(2H)-one

To a stirred suspension of the title compound of Preparation 17 (0.5 g, 1.83 mmol) in a mixture of acetic acid (7.3 ml), water (7.3 ml) and nitric acid (2.5 ml), cerium ammonium nitrate (6.0 g, 11 mmol) was added portionwise during 40 min. Addition of ice-cold water gave a crude precipitate which was filtered and washed with cold water to yield the title product (45% yield).

δ(CDCl$_3$): 1.43 (t, 3H), 2.20 (s, 3H), 4.40 (q, 2H), 7.20 (m, 2H), 7.48 (m, 2H).

Preparation 32

5-Acetyl-2-ethyl-6-(3-fluorophenyl)-4-nitropyridazin-3(2H)-one

Obtained (40%) from the title product of Preparation 18 following the experimental procedure described in Preparation 31.

δ(CDCl$_3$): 1.50 (t, 3H), 2.20 (s, 3H), 4.40 (q, 2H), 7.20 (m, 3H), 7.46 (m, 1H).

Preparation 33

5-Butyryl-2-ethyl-4-nitro-6-phenylpyridazin-3(2H)-one

Obtained (51%) from the title compound of Preparation 19 following the experimental procedure described in Preparation 31.

δ(CDCl$_3$): 0.90 (t. 3H), 1.50 (m, 5H), 2.35 (m, 2H), 4.40 (q, 2H), 7.50 (m, 5H).

Preparation 34

6-Ethyl-3,4-diphenylisoxazolo[3,4-d]pyridazin-7(6H)-one

Obtained as solid (91%), from 3,4-diphenylisoxazolo[3,4-d]pyridazin-7(6H)-one (Renzi, G.; Dal Piaz, Gazz. *Chim. It.* 1965, 95, 147-891) and ethyl bromide following the experimental procedure described in Preparation 17.

δ(CDCl$_3$): 1.40 (t, 3H), 4.38 (q, 2H), 7.35 (m, 10H).

Preparation 35

4-Amino-5-benzoyl-2-ethyl-6-phenylpyridazin-3(2H)-one

Obtained (90%) from the title product of Preparation 34 following the procedure described in Preparation 22.

δ(CDCl$_3$): 1.43(t, 3H), 4.38 (q, 2H), 6.88 (s, 2H), 7.10 (m, 4H), 7.24 (m, 3H), 7.43 (m, 3H).

Preparation 36

5-Amino-1-ethyl-6-oxo-3-phenyl-1,6-dihydropyridazine-4-carbaldehyde

A mixture of 5-amino-6-oxo-3-phenyl-1,6-dihydropyridazine-4-carbaldehyde one (Dal Piaz, V., Ciciani, G, Giovannoni, M. P., *Heterocycles,* 1991, 32, 1173-9) (258 mg, 1.2 mmol), ethyl bromide (294 mg, 2.7 mmol) and anhydrous potassium carbonate (240 mg, 2.4 mmol) in anhydrous DMF (5 mL) was stirred at 90° C. for 2 h. Cold water (25 ml) was added and the precipitate was collected by filtration to yield the title product (88%).

δ(CDCl$_3$): 1.43 (t, 3H), 4.27 (m, 2H), 6.95 (s, 2H), 7.48 (m, 5H), 9.75 (s, 1H).

Preparation 37

Ethyl 4-benzoyl-5-hydroxyisoxazole-3-carboxylate

To a cooled and stirred solution of sodium ethoxide, obtained from sodium (2.3 g, 0.1 mol) and anhydrous EtOH (60 ml), a solution of ethyl benzoylacetate (9.6 g, 0.05 mol) in the same solvent (5 ml) was slowly added. A solution of ethylcloro(hydroximino)acetate (7.55 g, 0.05 mol) in anhydrous EtOH (10 ml) was added in a dropwise manner (over 1 h period). The mixture was neutralized with 6N HCl and the alcoholic layer was evaporated. After dilution with cold water (150-200 mL), the suspension was extracted with ethyl ether and the aqueous layer was acidified with 6N HCl to afford the product which was recovered by filtration (45% yield).

δ(DMSO-d6): 1.25 (t, 3H), 4.15 (q, 2H), 7.50 (m, 3H), 7.80 (m, 2H), 10.80 (s, 1H).

Preparation 38

Methyl 5-amino-6-oxo-3-phenyl-1,6-dihydropyridazine-4-carboxylate

A mixture of the title compound of preparation 37 (200 mg, 0.76 mmol), hydrazine hydrate (165 mg, 3.3 mmol), PPA (12 g) and 12 mL anhydrous EtOH is stirred at 40° for 12 h. After dilution with water (40 ml) the crude precipitate was recovered by suction. Then it was suspended in 2 mL of EtOH and ammonium formate (75 mg, 1.2 mmol) and 10% Pd/C (15 mg) were added. The mixture was refluxed for 1 h. Filtration and evaporation of the solvent yielded a product that was solved in anhydrous DMF (1.7 mL). Anhydrous potassium carbonate (50 mg, 0.5 mmol) and iodomethane (200 mg, 1.4 mmol) were added and the mixture was stirred at room temperature for 45 min. Cold water (20 ml) was then added and the title compound was collected by filtration (50% yield).

δ(CDCl3): 3.49 (s, 3H), 7.02 (s, 2H), 7.38 (s, 5H).

Preparation 39

Methyl 5-amino-1-ethyl-6-oxo-3-phenyl-1,6-dihydropyridazine-4-carboxylate

To a mixture of the title compound of preparation 38 (122 mg, 0.5 mmol) and anhydrous potassium carbonate (140 mg, 1.4 mmol) in anhydrous DMF (1.4 mL) ethyl bromide (0.1 mL, 1.2 mmol) was added and it was refluxed under stirring for 1 h. The suspension was then diluted with cold water and the title product was collected by filtration (75% yield).

δ(CDCl$_3$): 1.41 (t, 3H), 3.48 (s, 3H), 4.25 (q, 2H), 7.00 (s, 2H), 7.38 (s, 5H).

Preparation 40

6-Ethyl-4-phenyl-3-styryl-6H-isoxazolo[3,4-d]pyridazin-7-one

To a freshly prepared solution of sodium methoxide (108 mg, 1.96 mmol) in methanol (2 mL), a solution of 6-ethyl-3-methylphenyl-6H-isoxazolo[3,4-d]pyridazin-7-one (500 mg, 1.96 mmol) (Dal Piaz, V.; Giovannoni, M. P.; Castellana, C.; et al., *J. Med. Chem.* 1997, 40, 1417-1421) in 2 mL of dry methanol was added and the mixture was stirred for a while. Then, benzaldehyde (0.40 mL, 3.92 mmol) was added dropwise and the final mixture was refluxed for 2 hours. The resulting suspension was let to cool down and the final product (514 mg, 76% yield) was collected by filtration.

$\delta$(CDCl$_3$): 1.40 (t, 3H), 4.31 (q, 2H), 6.80. (d, 1H), 7.35 (m, 5H), 7.68 (m, 6H).

Preparation 41

6-Ethyl-4-phenyl-3-(2-thiophen-3-yl-vinyl)-6H-isoxazolo[3,4-d]pyridazin-7-one Obtained (75%) from 6-ethyl-3-methyl-4-phenyl-6H-isoxazolo[3,4-d]pyridazin-7one (500 mg, 1.96 mmol) (Dal Piaz, V.; Giovannoni, M. P.; Castellana, C.; et al , *J. Med. Chem.* 1997, 40, 1417-1421) and thiophene-3-carbaldehyde following the procedure described in Preparation 40.

$\delta$(CDCl$_3$): 1.42 (t, 3H), 4.30 (q, 2H), 6.58 (d, 1H), 6.98 (d, 1H), 7.28 (m,$_1$H), 7.42 (m, 1H), 7.63 (m, 6H).

Preparation 42

6-Ethyl-4-phenyl-3-(2-pyridin-3-yl-vinyl)-6H-isoxazolo[3,4-d]pyridazin-7-one Obtained (70%) from 6-ethyl-3-methyl-4-phenyl6H-isoxazolo[3,4-d]pyridazin-7-one (500 mg, 1.96 mmol) (Dal Piaz, V.; Giovannoni, M. P.; Castellana, C.; et al, , J. Med. Chem. 1997, 40, 1417-1421) and pyridine-3-carbaldehyde following the procedure described in Preparation 40.

$\delta$(CDCl$_3$): 1.41 (t, 3H), 4.30 (q, 2H), 6.80 (s, 11H), 6.88 (s, 1H), 7.50-7.66 (m, 7H), 8.60 (s, 2H).

Preparation 43

4-Amino-2-ethyl-6-phenyl-5-(3-phenylpropionyl)pyridazin-3(2H)-one

A mixture of the title compound of preparation 40 (514 mg, 1.50 mmol) and 10% palladium on charcoal (100 mg) in ethanol (100 ml) was shaken under hydrogen at room temperature and 2 bar overnight. The catalyst was filtered off and the solvent was removed under reduced pressure to yield the title compound (487 mg, 95% yield).

m.p. 115.1-116.1° C. $\delta$(CDCl$_3$): 1.40 (t, 3H), 2.28 (t, 2H), 2.68 (t, 2H), 4.25 (q, 2H), 6.78 (m, 2H), 7.05 (m, 3H), 7.45 (m, 5H).

Preparation 44

4-Amino-2-ethyl-6-phenyl-5-(3-thien-3-ylpropanoyl)pyridazin-3(2H)-one

Obtained (67%) from the title, compound of Preparation 41 following the procedure described in Preparation 43.

$\delta$(CDCl$_3$): 1.41 (t, 3H), 2.30 (t, 2H), 2.70 (t, 2H), 4.25 (q, 2H), 6:08 (d, 1H), 6.54-6.62 (m, 2H), 7.08-7,58 (m, 7H).

Preparation 45

4-Amino-2-ethyl-6-phenyl-5-(3-pyridin-3-yl-propanoyl)pyridazin-3(2H)-one

Obtained (97%) from the title compound of Preparation 42 following the procedure described in Preparation 43.

$\delta$(CDCl$_3$): 1.41 (t, 3H), 2.29 (t, 2H), 2.70 (t, 2H), 4.25 (q, 2H), 7.05-7.57 (m, 9H).

Preparation 46

6-Isopropyl-3-methyl-4-phenyl-6H-isoxazolo[3,4-d]pyridazin-7-one

To a stirred solution of 3-methylphenylisoxazolo[3,4-d]pyridazin-7(6H)-one (0.5 g, 2.2 mmol) (Renzi, G.; Pinzauti, S., *II Farmaco Ed. Sci.* 1969, 24, 885-889), triphenylphosphine (0.577 g, 2.2 mmol) and isopropanol (0.170 mL, 2.2 mmol)in 7 mL of dry THF, diethylazadicarboxylate (0.345 mL, 2.2 eq) was added dropwise and the resulting mixture was stirred at room temperature overnight. Then, solvent was removed and the crude product was purified by flash column chromatography (SiO$_2$, hexane-ethyl acetate) to yield the title product (374 mg, 63% yield).

$\delta$(CDCl$_3$): 1.42 (d, 6H), 2.58 (s, 3H), 5.40 (m, 1H), 7.55 (m, 5H).

Preparation 47

5-Acetyl-4-amino-2-isopropyl-6-phenylpyridazin-3(2H)-one

Obtained (92%) from the title product of Preparation 46 following the procedure described in Preparation 23.

$\delta$(CDCl$_3$): 1.40 (d, 6H), 1.78 (s, 3H), 5.32 (m, 1H), 7.45 (m, 5H).

Preparation 48

6-(2-Hydroxyethyl)-3-methyl-4-phenyl-6H-isoxazolo[3,4-d]dipyridazin-7-one

Obtained as a solid (98%) from 3-methyl-4-phenylisoxazolo[3,4-d]pyridazin-7(6H)-one (Renzi, G.; Pinzauti, S., *II Farmaco Ed. Sci.* 1969, 24, 885-889) and 2-bromoethanol following the experimental procedure described in Preparation 17. The mixture was stirred at 50° C. for 5 h and the product was isolated by pouring the reaction mixture onto water and extracting with ethyl acetate.

$\delta$(DMSO-d$_6$): 2.57 (s, 3H), 3.75 (q, 2H), 4.18 (t, 2H), 4.83 (t, 1H)7.18 (m, 3H), 7.25 (m, 2H).

Preparation 49

5-Acetyl-4-amino-2-(2-hydroxyethyl)-6-phenylpyridazin-3(2H)-one

Obtained as a solid (99%) from the title compound of Preparation 48 following the procedure described in preparation 22.

$\delta$(DMSO-d$_6$): 1.78 (s, 3H), 3.72 (t, 2H), 4.18 (t, 2H), 7.40 (m, 5H), 7.78 (bs, 2H).

Preparation 50

4-(3-Fluorophenyl)-6-2-hydroxyethyl)-3-methyl-6H-isoxazolo[3,4-d]pyridazin-7-one Obtained as a solid (75%) from the title compound of Preparation 10 and 2-bromoethanol following the experimental procedure described in Preparation 17. The mixture was stirred at room temperature overnight and the product was isolated by pouring the reaction mixture onto water and extracting with ethyl ether.
LRMS: m/Z 290 (M+1)$^+$

Preparation 51

5-Acetyl-4-amino-6-(3-fluorophenyl)-2-(2-hydroxyethyl)-2H-pyridazin-3-one

Obtained as a solid (86%) from the title compound of Preparation 50 following the procedure described in Preparation 22.
LRMS: m/Z 292 (M+1)$^+$

Preparation 52

4-(3-Chlorophenyl)-6-(cyclopropylmethyl)-3-methylisoxazolo[3,4-d]pyridazin-7(6H)-one Obtained (67%) from 4-(3-chlorophenyl)-3-methyl-6H-isoxazolo[3,4-d]pyridazin-7-one (Dal Piaz, V et al, *J. Med. Chem.* 1997, 40, 1417) and cyclopropylmethyl bromide following the experimental procedure described in Preparation 17. The product was purified by column chromatography.
LRMS: m/z 316 (M+1)$^+$.

Preparation 53

5-Acetyl-6-(3-chlorophenyl)-2-(cyclopropylmethyl)-4-nitropyridazin-3(2H)-one Obtained (21%) from the title product of Preparation 52 following the experimental procedure described in Preparation 31. The product was purified by column chromatography.
LRMS: m/z 348 (M+1)$^+$.

Preparation 54

6-(Cyclopropylmethyl)-4-(3-fluorophenyl)-3-methylisoxazolo[3,4-d]pyridazin-7(6H)-one Obtained (37%) from the title compound from Preparation 10 and cyclopropylmethyl bromide following the experimental procedure described in Preparation 17. The product was purified by column chromatography.
$\delta$(CDCl$_3$): 0.52 (m, 4H), 1.38 (m, 1H), 2.58 (s, 3H), 4.07 (d, 2H), 7.30 (m, 3H), 7.55 (m, 1H).

Preparation 55

5-Acetyl-2-(cyclopropylmethyl)-6-(3-fluorophenyl)-4-nitropyridazin-3(2H)-one Obtained (23%) from the title product of Preparation 54 following the experimental procedure described in Preparation 31.
$\delta$(CDCl$_3$): 0.54 (m, 4H), 1.51 (m, 1H), 2.21 (s, 3H), 4.16 (d, 2H), 7.22 (m, 3H), 7.45 (m, 1H).

Preparation 56

4-(3-Fluorophenyl)-6-isopropyl-3-methylisoxazolo[3,4-d]pyridazin-7(6H)-one

Obtained (37%) from the title compound of Preparation 10 following the experimental procedure described in Preparation 46.
$\delta$(CDCl$_3$): 1.38 (d, 6H), 2.58. (s, 3H), 5.41 (m, 1H), 7.32 (m, 3H), 7.52 (m, 1H).

Preparation 57

5-Acetyl-6-(3-fluorophenyl)-2-isopropyl-4nitropyridazin-3(2H)-one

Obtained (40%) from the title product of Preparation 56 following the experimental procedure described in Preparation 31.
$\delta$(CDCl$_3$): 1.44 (d, 6H), 2.20 (s, 3H), 5.45 (m, 1H), 7.16 (m, 3H), 7.50 (m, 1H).

Preparation 58

6-(Cyclopropylmethyl)-4-(4-fluorophenyl)-3-methylisoxazolo[3,4-d]pyridazin-7(6H)-one Obtained (46%) from the title compound from Preparation 9 and cyclopropylmethyl bromide following the experimental procedure described in Preparation 17. The product was purified by column chromatography.
$\delta$(CDCl$_3$): 0.54 (m, 4H), 1.38 (m, 1H), 2.58 (s, 3H), 4.08 (d, 2H), 7.28 (d, 2H), 7.57 (dd, 2H).

Preparation 59

5-Acetyl-2-(cyclopropylmethyl)-6-(4-fluorophenyl)-4-nitropyridazin-3(2H)-one Obtained (37%) from the title product of Preparation 58 following the experimental procedure described in Preparation 31.
$\delta$(CDCl$_3$): 0.46 (m, 2H), 0.62 (m, 2H), 1.45 (m, 1H), 2.21 (s, 3H), 4.18 (d, 2H), 7.21 (m, 2H), 7.45 (m, 2H).

Preparation 60

5-Methyl-4-(naphthalene-1-carbonyl)isoxazole-3-carboxylic acid ethyl ester

Obtained as a solid (90%) from 1-naphthalen-1-yl-butane-1,3-dione (Banchetti et al; *Gazz. Chim. Ital.;* 1940, 70, 134-40) following the procedure of Preparation 2.
$\delta$(CDCl$_3$): 0.8 (t, 3H), 2.61 (s, 3H), 3.81 (q, 2H), 7.40-8.61 (m, 7H).

Preparation 61

3-Methyl-4-naphthalen-1-yl-6H-isoxazolo[3,4-d]pyridazin-7-one

Obtained as a solid (50%) from the title compound of Preparation 60 following the procedure of Preparation 7.
$\delta$(CDCl$_3$): 1.99 (s, 3H), 7.43-8.10 (m, 7H), 9.82 (s, 1H).

Preparation 62

6-Ethyl-3-methyl-4-naphthalen-1-yl-6H-isoxazolo[3,4-d]pyridazin-7-one

Obtained as a solid (90%) from the title compound of Preparation 61 following the procedure of Preparation 17.

δ(CDCl$_3$): 1.46 (t, 3H), 1.97 (s, 3H), 4.37 (q, 2H), 7.43-7.76 (m, 5H), 7.96-8.07 (m, 2H).

Preparation 63

5-Acetyl-4-amino-2-ethyl-6-(naphthalen-1-yl)pyridazin-3(2H)-one

Obtained as a solid (85%) from the title compound of Preparation 62 following the procedure of Preparation 23.

δ(CDCl$_3$): 1.44 (t, 3H), 1.59 (s, 3H), 4.28 (q, 2H), 7.44-8.00 (m, 7H).

Preparation 64

6-Ethyl-4-phenyl-1,6-dihydroisoxazolo[3,4-d]pyridazine-3,7-dione

To a stirred solution of PPA (354 g) in 354 mL of ethanol at 0° C., ethylhydrazine oxalate (14.58 g, 97.09 mmol) and the title compound of Preparation 37 (5.9 g, 97.09 mmol) were added portionwise. The resulting mixture was stirred at 40° C. overnight. Then it was let to cool down to room temperature and water was carefully added until a precipitate appeared. It was stirred for 1 h at 0° C. and then the final product was collected by filtration and washed with ethanol (2.04 g, 35% yield).

δ(CDCl$_3$): 1.44 (t, 3H), 4.30 (q, 2H), 7.42 (m, .3H), 7.90 (m, 2H).

Preparation 65

6-Ethyl-1-(3-fluorophenyl)-4-phenyl-1,6dihydroisoxazolo[3,4-d]pyridazine-3,7-dione A mixture of the title compound of Preparation 64 (1.03 g, 4 mmol), 3-fluorophenylboronic acid (1.12 g, 8.0 mmol), anhydrous cupric acetate (1.09 g, 6.0 mmol), triethylamine (1.11 ml, 8.0 mmol) and activated molecular sieves (2.9 g, 4 Å) in dry dichloromethane (50 ml) was stirred under air exposure at room temperature overnight. The reaction mixture was filtered through a SiO$_2$ pad and eluted with dichloromethane. The solvent was removed under reduced pressure to yield the title product (500 mg, 36% yield).

δ(CDCl$_3$): 1.45. (t, 3H), 4.32 (q, 2H), 7.12 (m, 1H), 7.42 (m, 3H), 7.52 (m, 3H), 7.85 (m, 2H).

EXAMPLES

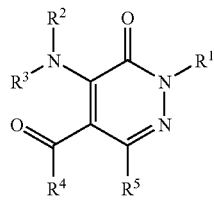

(I)

The following abreviations and their corresponding meanings have been used in the tables below:

| | |
|---|---|
| Me | Methyl |
| MeO | Methoxy |
| Et | Ethyl |
| EtO | Ethoxy |
| iPr | isopropyl |
| iPrO | isopropoxy |
| NPr | n-propyl |
| Bn | Benzyl |
| BnO | Benzyloxy |
| NBu | n-butyl |
| Pyr | Pyridyl |
| Ph | Phenyl |
| (3-Ac)Ph | 3-acetylphenyl |
| (4-Ac)Ph | 4-acetylphenyl |
| (2-Br)Ph | 2-bromophenyl |
| (3-Br)Ph | 3-bromophenyl |
| (4-Br)Ph | 4-bromophenyl |
| (2-CF$_3$)Ph | 2-trifluoromethylphenyl |
| (3-CF$_3$)Ph | 3-trifluoromethylphenyl |
| (2-CF$_3$O)Ph | 2-trifluoromethoxyphenyl |
| (4-CF$_3$O)Ph | 4-trifluoromethoxyphenyl |
| (4-CH$_3$CONH)Ph | 4-acetamidophenyl |
| (2-Cl)Ph | 2-chlorophenyl |
| (3-Cl)Ph | 3-chlorophenyl |
| (4-Cl)Ph | 4-chlorophenyl |
| (2-CN)Ph | 2-cyanophenyl |
| (3-CN)Ph | 3-cyanophenyl |
| (4-CN)Ph | 4-cyanophenyl |
| (2-CONH$_2$)Ph | 2-carbamoylphenyl |
| (3-CONH$_2$)Ph | 3-carbamoylphenyl |
| (4-CONH$_2$)Ph | 4-carbamoylphenyl |
| (2-CO$_2$H)Ph | 2-carboxyphenyl |
| (3-CO$_2$H)Ph | 3-carboxyphenyl |
| (4-CO$_2$H)Ph | 4-carboxyphenyl |
| (4-CO$_2$Me)Ph | 4-methoxycarbonylphenyl |
| (4-CO$_2$Et)Ph | 4-ethoxycarbonylphenyl |
| (3-EtO)Ph | 3-ethoxyphenyl |
| (2-F)Ph | 2-fluorophenyl |
| (3-F)Ph | 3-fluorophenyl |
| (4-F)Ph | 4-fluorophenyl |
| (4-H$_2$NCH$_2$)Ph | 4-aminomethylphenyl |
| (2-HOCH$_2$)Ph | 2-hydroxymethylphenyl |
| (3-HOCH$_2$)Ph | 3-hydroxymethylphenyl |
| (4-HOCH$_2$)Ph | 4-hydroxymethylphenyl |
| (2-Me)Ph | 2-methylphenyl |
| (3-Me)Ph | 3-methylphenyl |
| (4-Me)Ph | 4-methylphenyl |
| (4-Me$_2$N)Ph | 4-dimethylaminophenyl |
| (2-MeO)Ph | 2-methoxyphenyl |
| (3-MeO)Ph | 3-methoxyphenyl |
| (4-MeO)Ph | 4-methoxyphenyl |
| (3-MeS)Ph | 3-methylthiophenyl |
| (4-MeS)Ph | 4-methylthiophenyl |
| (4-MeSO)Ph | 4methylsulfinylphenyl |
| (2-NO$_2$)Ph | 2-nitrophenyl |
| (3-NO$_2$)Ph | 3-nitrophenyl |
| (4-NO$_2$)Ph | 4-nitrophenyl |
| (3-OH)Ph | 3-hydroxyphenyl |
| (4-Ph)Ph | 4-phenylphenyl |
| (4-Pyr)CH$_2$ | 4-pyridylmethyl |
| (2-SO$_2$NH$_2$)Ph | 2-sulfamoylphenyl |
| (4-SO$_2$NH$_2$)Ph | 4-sulfamoylphenyl |
| (4-SO$_2$NH(nBu))Ph | 4-(N-n-butyl)sulfamoylphenyl |
| (3-SH)Ph | 3-mercaptophenyl |
| (4-tBu)Ph | 4-tert-butylphenyl |

TABLE 2
| No. | R1 | R2 | R3 | R4 | R5 |
|---|---|---|---|---|---|
| 1 | Et | H | (3-F)Ph | Me | Ph |
| 2 | Et | H | 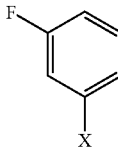 | Me | Ph |
| 3 | Et | H | 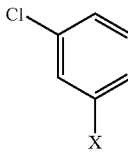 | Me | Ph |
| 4 | Et | H | (3-NO₂)Ph | Me | Ph |
| 5 | Et | H | (4-Me)Ph | Me | Ph |
| 6 | Et | H | (2-Me)Ph | Me | Ph |
| 7 | Et | H | (2-MeO)Ph | Me | Ph |
| 8 | Et | H | 1-Naphtyl | Me | Ph |
| 9 | Et | H | (4-MeS)Ph | Me | Ph |
| 10 | Et | H | (4-Ac)Ph | Me | Ph |
| 11 | Et | H | (4-Me₂N)Ph | Me | Ph |
| 12 | Et | H | 2-Naphtyl | Me | Ph |
| 13 | Et | H | (2-Cl)Ph | Me | Ph |
| 14 | Et | H | (2-CF₃O)Ph | Me | Ph |
| 15 | Et | H | (2-CF₃)Ph | Me | Ph |
| 16 | Et | H | 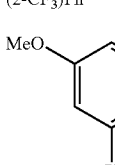 | Me | Ph |
| 17 | Et | H | 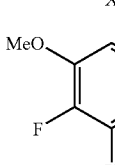 | Me | Ph |
| 18 | Et | H | 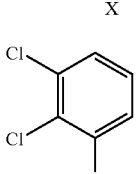 | Me | Ph |
| 19 | Et | H | 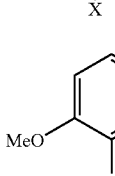 | Me | Ph |
| 20 | Et | H | 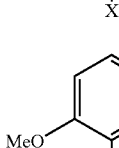 | Me | Ph |
| 21 | Et | H | (4-CO₂Me)Ph | Me | (4-MeS)Ph |
| 22 | Et | H | (3-F)Ph | Me | (4-MeS)Ph |
| 23 | Et | H | (4-CO₂H)Ph | Me | (4-MeS)Ph |
| 24 | Et | H | 1-Naphtyl | Me | (4-MeS)Ph |
| 25 | Et | H | (3-F)Ph | nPr | (4-MeS)Ph |

TABLE 2-continued

| No. | R1 | R2 | R3 | R4 | R5 |
|---|---|---|---|---|---|
| 26 | Et | H | (3-F)Ph | (CH$_3$CH$_2$)$_2$CH | (4-MeS)Ph |
| 27 | Et | H | 1-Naphtyl | (CH$_3$CH$_2$)$_2$CH | (4-MeS)Ph |
| 28 | Et | H | (4-CO$_2$Me)Ph | Me | (4-MeSO)Ph |
| 29 | Et | H | (3-F)Ph | Me | (4-MeSO)Ph |
| 30 | Et | H | (3-Cl)Ph | Me | (4-MeSO)Ph |
| 31 | Et | H | (2-Me)Ph | Me | (4-MeSO)Ph |
| 32 | Et | H | 1-Naphtyl | Me | (4-MeSO)Ph |
| 33 | Et | H | (3-NO$_2$)Ph | Me | (4-MeSO)Ph |
| 34 | Et | H | (2-MeO)Ph | Me | (4-MeSO)Ph |
| 35 | Et | H | (3-MeO)Ph | Me | (4-MeSO)Ph |
| 36 | Et | H | (3-F)Ph | Me | 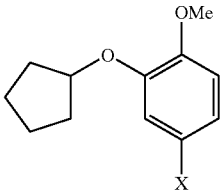 |
| 37 | Et | H | 1-Naphtyl | Me | 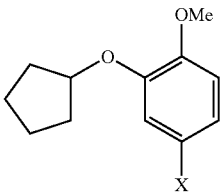 |
| 38 | Me | H | 1-Naphtyl | Me | Ph |
| 39 | Me | H | 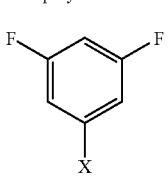 | Me | Ph |
| 40 | Me | H | (3-Cl)Ph | Me | Ph |
| 41 | Bn | H | 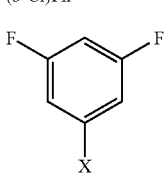 | Me | Ph |
| 42 | Bn | H | (3-F)Ph | Me | Ph |
| 43 | Bn | H | (3-Cl)Ph | Me | Ph |
| 44 | C$_3$H$_5$CH$_2$ | H | 1-Naphtyl | Me | Ph |
| 45 | C$_3$H$_5$CH$_2$ | H | (3-F)Ph | Me | Ph |
| 46 | C$_3$H$_5$CH$_2$ | H | (3-Cl)Ph | Me | Ph |
| 47 | (4-Pyr)CH$_2$ | H | 1-Naphtyl | Me | Ph |
| 48 | (4-Pyr)CH$_2$ | H | (3-F)Ph | Me | Ph |
| 49 | Et | H | (3-Me)Ph | Me | Ph |
| 50 | Et | H | (4-CO$_2$H)Ph | Me | Ph |
| 51 | Et | H | (2-CO$_2$H)Ph | Me | Ph |
| 52 | Et | H | (3-Cl)Ph | Me | Ph |
| 53 | Et | H | (3-Br)Ph | Me | Ph |
| 54 | Et | H | 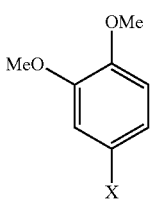 | Me | Ph |
| 55 | Et | H | (4-HOCH$_2$)Ph | Me | Ph |
| 56 | Et | H | (4-Ph)Ph | Me | Ph |

TABLE 2-continued
| No. | R1 | R2 | R3 | R4 | R5 |
|-----|----|----|----|----|----|
| 57 | Et | H | 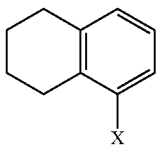 | Me | Ph |
| 58 | Et | H | 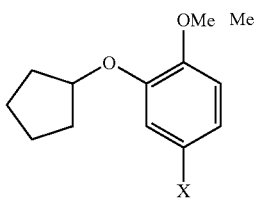 | Me | Ph |
| 59 | Et | Me | Ph | Me | Ph |
| 60 | Et | H | 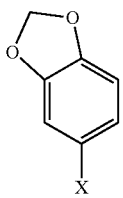 | Me | Ph |
| 61 | Et | H | (4-MeO)Ph | Me | Ph |
| 62 | Et | H | (4-Cl)Ph | Me | Ph |
| 63 | Et | H | (4-Br)Ph | Me | Ph |
| 64 | Et | H | (3-CF3)Ph | Me | Ph |
| 65 | Et | H | 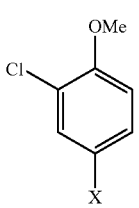 | Me | Ph |
| 66 | Et | H | (3-OH)Ph | Me | Ph |
| 67 | Et | H | (3-CO$_2$H)Ph | Me | Ph |
| 68 | Et | H | (2-F)Ph | Me | Ph |
| 69 | Et | H | (4-CO2Et)Ph | Me | Ph |
| 70 | Et | H | (4-F)Ph | Me | Ph |
| 71 | Et | H | 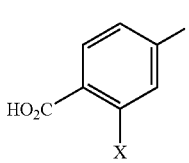 | Me | Ph |
| 72 | Et | H | (3-CN)Ph | Me | Ph |
| 73 | Et | H | 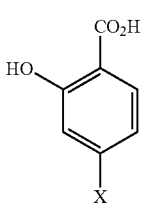 | Me | Ph |

TABLE 2-continued

| No. | R1 | R2 | R3 | R4 | R5 |
|-----|-----|-----|-----|-----|-----|
| 74 | Et | H | 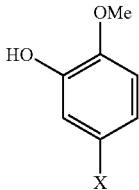 | Me | Ph |
| 75 | Et | H | (4-CONH$_2$)Ph | Me | Ph |
| 76 | Et | H | (3-MeS)Ph | Me | Ph |
| 77 | Et | H | (3-MeO)Ph | Me | Ph |
| 78 | Et | H | (3-Ac)Ph | Me | Ph |
| 79 | Et | H | 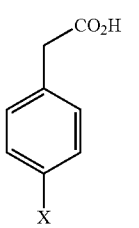 | Me | Ph |
| 80 | Et | H | (4-tBu)Ph | Me | Ph |
| 81 | Et | H | (4-SO$_2$NH$_2$)Ph | Me | Ph |
| 82 | Et | H | 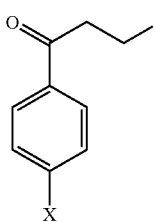 | Me | Ph |
| 83 | Et | H | [4-SO$_2$NH(nBu)]Ph | Me | Ph |
| 84 | Et | H | 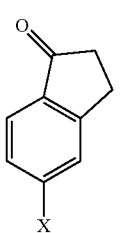 | Me | Ph |
| 85 | Et | H | (4-CH$_3$CONH)Ph | Me | Ph |
| 86 | Et | H | (4-CO$_2$H)Ph | Me | (3-Cl)Ph |
| 87 | Et | H | (3-Cl)Ph | Me | (3-Cl)Ph |
| 88 | Et | H | (3-F)Ph | Me | (3-Cl)Ph |
| 89 | Et | H | (3-Cl)Ph | Me | (4-F)Ph |
| 90 | Et | H | (3-Br)Ph | Me | (3-F)Ph |
| 91 | Et | H | (3-F)Ph | Me | (3-F)Ph |
| 92 | Et | H | (3-Cl)Ph | Me | (3-F)Ph |
| 93 | Et | H | (3-Cl)Ph | Me | (3-NO$_2$)Ph |
| 94 | Et | H | (3-F)Ph | Me | (3-NO$_2$)Ph |
| 95 | Et | H | (4-CO$_2$H)Ph | Me | (3-NO$_2$)Ph |
| 96 | Et | H | (3-Br)Ph | Me | (3-NO$_2$)Ph |
| 97 | Et | H | 1-Naphtyl | Me | (3-NO$_2$)Ph |
| 98 | Et | H | (3-Cl)Ph | nPr | Ph |
| 99 | NPr | H | (3-Cl)Ph | Me | Ph |
| 100 | NBu | H | (3-Cl)Ph | Me | Ph |
| 101 | NBu | H | (3-Br)Ph | Me | Ph |

TABLE 2-continued
| No. | R1 | R2 | R3 | R4 | R5 |
|---|---|---|---|---|---|
| 102 | Et | (3-F)Ph | 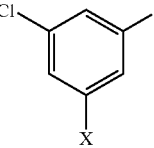 | Me | Ph |
| 103 | Et | (3-F)Ph | (3-F)Ph | Me | Ph |
| 104 | Et | (3-Cl)Ph | (3-Cl)Ph | Me | Ph |
| 105 | Et | (4-MeS)Ph | (4-MeS)Ph | Me | Ph |
| 106 | Et | (4-Ac)Ph | (4-Ac)Ph | Me | Ph |
| 107 | Et | 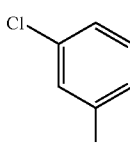 | 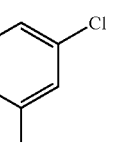 | Me | Ph |
| 108 | Et | (4-CO$_2$Me)Ph | (4-CO$_2$Me)Ph | Me | (4-MeSO)Ph |
| 109 | C$_3$H$_5$CH$_2$ | H | 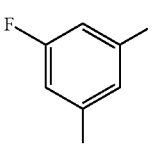 | Me | Ph |
| 110 | Me | H | (3-F)Ph | Me | Ph |
| 111 | Me | H | (4-CO$_2$H)Ph | Me | Ph |
| 112 | Ph | H | 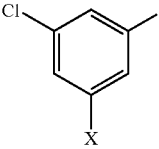 | Me | Ph |
| 113 | Ph | H | (3-F)Ph | Me | Ph |
| 114 | Ph | H | 1-Naphtyl | Me | Ph |
| 115 | Ph | H | 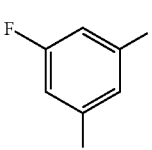 | Me | Ph |
| 116 | Ph | H | (3-Cl)Ph | Me | Ph |
| 117 | Et | H | (3-Cl)Ph | Ph | Ph |
| 118 | Et | H | (3-Cl)Ph | H | Ph |
| 119 | Et | H | (3-Cl)Ph | MeO | Ph |
| 120 | Et | H | (3-Cl)Ph | 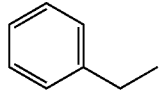 | Ph |
| 121 | Et | H | 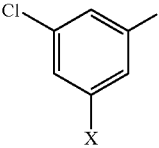 | 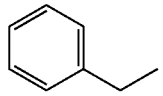 | Ph |
| 122 | Et | H | (3-CN)Ph | 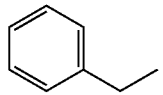 | Ph |

TABLE 2-continued

| No. | R1 | R2 | R3 | R4 | R5 |
|---|---|---|---|---|---|
| 123 | Et | H | (4-CO2H)Ph | 3-propylthiophen-4-yl | Ph |
| 124 | Et | H | (3-Cl)Ph | 3-ethylpyridin-5-yl | Ph |
| 125 | Et | H | (3-Cl)Ph | 3,5-difluorophenyl | Ph |
| 126 | Bn | H | 1-Naphthyl | Me | Ph |
| 127 | Bn | H | (4-CO2H)Ph | Me | Ph |
| 128 | (4-Pyr)CH2 | H | 3,5-difluorophenyl | Me | Ph |
| 129 | (4-Pyr)CH2 | H | (3-Cl)Ph | Me | Ph |
| 130 | Ph | H | (4-CO2H)Ph | Me | Ph |
| 131 | C3H5CH2 | H | (2-F)Ph | Me | Ph |
| 132 | C3H5CH2 | H | (2-Cl)Ph | Me | Ph |
| 133 | C3H5CH2 | H | (4-HOCH2)Ph | Me | Ph |
| 134 | C3H5CH2 | H | (3-CN)Ph | Me | Ph |
| 135 | C3H5CH2 | H | (4-CO2H)Ph | Me | Ph |
| 136 | iPr | H | 1-Naphthyl | Me | Ph |
| 137 | iPr | H | 3,5-difluorophenyl | Me | Ph |
| 138 | iPr | H | (3-F)Ph | Me | Ph |
| 139 | iPr | H | (3-Cl)Ph | Me | Ph |
| 140 | iPr | H | 3,5-dichlorophenyl | Me | Ph |
| 141 | iPr | H | (4-CO2H)Ph | Me | Ph |
| 142 | iPr | H | (2-F)Ph | Me | Ph |
| 143 | iPr | H | (2-Cl)Ph | Me | Ph |
| 144 | iPr | H | (3-CN)Ph | Me | Ph |
| 145 | iPr | H | (4-HOCH2)Ph | Me | Ph |
| 146 | HOCH2CH2 | H | (2-F)Ph | Me | Ph |
| 147 | HOCH2CH2 | H | (2-Cl)Ph | Me | Ph |
| 148 | HOCH2CH2 | H | (3-CN)Ph | Me | Ph |
| 149 | HOCH2CH2 | H | (4-HOCH2)Ph | Me | Ph |
| 150 | HOCH2CH2 | H | (3-Cl)Ph | Me | Ph |
| 151 | HOCH2CH2 | H | (2-F)Ph | Me | (3-F)Ph |
| 152 | HOCH2CH2 | H | (2-Cl)Ph | Me | (3-F)Ph |
| 153 | HOCH2CH2 | H | (3-CN)Ph | Me | (3-F)Ph |
| 154 | HOCH2CH2 | H | (4-HOCH2)Ph | Me | (3-F)Ph |
| 155 | HOCH2CH2 | H | (3-Cl)Ph | Me | (3-F)Ph |
| 156 | C3H5CH2 | H | (3-CONH2)Ph | Me | (3-Cl)Ph |
| 157 | C3H5CH2 | H | (4-HOCH2)Ph | Me | (3-Cl)Ph |
| 158 | C3H5CH2 | H | (3-CN)Ph | Me | (3-Cl)Ph |
| 159 | C3H5CH2 | H | (2-F)Ph | Me | (3-Cl)Ph |

TABLE 2-continued

| No. | R1 | R2 | R3 | R4 | R5 |
|---|---|---|---|---|---|
| 160 | C3H5CH2 | H | (3-Cl)Ph | Me | (3-Cl)Ph |
| 161 | C3H5CH2 | H | (3-CONH2)Ph | Me | (3-F)Ph |
| 162 | C3H5CH2 | H | (4-HOCH2)Ph | Me | (3-F)Ph |
| 163 | iPr | H | (3-CONH2)Ph | Me | (3-F)Ph |
| 164 | iPr | H | (4-HOCH2)Ph | Me | (3-F)Ph |
| 165 | iPr | H | (3-CN)Ph | Me | (3-F)Ph |
| 166 | iPr | H | (2-F)Ph | Me | (3-F)Ph |
| 167 | iPr | H | (3-Cl)Ph | Me | (3-F)Ph |
| 168 | iPr | H | (2-Cl)Ph | Me | (3-F)Ph |
| 169 | C3H5CH2 | H | (3-CN)Ph | Me | (4-F)Ph |
| 170 | C3H5CH2 | H | (3-CONH2)Ph | Me | (4-F)Ph |
| 171 | Et | H | (3-CONH2)Ph | Me | (3-Cl)Ph |
| 172 | Et | H | (4-HOCH2)Ph | Me | (3-Cl)Ph |
| 173 | Et | H | (3-CN)Ph | Me | (3-Cl)Ph |
| 174 | Et | H | (2-F)Ph | Me | (3-Cl)Ph |
| 175 | Et | H | (2-Cl)Ph | Me | (3-Cl)Ph |
| 176 | Et | H | (4-HOCH2)Ph | Me | (3-F)Ph |
| 177 | Et | H | (3-CONH2)Ph | Me | (3-F)Ph |
| 178 | Et | H | (3-CN)Ph | Me | (3-F)Ph |
| 179 | Et | H | (2-F)Ph | Me | (3-F)Ph |
| 180 | Et | H | (2-Cl)Ph | Me | (3-F)Ph |
| 181 | Et | H | (4-HOCH2)Ph | Me | (4-F)Ph |
| 182 | Et | H | (4-CN)Ph | Me | (4-F)Ph |
| 183 | Et | H | (3-CONH2)Ph | Me | (4-F)Ph |
| 184 | Et | H | (3-CN)Ph | Me | (4-F)Ph |
| 185 | Et | H | (2-F)Ph | Me | (4-F)Ph |
| 186 | Et | H | (2-Cl)Ph | Me | (4-F)Ph |
| 187 | Et | H | (3-Cl)Ph | Me | 1-Naphthyl |
| 188 | Et | H | 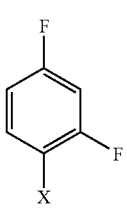 | Me | Ph |
| 189 | Et | H | 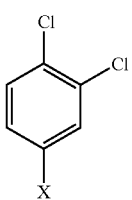 | Me | Ph |
| 190 | Et | H | 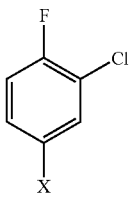 | Me | Ph |
| 191 | Et | H | 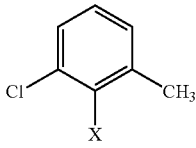 | Me | Ph |
| 192 | Et | H | 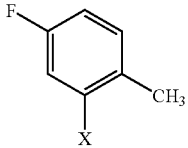 | Me | Ph |

TABLE 2-continued
| No. | R1 | R2 | R3 | R4 | R5 |
|-----|----|----|----|----|----|
| 193 | Et | H | 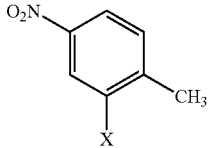 | Me | Ph |
| 194 | Et | H | 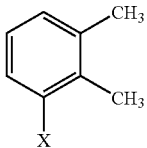 | Me | Ph |
| 195 | Et | H | 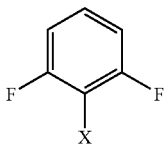 | Me | Ph |
| 196 | Et | H | 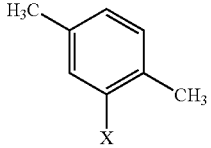 | Me | Ph |
| 197 | Et | H | 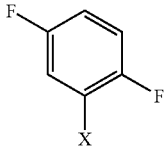 | Me | Ph |
| 198 | Et | H | 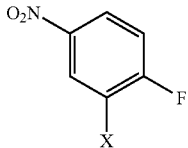 | Me | Ph |
| 199 | Et | H | 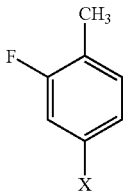 | Me | Ph |
| 200 | Et | H | 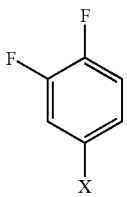 | Me | Ph |
| 201 | Et | H | (2-Br)Ph | Me | Ph |
| 202 | Et | H |  | Me | Ph |

TABLE 2-continued
| No. | R1 | R2 | R3 | R4 | R5 |
|-----|----|----|----|----|----|
| 203 | Et | H | 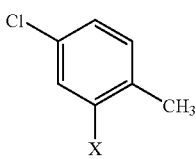 | Me | Ph |
| 204 | Et | H | 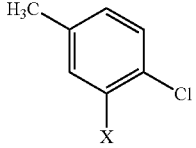 | Me | Ph |
| 205 | Et | H | 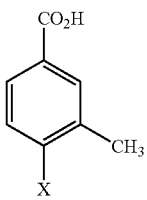 | Me | Ph |
| 206 | Et | H | 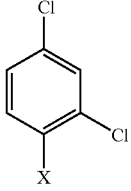 | Me | Ph |
| 207 | Et | H | 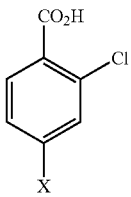 | Me | Ph |
| 208 | Et | H | 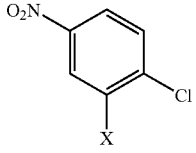 | Me | Ph |
| 209 | Et | H | 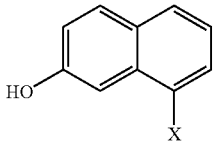 | Me | Ph |
| 210 | Et | H | 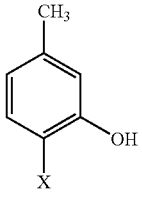 | Me | Ph |

TABLE 2-continued
| No. | R1 | R2 | R3 | R4 | R5 |
|-----|----|----|----|----|----|
| 211 | Et | H | 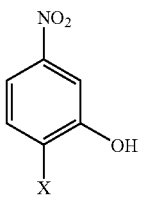 | Me | Ph |
| 212 | Et | H | 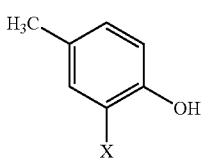 | Me | Ph |
| 213 | Et | H | 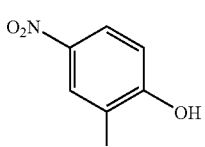 | Me | Ph |
| 214 | Et | H | 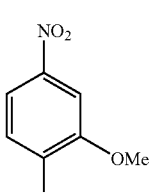 | Me | Ph |
| 215 | Et | H | (4-CF3O)Ph | Me | Ph |
| 216 | Et | H | (3-EtO)Ph | Me | Ph |
| 217 | Et | H | 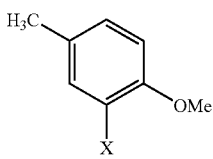 | Me | Ph |
| 218 | Et | H | 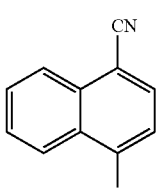 | Me | Ph |
| 219 | Et | H | 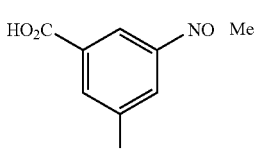 | Me | Ph |
| 220 | Et | H | (3-SH)Ph | Me | Ph |
| 221 | Et | H | 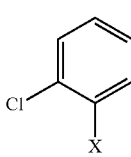 | Me | Ph |

TABLE 2-continued
| No. | R1 | R2 | R3 | R4 | R5 |
|---|---|---|---|---|---|
| 222 | Et | H | 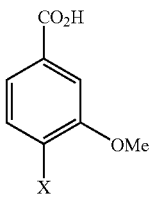 | Me | Ph |
| 223 | Et | H | 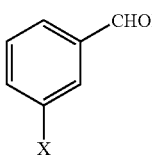 | Me | Ph |
| 224 | Et | H | (3-HOCH2)Ph | Me | Ph |
| 225 | Et | H | 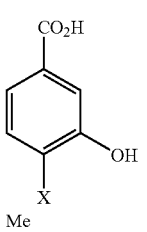 | Ph | |
| 226 | Et | H | 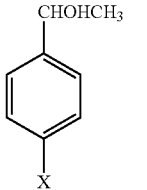 | Me | Ph |
| 227 | Et | H | 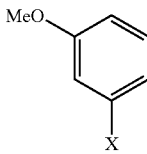 | Me | Ph |
| 228 | Et | H | 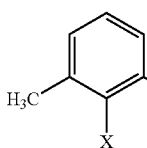 | | |
| 229 | Et | H | 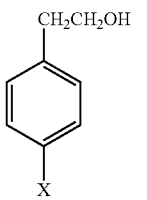 | Me | Ph |
| 230 | Et | H | (4-NO2)Ph | Me | Ph |
| 231 | Et | H | (4-CN)Ph | Me | Ph |
| 232 | Et | H | (3-CONH2)Ph | Me | Ph |
| 233 | Et | H | (2-HOCH2)Ph | Me | Ph |
| 234 | Et | H | (2-CONH2)Ph | Me | Ph |
| 235 | Et | H | (2-SO2NH2)Ph | Me | Ph |
| 236 | Et | H | (2-CN)Ph | Me | Ph |

TABLE 2-continued
| No. | R1 | R2 | R3 | R4 | R5 |
|---|---|---|---|---|---|
| 237 | Et | H | 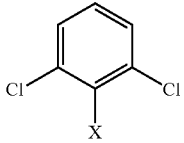 | Me | Ph |
| 238 | Et | H | (2-NO2)Ph | Me | Ph |
| 239 | Et | H | 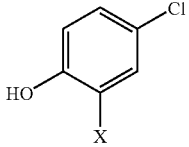 | Me | Ph |
| 240 | Et | H | 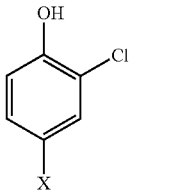 | Me | Ph |
| 241 | Et | H | (4-SO2NH2)Ph | Me | Ph |
| 242 | Et | H | 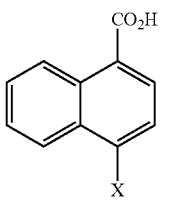 | Me | Ph |
| 243 | Et | H | 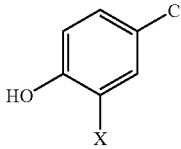 | Me | Ph |
| 244 | Et | H | 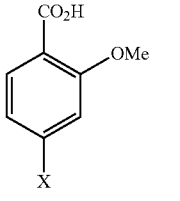 | Me | Ph |
| 245 | Et | H | 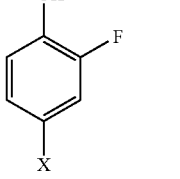 | Me | Ph |
| 246 | Et | H | 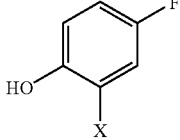 | Me | Ph |

TABLE 2-continued

| No. | R1 | R2 | R3 | R4 | R5 |
|-----|----|----|----|----|----|
| 247 | Et | H | 6-hydroxy-naphthalen-1-yl (HO at 6, X at 5) | Me | Ph |
| 248 | Et | H | 2-fluoro-6-X-3-methylphenyl (F, CH₃, X) | Me | Ph |
| 249 | Et | H | 2-hydroxy-1-X-naphthalen-1-yl (OH, X) | Me | Ph |
| 250 | Et | H | 5-hydroxy-naphthalen-1-yl (OH, X) | Me | Ph |
| 251 | Et | H | 2-fluoro-4-X-benzoic acid (CO₂H, F, X) | Me | Ph |
| 252 | Et | H | 3-X-N-methylbenzamide (CON(CH₃), X) | Me | Ph |
| 253 | Et | H | 3-X-N-methylbenzamide (CONHCH, X) | Me | Ph |
| 254 | Et | H | 1-nitro-4-X-naphthalen-4-yl (NO₂, X) | Me | Ph |

TABLE 2-continued
| No. | R1 | R2 | R3 | R4 | R5 |
|---|---|---|---|---|---|
| 255 | Et | H | 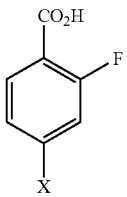 2-F, 4-X benzoic acid | Me | Ph |
| 256 | Et | H | 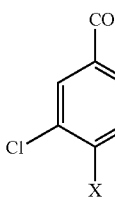 3-Cl, 4-X benzoic acid | Me | Ph |
| 257 | Et | H | 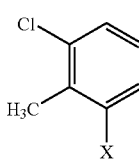 3-Cl, 2-CH₃, 1-X phenyl | Me | Ph |
| 258 | Et | H | (4-CO2Me)Ph | Me | Ph |
| 259 | Et | H | 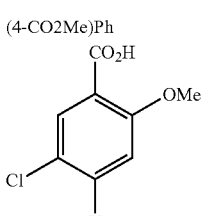 2-OMe, 5-Cl, 4-X benzoic acid | Me | Ph |
| 260 | Et | H | 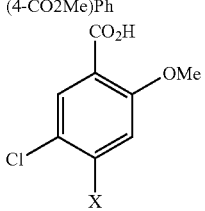 4-CH₃, 3-X, CONHMe phenyl | Me | Ph |
| 261 | Et | H | 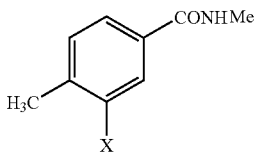 4-Cl, 3-X, CONHMe phenyl | Me | Ph |
| 262 | Et | H | 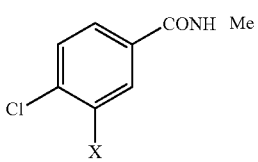 1-Cl, 4-X naphthyl | Me | Ph |
| 263 | Et | H | 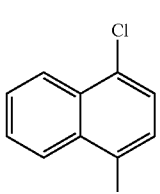 3,5-diF, 4-X phenyl | Me | Ph |

TABLE 2-continued

| No. | R1 | R2 | R3 | R4 | R5 |
|---|---|---|---|---|---|
| 264 | Et | H | 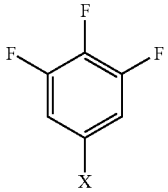 | Me | Ph |
| 265 | Et | H | 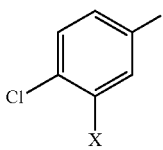 | Me | Ph |
| 266 | Et | H | (4-H2NCH2)Ph | Me | Ph |
| 267 | Et | H | 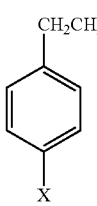 | Me | Ph |
| 268 | Et | H | (3-F)Ph | Me | (4-MeS)Ph |
| 269 | Et | H | (3-F)Ph | OH | Ph |
| 270 | Et | H | (3-Cl)Ph | OH | Ph |
| 271 | Et | H | (3-F)Ph | MeO | Ph |
| 272 | Et | H | (3-Cl)Ph | PrO | Ph |
| 273 | Et | H | (3-Cl)Ph | EtO | Ph |
| 274 | Et | H | (3-Cl)Ph | BnO | Ph |

The symbol X in the structures shows only the binding point. It does not represent any atom.

Example 1

5-Acetyl-2-ethyl-4-[(3-fluorophenyl)amino]-6-phenylpyridazin-3(2H)-one

A mixture of the title compound of Preparation 22 (250 mg, 0.97 mmol), 3-fluorophenylboronic acid (272 mg, 1.94 mmol), anhydrous cupric acetate (265 mg, 1.46 mmol), triethylamine (0.27 ml, 1.94 mmol) and activated molecular sieves (720 mg, 4 Å) in dry dichloromethane (12 ml) was stirred under air exposure at room temperature for 24 h. The reaction was filtered and the solvent removed under reduced pressure. The resulting residue was purified by flash column chromatography ($SiO_2$, dichloromethane-ethyl acetate) to yield the title product (216 mg, 63% yield).

m.p. 176.5-178.2° C. δ($CDCl_3$): 1.45 (t, 3H), 1.74 (s, 3H), 4.30 (q, 2H), 6.76 (m, 1H), 6.85 (m, 2H), 7.25 (m,1H), 7.40 (m, 5H), 8.24 (s, 1H).

Example 2

5-Acetyl-4-[(3,5difluorophenyl)amino]-2-ethyl-6-phenylpyridazin-3(2H)-one

Obtained as a solid (54%) from the title compound of Preparation 22 and 3,5-difluorophenylboronic acid following the procedure of Example 1.

m.p. 243.4-244.6° C. δ($CDCl_3$): 1.44 (t, 3H), 1.80 (s, 3H), 4.31 (q, 2H), 6.59 (m, 3H), 7.40 (m, 5H), 8.26 (s,1H).

Example 3

5-Acetyl-4-[(3,5-dichlorophenyl)amino]-2-ethyl-6-phenylpyridazin-3(2H)-one

Obtained as a solid (55%) from the title compound of Preparation 22 and 3,5-dichlorophenylboronic acid following the procedure of Example 1.

m.p. 254.4-254.6° C. δ(DMSO-d6): 1.33 (t, 3H), 1.84 (s, 3H), 4.17 (q, 2H), 7.1 (s, 1H), 7.19 (m, 2H), 7.38 (m, 5H), 9.14 (s, 1H).

Example 4

5-Acetyl-2-ethyl-4-[(3-nitrophenyl)amino]-6-phenylpyridazin-3(2H)-one

Obtained as a solid (40%) from the title compound of Preparation 22 and 3-nitrophenylboronic acid following the procedure of Example 1.

m.p. 241.8-243.7° C. δ($CDCl_3$): 1.45 (t, 3H), 1.78 (s, 3H), 4.31 (q, 2H), 7.45 (m, 7H), 7.84 (s,1H), 8.02 (d, 1H), 8.73 (s, 1H).

Example 5

5-Acetyl-2-ethyl-4-[(4-methylphenyl)amino]-6-phenylpyridazin-3(2H)-one

Obtained as a solid (50%) from the title compound of Preparation 22 and 4-methylphenylboronic acid following the procedure of Example 1.

LRMS: m/Z 347 (M+1)$^+$. δ(CDCl$_3$): 1.46 (t, 3H), 1.58 (s, 3H), 2.34 (s, 3H), 4.31 (q, 2H), 6.95 (d, 2H), 7.13 (d, 2H), 7.34 (m, 5H), 8.03 (s, 1H).

Example 6

5-Acetyl-2-ethyl-4-[(2-methylphenyl)amino]-6-phenylpyridazin-3(2H)-one

Obtained as a solid (54%) from the title compound of Preparation 22 and 2-methylphenylboronic acid following the procedure of Example 1.

m.p. 189.8-190.7° C. δ(CDCl$_3$): 1.46 (t, 3H), 1.51 (s, 3H), 2.33 (s, 3H), 4.31 (q, 2H), 6.97 (d, 1H), 7.11 (m, 2H), 7.23 (m, 1H), 7.34 (m, 5H), 7.81 (s, 1H).

Example 7

5-Acetyl-2-ethyl-4-[(2-methoxyphenyl)amino]-6-phenylpyridazin-3(2H)-one

Obtained as a solid (30%) from the title compound of Preparation 22 and 2-methoxyphenylboronic acid following the procedure of Example 1.

m.p. 205.4-206.8° C. δ(DMSO-d6): 1.33 (t, 3H), 1.52 (s, 3H), 3.73 (s, 3H), 4.16 (q, 2H), 6.85 (t, 1H), 6.97 (d, 1H), 7.02 (d, 1H), 7.14 (t, 1H), 7.26 (m, 2H), 7.36 (m, 3H), 8.47 (s, 1H).

Example 8

5-Acetyl-2-ethyl-4-(1-naphthylamino)-6-phenylpyridazin-3(2H)-one

Obtained as a solid (51%) from the title compound of Preparation 22 and 1-naphthylboronic acid following the procedure of Example 1.

m.p. 196.8-197.7° C. δ(CDCl$_3$): 1.23 (s, 3H), 1.52 (t, 3H), 4.36 (q, 2H), 6.85 (t, 1H), 7.34 (m, 6H), 7.58 (m, 2H), 7.75 (d, 1H), 7.86 (d, 1H), 8.12 (d, 1H), 8.27 (s, 1H).

Examples 9-20

5-Acetyl-2-ethyl-4-{[(4-methylthio)phenyl]amino}-6-phenylpyridazin-3(2H)-one

5-Acetyl-4-{(4-acetylphenyl)amino}-2-ethyl-6-phenylpyridazin-3(2H)-one

5-Acetyl-4-{[4-dimethylamino)phenyl]amino}-2-ethyl-6-phenylpyridazin-3(2H)-one

5-Acetyl-2-ethyl-4-(2-naphthylamino)-6-phenylpyridazin-3(2H)-one

5-Acetyl-4-[(2-chlorophenyl)amino]-2-ethyl-6-phenylpyridazin-3(2H)-one

5-Acetyl-2-ethyl-6-phenyl-4-([3-(trifluoromethoxy)phenyl]amino)pyridazin-3(2H)-one 5-Acetyl-2-ethyl-6-phenyl-4-([2-(trifluoromethyl)phenyl]amino)pyridazin-3(2H)-one 5-Acetyl-2-ethyl-4-[(2,5-dimethoxyphenyl)amino]-6-phenylpyridazin-3(2H)-one 5-Acetyl-2-ethyl-4-[(2-fluoro-3-methoxyphenyl)amino]-6-phenylpyridazin-3(2H)-one 5-Acetyl-4-[(2,3-dichlorophenyl)amino]-2-ethyl-6-phenylpyridazin-3(2H)-one 5-Acetyl-4-[(5-chloro-2-methoxyphenyl)amino]-2-ethyl-6-phenylpyridazin-3(2H)-one 5-Acetyl-2-ethyl-4-[(5-fluoro-2-methoxyphenyl)amino]-2-ethyl-6-phenylpyridazin-3(2H)-one The title compounds were synthesized from the tile compound of Preparation 22 and the corresponding boronic acid following the procedure of Example 1. The ESI/MS data and HPLC retention times are summarized in Table 3.

TABLE 3

| EXAMPLE | ESI/MS m/e (M + H)$^+$ | Retention Time (min) |
|---|---|---|
| 9 | 380 | 9.3 |
| 10 | 376 | 8.4 |
| 11 | 377 | 8.7 |
| 12 | 384 | 9.6 |
| 13 | 368 | 9.3 |
| 14 | 418 | 9.8 |
| 15 | 402 | 9.7 |
| 16 | 394 | 8.9 |
| 17 | 382 | 8.8 |
| 18 | 403 | 9.8 |
| 19 | 398 | 9.5 |
| 20 | 382 | 9.0 |

Example 21

Methyl 4-({5-acetyl-2-ethyl-6-[4-methylthio)phenyl]-3-oxo-2,3-dihydropyridazin-4-yl}amino)benzoate Obtained as a solid (20%) from the title compound of preparation 23 and 4-(methoxycarbonyl)phenylboronic acid following the procedure of Example 1.

LRMS: m/Z 438 (M+1)$^+$. Retention Time: 9.4 min. δ(CDCl$_3$): 1.42 (t, 3H), 1.81 (s, 3H), 2.46 (s, 3H), 3.92 (s, 3H), 4.32 (q, 2H), 7.05 (d, 2H), 7.23 (m, 4H), 7.99 (d, 2H), 8.38 (s, 1H).

Examples 22-24

5-Acetyl-2-ethyl-4-[(3-fluorophenyl)amino]-6-[4-(methylthio)phenyl]pyridazin-3(2H)-one 4-({5-Acetyl-2-ethyl-6-[4-(methylthio)phenyl]-3-oxo-2,3-dihydropyridazin-4-yl}amino)benzoic acid 5-Acetyl-2-ethyl-6-[4-(methylthio)phenyl]-4-(1-naphthylamino)pyridazin-3(2H)-one The title compounds were synthesized from the title compound of Preparation 23 and the corresponding boronic acid following the procedure of Example 1. The ESI/MS data and HPLC retention times are summarized in Table 4.

TABLE 4

| EXAMPLE | ESI/MS m/e (M + H)+ | Retention Time (min) |
|---|---|---|
| 22 | 398 | 9.5 |
| 23 | 424 | 8.7 |
| 24 | 430 | 10.0 |

Example 25

5-Butyryl-2-ethyl-4-[(3-fluorophenyl)amino]-6-[4-(methylthio)phenyl]pyridazin-3(2H)-one Obtained from the title compound of Preparation 24 and 3-fluorophenylboronic acid following the procedure of Example 1.
LRMS: m/Z 426 (M+1)+ Retention Time: 10.2 min Example 26

2-Ethyl-5-(2-ethylbutanoyl)-4-[(3-fluorophenyl)amino]-6-[4-(methylthio)phenyl]pyridazin-3(2H)-one Obtained from the title compound of Preparation 25 and 3-fluorophenylboronic acid following the procedure of Example 1.
LRMS: m/Z 454 (M+1)+ Retention Time: 11.1 min Example 27

2-Ethyl-5-(2-ethylbutanoyl)-6-[4-(methylthio)phenyl]-4-(naphth-1-ylamino)pyridazin-3(2H)-one Obtained from the title compound of Preparation 25 and 1-naphtylboronic acid following the procedure of Example 1.
LRMS: m/Z 486 (M+1)+ Retention Time: 10.8 min Example 28

Methyl 4-({5-acetyl-2-ethyl-6-[4-(methylsulphinyl)phenyl]-3-oxo-2,3-dihydropyridazin-4-yl}amino)benzoate Obtained as a solid (20%) from the title compound of Preparation 26 and 4-(methoxycarbonyl)phenylboronic acid following the procedure of Example 1.
LRMS: m/Z 454 (M+1)+. Retention Time: 7.2 min.
δ(CDCl$_3$): 1.42 (t, 3H), 1.81 (s, 3H), 2.78 (s, 3H), 3.93 (s, 3H), 4.32 (q, 2H), 7.10 (d, 2H), 7.58 (d, 2H), 7.75 (d, 2H), 8.01 (d, 2H), 8.35 (s, 1H).

Examples 29-35

5-Acetyl-2-ethyl-4[(3-fluorophenyl)amino]-6-[4-(methylsulphinyl)phenyl]pyridazin-3(2H)-one 5-Acetyl-4-[(3-chlorophenyl)amino]-2-ethyl-6-[4-(methylsulphinyl)phenyl]pyridazin-3(2H)-one 5-Acetyl-2-ethyl-4-[(2-methylphenyl)amino]-6-[4-(methylsulphinyl)phenyl]pyridazin-3(2H)-one 5-Acetyl-2-ethyl-6-[4-(methylsulphinyl)phenyl]-4-(1-naphthylamino)pyridazin-3(2H)-one 5-Acetyl-2-ethyl-6-[4-(methylsulphinyl)phenyl]-4-[(3-nitrophenyl)amino]pyridazin-3(2H)-one 5-Acetyl-2-ethyl-6-[4-(methylsulphinyl)phenyl]-4-[(2-methoxyphenyl)amino]pyridazin-3(2H)-one 5-Acetyl-2-ethyl-6-[4-(methylsulphinyl)phenyl]-4-[(3-methoxyphenyl)amino]pyridazin-3(2H)-one The title compounds were synthesized from the title compound of Preparation 26 and the corresponding boronic acid following the procedure of Example 1. The ESI/MS data and HPLC retention times are summarized in Table 5.

TABLE 5

| EXAMPLE | ESI/MS m/e (M + H)+ | Retention Time (min) |
|---|---|---|
| 29 | 414 | 7.2 |
| 30 | 430 | 7.8 |
| 31 | 410 | 7.5 |
| 32 | 446 | 8.1 |
| 33 | 441 | 7.2 |
| 34 | 426 | 7.2 |
| 35 | 426 | 7.3 |

Example 36

5-Acetyl-6-[3-(cyclopentyloxy)methoxyphenyl]-2-ethyl-4-[(3-fluorophenyl)amino]pyridazin-3(2H)-one Obtained from the title compound of Preparation 27 and 3-fluorophenylboronic acid following the procedure of Example 1.
LRMS: m/Z 466 (M+1)+ Retention Time: 10.3 min Example 37

5-Acetyl-6-[3-cyclopentyloxy)-4-methoxyphenyl]-2-ethyl-4-(1-naphthylamino)pyridazin-3(2H)-one Obtained from the title compound of Preparation 27 and 1-naphtylboronic acid following the procedure of Example 1.
LRMS: m/Z 498 (M+1)+ Retention Time: 10.8 min Examples 38-40

5-Acetyl-2-methyl-4-(1-naphthylamino)-6-phenylpyridazin-3(2H)-one

5-Acetyl-4-[(3,5-difluorophenyl)amino]-2-methyl-6-phenylpyridazin-3(2H)-one

5-Acetyl-4-[(3-chlorophenyl)amino]-2-methyl-6-phenylpyridazin-3(2H)-one

The title compounds were synthesized from 5-acetyl-4-amino-2-methyl-6-phenylpyridazin-3(2H)-one (Dal Piaz, V., Ciciani, G, Giovannoni, M. P., *Heterocycles*, 1991, 32, 1173-9) and the corresponding boronic acid following the procedure of Example 1. The ESI/MS data and HPLC retention times are summarized in Table 6.

TABLE 6

| EXAMPLE | ESI/MS m/e (M + H)+ | Retention Time (min) |
|---|---|---|
| 38 | 370 | 9.1 |
| 39 | 356 | 8.8 |
| 40 | 354 | 9.0 |

Examples 41-43

5-Acetyl-2-benzyl-4-[(3,5-difluorophenyl)amino]-6-phenylpyridazin-3(2H)-one

5-Acetyl-2-benzyl-4-[(3-fluorophenyl)amino]-6-phenylpyridazin-3(2H)-one

5-Acetyl-2-benzyl-4-[(3-chlorophenyl)amino]-6-phenylpyridazin-3(2H)-one

The title compounds were synthesized from the title compound of Preparation 28 and the corresponding boronic acid following the procedure of Example 1. The ESI/MS data and HPLC retention times are summarized in Table 7.

TABLE 7

| EXAMPLE | ESI/MS m/e (M + H)+ | Retention Time (min) |
|---|---|---|
| 41 | 432 | 10.0 |
| 42 | 414 | 9.8 |
| 43 | 429 | 10.2 |

Examples 44-46

5-Acetyl-2-(cyclopropylmethyl)-4-(1-naphthylamino)-6-phenylpyridazin-3(2H)-one

5-Acetyl-2-(cyclopropylmethyl)-4-[(3-fluorophenyl)amino]-6-phenylpyridazin-3(2H)-one 5-Acetyl-4-[(3-chlorophenyl)amino]-2-(cyclopropylmethyl)-6-phenylpyridazin-3(2H)-one The title compounds were synthesized from the title compound of Preparation 29 and the corresponding boronic acid following the procedure of Example 1. The ESI/MS data and HPLC retention times are summarized in Table 8.

TABLE 8

| EXAMPLE | ESI/MS m/e (M + H)+ | Retention Time (min) |
|---|---|---|
| 44 | 410 | 10.1 |
| 45 | 378 | 9.5 |
| 46 | 394 | 9.9 |

Example 47

5-Acetyl-4-(1-naphthylamino)-6-phenyl-2-pyridin4-ylmethylpyridazin-3(2H)-one

Obtained from the title compound of Preparation 30 and 1-naphtylboronic acid following the procedure of Example 1.
LRMS: m/Z 447 (M+1)+ Retention Time: 8.6 min Example 48

5-Acetyl-4-[(3-fluorophenyl)amino]-phenyl-2-pyridin-4-ylmethylpyridazin-3(2H)-one Obtained from the title compound of Preparation 30 and 3-fluorophenylboronic acid following the procedure of Example 1.
LRMS: m/Z 415 (M+1)+ Retention Time: 7.8 min Example 49

5-Acetyl-2-ethyl-4-[(3-methylphenyl)amino]-6-phenylpyridazin-3(2H)-one

To a stirred solution of 57 mg (0.20 mmol) of 5-acetyl-2-ethyl-4-nitro-6-phenylpyridazin-3(2H)-one (Dal Piaz, V et al, *J. Med. Chem.* 1997, 40, 1417) (57 mg, 0.20 mmol) in ethanol (2 ml), m-toluidine (64 mg, 0.60 mmol) was added portionwise. The resulting mixture was stirred at room temperature for 30 min and the final product was collected by filtration and washed with ethanol and diethylether to yield the title compound (24 mg, 35% yield).
LRMS: m/Z 348 (M+1)+. Retention Time: 9.9 min.
δ(CDCl$_3$): 1.42 (t, 3H), 1.57 (s, 3H), 2.50 (s, 3H), 4.30 (q, 2H), 6.87 (m, 2H), 7.03 (d, 1H), 7.17 (d,1H), 7.48 (m, 5H), 8.03 (s, 1H).

Example 50

4-[(5-Acetyl-2-ethyl-3-oxo-6-phenyl-2,3-dihydropyridazin-4-yl)amino]benzoic acid Obtained as a solid from 5-acetyl-2-ethyl-4-nitro-6-phenylpyridazin-3(2H)-one (Dal Piaz, V et al, *J. Med. Chem.* 1997, 40, 1417) and 4-aminobenzoic acid following the procedure of Example 49. The product was recrystallized from ethanol/dichloromethane (76% yield).
m.p. 273.0-273.4° C. δ(DMSO-d6): 1.32 (t, 3H), 1.83 (s, 3H), 4.17 (q, 2H), 7.04 (d, 2H), 7.31 (m, 2H), 7.40 (m, 3H), 7.76 (d, 2H), 9.20 (s, 1H), 12.72 (bs, 1H).

Example 51

2-[(5-Acetyl-2-ethyl-3-oxo-6-phenyl-2,3-dihydropyridazin-4-yl)amino]benzoic acid Obtained (25%) from 5-acetyl-2-ethyl-4-nitro-6-phenylpyridazin-3(2H)-one (Dal Piaz, V et al., *J. Med. Chem:* 1997, 40, 1417) and 2-aminobenzoic acid following the procedure of Example 49.
LRMS: m/Z 348 (M+1)+. δ(CDCl3): 1.42 (t, 3H), 1.83 (s, 3H), 4.18 (q, 2H), 6.82 (d, 1H), 7.07 (t, 1H), 7.42 (m, 6H), 8.02 (d, 1H), 10.02 (s, 1H), 12.72 (bs, 1H).

Example 52

5-Acetyl-4-[(3-chlorophenyl)amino]-2-ethyl-6-phenylpyridazin-3(2H)-one

Obtained (64%) from 5-acetyl-2-ethyl-4-nitro-6-phenylpyridazin-3(2H)-one (Dal Piaz, V et al, *J. Med. Chem.* 1997, 40, 1417) and 3-chloroaniline following the procedure of Example 49.

m.p. 189.0-190.6° C. δ(DMSO-d6): 1.34 (t, 3H), 1.75 (s, 3H), 4.18 (q, 2H), 7.02 (m,1H),7.17 (m, 2H), 7.30 (m, 3H), 7.40 (m, 3H), 9.05 (s, 1H).

Example 53

5-Acetyl-4-[(3-bromophenyl)amino]-2-ethyl-6-phenylpyridazin-3(2H)-one

Obtained (65%) from 5-acetyl-2-ethyl-4-nitro6-phenylpyridazin-3(2H)-one (Dal Piaz, V et al, *J. Med. Chem.* 1997, 40, 1417) and 3-bromoaniline following the procedure of Example 49.

m.p. 191.3-192.1° C. δ(DMSO-d6): 1.33 (t, 3H), 1.75 (s, 3H), 4.17 (q, 2H), 7.03 (m, 1H), 7.22 (m, 3H), 7.30 (m, 2H), 7.42 (m, 3H), 9.06 (s, 1H).

Example 54

5-Acetyl-4-[(3,4-dimethoxyphenyl)amino]-2-ethyl-6-phenylpyridazin-3(2H)-one

Obtained (76%) from 5-acetyl-2-ethyl-4-nitro-6-phenylpyridazin-3(2H)-one (Dal Piaz, V et al, *J. Med. Chem.* 1997, 40, 1417) and 3,4-dimethoxyaniline following the procedure of Example 49.

LRMS: m/Z 388 (M+1)$^+$ δ(CDCl$_3$): 1.42 (t, 3H), 1.65 (s, 3H), 3.78 (m, 6H), 4.25 (q, 2H), 6.62 (m, 2H), 6.78 (m, 1H), 7.38 (m, 5H), 7.98 (s, 1H).

Example 55

5-Acetyl-2-ethyl-4-[4-(hydroxymethyl)phenyl]amino)-6-phenylpyridazin-3(2H)-one Obtained (20%) from 5-acetyl-2-ethyl-4-nitro-6-phenylpyridazin-3(2H)-one (Dal Piaz, V et al, *J. Med. Chem.* 1997, 40, 1417) and (4-aminophenyl)methanol following the procedure of Example 49.

LRMS: m/Z 388 (M+1)$^+$ δ(CDCl$_3$): 1.62 (t, 3H), 1.84 (s, 3H), 2.10 (bs, 1H), 4.25 (q, 2H), 4.63 (s, 2H), 7.05 (d, 2H), 7.38 (m, 7H), 8.22 (s, 1H).

Example 56

5-Acetyl-4-(1,1'-biphenyl-4-ylamino)-2-ethyl-6-phenylpyridazin-3(2H)-one

Obtained (22%) from 5-acetyl-2-ethyl-4-nitro-6-phenylpyridazin-3(2H)-one (Dal Piaz, V et al, *J. Med. Chem.* 1997, 40, 1417) and 1,1'-biphenyl-4-amine following the procedure of Example 49.

LRMS: m/Z 410 (M+1)$^+$ δ(CDCl3):.1.42 (t, 3H), 1.77 (s, 3H), 4.28 (q, 2H), 7.15 (d, 2H), 7.38 (m, 9H), 7.56 (m, 3H), 8.22 (s, 1H).

Example 57

5-Acetyl-2-ethyl-6-phenyl-4-(5,6,7,8-tetrahydronaphthalen-1-ylamino)pyridazin-3(2H)-one Obtained (23%) from 5-acetyl-2-ethyl-4-nitro-6-phenylpyridazin-3(2H)-one (Dal Piaz, V et al, *J. Med. Chem.* 1997, 40, 1417) and 5,6,7,8-tetrahydronaphthalen-1-amine following the procedure of Example 49.

LRMS: m/Z 388 (M+1)$^+$ δ(CDCl$_3$): 1.42 (t, 3H), 1.44 (s, 3H), 1.78 (m, 4H), 2.67 (m, 4H), 4.28 (q, 2H), 6.75 (m, 1H), 6.98 (m, 2H), 7.36 (m, 5H), 7.78. (s, 1H).

Example 58

5-acetyl-4-{[3-(cyclopentyloxy)-4-methoxyphenyl]amino}-2-ethyl-6-phenylpyridazin-3(2H)-one Obtained (23%) from 5-acetyl-2-ethyl-4-nitro-6-phenylpyridazin-3(2H)-one (Dal Piaz, V et al, *J. Med. Chem.* 1997, 40, 1417) and 3-(cyclopentyloxy)-4-methoxyaniline (World Patent Application WO9325517) following the procedure of Example 49.

LRMS: m/Z 448 (M+1)$^+$ δ(CDCl$_3$): 1.45 (m, 10H), 1.90 (m,4H), 3.82 (s, 3H), 4.32 (q, 2H), 4.70 (m, 1H), 6.66 (m, 3H), 7.38 (m, 5H), 7.82 (s, 1H).

Example 59

5-Acetyl-2-ethyl-4-[N-methyl-N-phenylamino]-6-phenylpyridazin-3(2H)-one

Obtained (28%) from 5-acetyl-2-ethyl-4-nitro-6-phenylpyridazin-3(2H)-one (Dal Piaz, V et al, *J. Med. Chem.* 1997, 40, 1417) and N-methylaniline following the procedure of Example 49.

LRMS: m/Z 348 (M+1)$^+$ δ(CDCl3): 1.42 (t, 3H), 1.83 (s, 3H), 3.28 (s, 3H), 4.32 (q, 2H), 6.78 (m, 2H), 6.90 (m, 1H), 7.25 (m, 1H), 7.42 (m, 6H).

Examples 60-85

5-Acetyl-4-(1,3-benzodioxol-5-ylamino)-2-ethyl-6-phenylpyridazin-3(2H)-one

5-Acetyl-2-ethyl-4-[(4-methoxyphenyl)amino]-6-phenylpyridazin-3(2H)-one

5-Acetyl-4-[(4-chlorophenyl)amino]-2-ethyl-6-phenylpyridazin-3(2H)-one

5-Acetyl-4-[(4-bromophenyl)amino]-2-ethyl-6-phenylpyridazin-3(2H)-one

5-Acetyl-2-ethyl-6-phenyl-4-{[3-(trifluoromethyl)phenyl]amino}pyridazin-3(2H)-one 5-Acetyl-4-[(3-chloro-4-methoxyphenyl)amino]-2-ethyl-6-phenylpyridazin-3(2H)-one 5-Acetyl-2-ethyl-4-[(3-hydroxyphenyl)amino]-6-phenylpyridazin-3(2H)-one 3-[(5-Acetyl-2-ethyl-3-oxo-6-phenyl-2,3-dihydropyridazin-4-yl)amino]benzoic acid 5-Acetyl-2-ethyl-4-[(2-fluorophenyl)amino]-6-phenylpyridazin-3(2H)-one 4-(5-Acetyl-2-ethyl-3-oxo-6-phenyl-2,3-dihydropyridazin-4-ylamino)-benzoic acid ethyl ester 5-Acetyl-2-ethyl-4-[(4-fluorophenyl)amino]-6-phenylpyridazin-3(2H)-one 2-[(5-acetyl-2-ethyl-3-oxo-6-phenyl-2,3-dihydropyridazin-4-yl)amino]-4-fluorobenzoic acid 3-[(5-Acetyl-2-ethyl-3-oxo-6-phenyl-2,3-dihydropyridazin-4-yl)amino]benzonitrile 4-[(5-Acetyl-2-ethyl-3-oxo-6-phenyl-2,3-dihydropyridazin-4-yl)amino]-2-hydroxybenzoic acid 5-Acetyl-2-ethyl-4-[(3-hydroxy-4-methoxyphenyl)amino]-6-phenylpyridazin-3(2H)-one 4-[(5-Acetyl-2-ethyl-3-oxo-6-phenyl-2,3-dihydropyridazin-4-yl)amino]benzamide 5-Acetyl-2-ethyl-4-{[3-(methylthio)phenyl]amino}-6-phenylpyridazin-3(2H)-one 5-Acetyl-2-ethyl-4-[(3-methoxyphenyl)amino]-6-phenylpyridazin-3(2H)-one 5-Acetyl-4-[(3-acetylphenyl)amino]-2-ethyl-6-phenylpyridazin-3(2H)-one {4-[(5-Acetyl-2-ethyl-3-oxo-6-phenyl-2,3-dihydropyridazin-4-yl)amino]phenyl}acetic acid 5-Acetyl-4-[4-(tert-butylphenyl)amino]-2-ethyl-6-phenylpyridazin-3(2H)-one 4-[(5-Acetyl-2-ethyl-3-oxo-6-phenyl-2,3-dihydropyridazin-4-yl)amino]benzenesulphonamide 4-{4-[(5-Acetyl-2-ethyl-3-oxo-6-phenyl-2,3-dihydropyridazin-4-yl)amino]phenyl}-4-oxobutanoic acid 3-[(5-Acetyl-2-ethyl-3-oxo-6-phenyl-2,3-dihydropyridazin-4-yl)amino]-N-butylbenzenesulphonamide 5-acetyl-2-ethyl-4-[(1-oxo-2,3-dihydro-1H-inden-5-yl)amino]-6-phenylpyridazin-3(2H)-one N-{4-[(5-Acetyl-2-ethyl-3-oxo-6-phenyl-2,3-dihydropyridazin-4-yl)amino]phenyl}acetamide The title compounds were synthesized from 5-acetyl-2-ethyl-4-nitro-6-phenylpyridazin-3(2H)-one (Dal Piaz, V et al, *J. Med. Chem.* 1997, 40, 1417) and the corresponding aniline following the procedure of Example 49. The ESI/MS data and HPLC retention times are summarized in Table 9.

TABLE 9

| EXAMPLE | ESI/MS m/e (M + H)+ | Retention Time (min) |
|---|---|---|
| 60 | 378 | 8.6 |
| 61 | 364 | 8.7 |
| 62 | 368 | 9.3 |
| 63 | 413 | 9.5 |
| 64 | 402 | 9.6 |
| 65 | 398 | 9.2 |
| 66 | 350 | 8.0 |
| 67 | 378 | 8.0 |
| 68 | 352 | 8.9 |
| 69 | 406 | 9.3 |
| 70 | 352 | 8.8 |
| 71 | 396 | 9.1 |
| 72 | 359 | 8.5 |
| 73 | 394 | 8.3 |
| 74 | 380 | 7.9 |
| 75 | 377 | 7.3 |
| 76 | 380 | 9.4 |
| 77 | 364 | 8.9 |
| 78 | 376 | 8.5 |
| 79 | 392 | 8.0 |
| 80 | 390 | 10.4 |
| 81 | 413 | 7.5 |
| 82 | 434 | 8.0 |
| 83 | 469 | 9.2 |
| 84 | 388 | 8.3 |
| 85 | 391 | 7.6 |

Example 86

4-[5-Acetyl-6-(3-chlorophenyl)-2-ethyl-3-oxo-2,3-dihydropyridazin-4-ylamino]benzoic acid Obtained (35%) from 5-acetyl-2-ethyl-4-nitro-6-(3-chlorophenyl)pyridazin-3(2H)-one (Dal Piaz, V et al, *J. Med. Chem.* 1997, 40, 1417) and 4-aminobenzoic acid following the procedure of Example 49.

m.p. 207.0-207.9 δ(CDCl$_3$): 1.46 (t, 3H), 1.85. (s, 3H), 4.31 (q, 2H), 7.10 (d, 2H), 7.23 (m, 2H), 7.40 (m, 2H), 8.04 (d, 2H), 8.48 (s, 1H).

Example 87

5-Acetyl-6-(3-chlorophenyl)-4-[(3-chlorophenyl)amino]-2-ethylpyridazin-3(2H)-one Obtained from 5-acetyl-2-ethyl-4-nitro-6-(3-chlorophenyl)pyridazin-3(2H)-one (Dal Piaz, V et al, *J. Med. Chem.* 1997, 40, 1417) and 3-chloroaniline following the procedure of Example 49.

LRMS: m/Z 403 (M+1)+ Retention Time: 10.0 min

Example 88

5-Acetyl-6-(3-chlorophenyl)-2-ethyl-4-[(3-fluorophenyl)amino]pyridazin-3(2H)-one Obtained from 5-acetyl-2-ethyl-4-nitro-6-(3-chlorophenyl)pyridazin-3(2H)-one (Dal Piaz, V et al, *J. Med. Chem.* 1997, 40, 1417) and 3-fluoroaniline following the procedure of Example 49.

LRMS: m/Z 386 (M+1)+ Retention Time: 9.6 min

Example 89

5-Acetyl-4-[(3-chlorophenyl)amino]-2-ethyl-6-(4-fluorophenyl)pyridazin-3(2H)-one Obtained (71%) from the title compound of Preparation 31 and 3-chloroaniline following the procedure of Example 49.

m.p. 190.9-191.4 δ(CDCl$_3$): 1.45 (t, 3H), 1.75 (s, 3H), 4.29 (q, 2H), 6.97 (d,1H), 7.01 (m, 4H), 7.26 (m, 1H), 7.36 (m, 2H), 8.17 (s, 1H).

Example 90

5-Acetyl-4-[(3-bromophenyl)amino]-2-ethyl-6-(3-fluorophenyl)pyridazin-3(2H)-one

Obtained (85%) from the title compound of Preparation 32 and 3-bromoaniline following the procedure of Example 49.

m.p. 169.0-170.7 δ(CDCl$_3$): 1.45 (t, 3H), 1.77 (s, 3H), 4.29 (q, 2H), 7.01-7.38 (m, 8H), 8.22 (s, 1H).

Example 91

5-Acetyl-2-ethyl-4-[(3-fluorophenyl)amino]-6-(3-fluorophenyl)pyridazin-3(2H)-one Obtained (84%) from the title compound of Preparation 32 and 3-fluoroaniline following the procedure of Example 49.

m.p. 173.5-174.6 δ(CDCl$_3$): 1.45 (t, 3H), 1.78 (s, 3H), 4.30 (q, 2H), 6.78 (m, 1H), 6.89 (m, 2H), 7.11 (m, 3H), 7.27 (m, 1H), 7.38 (m, 1H), 8.21 (s, 1H).

Example 92

5-Acetyl-4-[(3-chlorophenyl)amino]-2-ethyl-6-(3-fluorophenyl)pyridazin-3(2H)-one Obtained from the title compound of Preparation 32 and 3-chloroaniline following the procedure of Example 49.

LRMS: m/Z 386 (M+1)$^+$ Retention Time: 9.5 min

Example 93

5-Acetyl-4-[(3-chlorophenyl)amino]-2-ethyl-3-nitrophenyl)pyridazin-3(2H)-one

Obtained (83%) from 5-acetyl-2-ethyl-4-nitro-6-(3-nitrophenyl)pyridazin-3(2H)-one (Dal Piaz, V et al., *J. Med. Chem.* 1997, 40, 1417) and 3-chloroaniline following the procedure of Example 49.

m.p. 173.0-174.2° C. δ(CDCl$_3$): 1.46 (t, 3H), 1.81 (s, 3H), 4.31 (q, 2H), 6.99 (d, 1H), 7.09 (s, 1H), 7.17 (m, 1H), 7.27 (m, 1H), 7.60 (m, 2H), 8.18 (s, 1H), 8.26 (m, 2H).

Examples 94-97

5-Acetyl-2-ethyl-4-[(3-fluorophenyl)amino]-6-(3-nitrophenyl)pyridazin-3(2H)-one

4-{[5-Acetyl-2-ethyl-6-(3-nitrophenyl)-3-oxo-2,3-dihydropyridazin-4-yl]amino}benzoic acid 5-Acetyl-4-[(3-bromophenyl)amino]-2-ethyl-6-(3-nitrophenyl)pyridazin-3(2H)-one 5-Acetyl-2-ethyl-4-(naphthalen-1-ylamino)-6-(3-nitrophenyl)pyridazin-3(2H)-one The title compounds were synthesized from 5-acetyl-2-ethyl-4-nitro-6-(3-nitrophenyl)pyridazin-3(2H)-one (Dal Piaz, V et al, *J. Med. Chem.* 1997, 40, 1417) and the corresponding aniline following the procedure of Example 49. The ESI/MS data and HPLC retention times are summarized in Table 10.

TABLE 10

| EXAMPLE | ESI/MS m/e (M + H)$^+$ | Retention Time (min) |
|---|---|---|
| 94 | 397 | 9.0 |
| 95 | 423 | 8.1 |
| 96 | 458 | 9.5 |
| 97 | 429 | 9.6 |

Example 98

5-Butyryl-4-[(3-chlorophenyl)amino]-2-ethyl-6-phenylpyridazin-3(2H)-one

Obtained from the title compound of Preparation 33 and 3-chloroaniline following the procedure of Example 49.

LRMS: m/Z 396 (M+1)$^+$ Retention Time: 10.2 min

Example 99

5-Acetyl-4-[(3-chlorophenyl)amino]-6-phenyl-2-propylpyridazin-3(2H)-one

Obtained from 5-acetyl-4-nitro-6-phenyl-2-propylpyridazin-3(2H)-one (Dal Piaz, V. et al, *Drug Design and Discovery,* 1996, 14, 53-57) and 3-chloroaniline following the procedure of Example 49.

LRMS: m/Z 382 (M+1)$^+$ Retention Time: 9.8 min

Example 100

5-Acetyl-2-butyl-4-[(3-chlorophenyl)amino]-6-phenylpyridazin-3(2H)-one

Obtained from 5-acetyl-2-butyl-4-nitro-6-phenylpyridazin-3(2H)-one (Dal Piaz, V. et al, *Drug Design and Discovery,* 1996, 14, 53-57) and 3-chloroaniline following the procedure of Example 49.

LRMS: m/Z 396 (M+1)$^+$ Retention Time: 10.3 min

Example 101

5-Acetyl-4-[(3-bromophenyl)amino]-2-butyl-6-phenylpyridazin-3(2H)-one

Obtained from 5-acetyl-2-butyl-4-nitro-6-phenylpyridazin-3(2H)-one (Dal Piaz, V. et al., *Drug Design and Discovery,* 1996, 14, 53-57) and 3-bromoaniline following the procedure of Example 49.

LRMS: m/Z 441 (M+1)$^+$ Retention Time: 10.4 min

Example 102

5-Acetyl-4-N-(3,5-dichlorophenyl)-N-(3-fluorophenyl)amino]-2-ethyl-6-phenylpyridazin-3(2H)-one A mixture of the title compound of Example 3 (50 mg, 0.12 mmol), 3-fluorophenylboronic acid (33 mg, 0.24 mmol), anhydrous cupric acetate (182 mg, 0.18 mmol), triethylamine (0.034 ml, 0.24 mmol) and activated 4A molecular sieves (110 mg) in dry dichloromethane (2 ml) was stirred under the air at room temperature for 3 days. The reaction was filtered and the solvent removed under reduced pressure. The crude was purified by flash column chromatography ($SiO_2$, $CH_2Cl_2$-AcOEt) to yield the title compound (216 mg, 99% yield) as a solid.

$\delta(CDCl_3)$: 1.42 (m, 6H), 4.30 (q, 2H), 6.76 (m, 4H), 7.05 (m, 1H), 7.25 (m, 2H), 7.40 (m, 5H).

Examples 103-107

5-Acetyl-4-[bis(3-fluorophenyl)amino]-2-ethyl-6-phenylpyridazin-3(2H)-one

5-Acetyl-[bis(3-chlorophenyl)amino]-2-ethyl-6-phenylpyridazin-3(2)-one

5-Acetyl-2-ethyl-4-[bis(3-methylsulphanylphenyl)amino]-6-phenylpyridazin-3(2H)-one 5-Acetyl-4-[bis(3-acetylphenyl)amino]-2-ethyl-6-phenylpyridazin-3(2H)-one 5-Acetyl-4-[bis-(3,5-dichlorophenyl)amino]-2-ethyl-6-phenyl-2H-pyridazin-3-one The title compounds were synthesized from the title compound of Preparation 22 and an excess of the corresponding arylboronic acid following the experimental procedure described in example 1. The ESI/MS data and HPLC retention times are summarized in Table 11.

TABLE 11

| EXAMPLE | ESI/MS m/e $(M + H)^+$ | Retention Time (min) |
| --- | --- | --- |
| 103 | 446 | 10.0 |
| 104 | 479 | 10.7 |
| 105 | 502 | 10.6 |
| 106 | 494 | 9.0 |
| 107 | 549 | 22 |

Example 108 methyl 4-{N-(5-acetyl-2-ethyl-6-(4-methylsulphinylphenyl)-3-oxo-2,3-dihydropyridazin-4-yl)-N-[4-(methoxycarbonyl)phenyl]amino}benzoate Obtained from the title compound of Preparation 26 and 4-(methoxycarbonyl)phenylboronic acid following the procedure of Example 102.

LRMS: m/Z 588 $(M+1)^+$ Retention Time: 8.4 min

Example 109

5-Acetyl-2-cyclopropylmethyl-4-(3,5-difluoro-phenylamino)-6-phenyl-2H-pyridazin-3-one The title compound was synthesized from the title compound of Preparation 29 and 3,5-difluorophenylboronic acid following the procedure of Example 1.

LRMS: m/Z 396 $(M+1)^+$ Retention Time: 9.8 min

Example 110

5-Acetyl-4-(3-fluoro-phenylamino)-2-methyl-6-phenyl-2H-pyridazin-3-one

The title compound was synthesized from 5-acetyl-4-amino-2-methyl-6-phenylpyridazin-3(2H)-one (Dal Piaz, V., Ciciani, G, Giovannoni, M. P., Heterocycles, 1991, 32, 1173-9) and the corresponding 3-fluorophenylboronic acid following the procedure of Example 1.

LRMS: m/Z 338 $(M+1)^+$ Retention Time: 8.5 min

Example 111

4-5-Acetyl-2-methyl-3-oxo-6-phenyl-2,3-dihydro-pyridazin-4-ylamino)-benzoic acid A mixture of 5-acetylamino-2-methyl-6-phenylpyridazin-3(2H)-one (Dal Piaz, V., Ciciani, G, Giovannoni, M. P., Heterocycles, 1991, 32, 1173-9) (100 mg, 0.41 mmol), (4-methoxycarbonylphenyl)boronic acid (148 mg, 0.82 mmol), anhydrous cupric acetate (112 mg, 0.61 mmol), triethylamine (0.11 ml, 0.82 mmol) and activated molecular sieves (520 mg, 4 Å) in dry dichloromethane (4 ml) was stirred under air exposure at room temperature for 48 h. The reaction was filtered and the solvent removed under reduced pressure. The resulting residue was purified by flash column chromatography ($SiO_2$, dichloromethane-ethyl acetate). The product thus obtained was suspended in a 2:3 THF/MeOH mixture (7 ml), LiOH (50 mg, 1.2 mmol) was added and the mixture was stirred at room temperature for 3 days. Then the solvent was removed and the crude product was suspended in water and the solution was acidified with HCl 2N. Then it was extracted with dichloromethane and the combined organic layers were washed with brine and dried on $Na_2SO_4$. The solvent was removed to yield a product that was purified by preparative HPLC/MS to isolate the title compound.

LRMS: m/Z 364 $(M+1)^+$ Retention Time: 7.5 min

Example 112

5-Acetyl-4-(3,5-dichloro-phenylamino)-2,6-diphenyl-2H-pyridazin-3-one

Obtained as a solid (21%) from 5-acetyl-4-amino-2,6-diphenylpyridazin-3(2H)-one (Dal Piaz, V., Ciciani, G. Giovannoni, M. P., Heterocycles, 1991, 32, 1173-9) and 3,5-dichlorophenylboronic acid following the procedure of example 1.

LRMS: m/Z 452 $(M+1)^+$ $\delta$(DMSO-d6): 1.89 (s, 3H), 7.15 (s, 2H), 7.22 (s, 2H), 7.40 (m, 6H), 7.52 (m, 2H), 7.66 (d, 2H), 9.27 (bs, 1H).

Example 113

5-Acetyl-4-(3-fluoro-phenylamino)-2,6-diphenyl-2H-pyridazin-3-one

Obtained as a solid (57%) from 5-acetyl-4-amino-2,6-diphenylpyridazin-3(2H)-one (Dal Piaz, V., Cidani, G, Giovannoni, M. P., Heterocycles, 1991, 32, 1173-9) and 3-fluorophenylboronic acid following the procedure of example 1.

LRMS:, m/Z 401 (M+1)$^+$ δ(DMSO-d6): 1.80 (s, 3H), 6.91 (m, 3H), 7.32 (q, 1H), 7.36 (m, 6H), 7.53 (t, 2H), 7.67 (d, 2H), 9.22 (s, 1H).

Example 114

5-Acetyl-4-(naphthalen-1-ylamino)-2,6-diphenyl-2H-pyridazin-3-one

Obtained as a solid (20%) from 5-acetyl-4-amino-2,6-diphenylpyridazin-3(2H)-one (Dal Piaz, V., Ciciani, G. Giovannoni, M. P., Heterocycles, 1991, 32, 1173-9) and 1-naftalenboronic acid following the procedure of example 1.

LRMS: m/Z 433 (M+1)$^+$ δ(DMSO-d6): 1.23 (s, 2H), 7.26-7.56 (m, 11H), 7.73 (dd, 2H), 7.80 (dd, 2H), 7.94 (dd, 1H), 8.03 (dd, 1H), 9.25 (s, 1H).

Example 115

5-Acetyl-4-(3,5-difluoro-phenylamino)-2,6-diphenyl-2H-pyridazin-3-one

Obtained as a solid (26%) from 5-acetyl-4-amino-2,6-diphenylpyridazin-3(2H)-one (Dal Piaz, V., Ciciani, G. Giovannoni, M. P., Heterocycles, 1991, 32, 1173-9) and 3,5-difluorophenylboronic acid following the procedure of example 1.

LRMS: m/Z 419 (M+1)$^+$ δ(DMSO-d6): 1.91 (s, 3H), 6.82 (m, 3H), 7.47 (m, 6H), 7.53 (t, 2H), 7.65 (d, 2H), 9.28 (s, 1H).

Example 116

5-Acetyl-4-(3-chloro-phenylamino)-2,6-diphenyl-2H-pyridazin-3-one

Obtained as a solid (61%) from 5-acetyl-4-amino-2,6-diphenylpyridazin-3(2H)-one (Dal Piaz, V., Ciciani, G, Giovannoni, M. P., *Heterocycles*, 1991, 32, 1173-9) and 3-chlorophenylboronic acid following the procedure of example 1.

LRMS: m/Z 417 (M+1)$^+$ δ(DMSO-d6): 1.78 (s, 2H), 7.12 (t, 2H), 7.16 (s, 1H), 7.25 (t, 1H), 7.35 (m, 6H), 7.54 (t, 2H), 7.67 (d, 2H), 9.22 (s, 1H).

Example 117

4-(3-Chloro-phenylamino)-2-ethyl-6-phenyl-5-(1-phenyl-methanoyl)pyridazin-2H-one The title compound was synthesized from the title compound of Preparation 35 and 3,5-difluorophenylboronic acid following the procedure of Example 1.

LRMS: m/Z 396 (M+1)$^+$ Retention Time: 9.8 min

Example 118

5-[(3-Chlorophenyl)amino]-1-ethyl-6-oxo-3-phenyl-1,6-dihydropyridazine-4-carbaldehyde The title compound was synthesized from the title compound of Preparation 36 and 3-chlorophenylboronic acid following the procedure of Example 1.

LRMS: m/Z 354 (M+1)$^+$ Retention Time: 9.9 min

Example 119

Methyl 5-[(3-chlorophenyl)amino]-1-ethyl-6-oxo-3-phenyl-1,6-dihydropyridazine-4-carboxylate The title compound was synthesized from the title compound of Preparation 39 and 3-chlorophenylboronic acid following the procedure of Example 1.

LRMS: m/Z 384 (M+1)$^+$ Retention Time: 9.6 min

Example 120

4-[(3-Chlorophenyl)amino]-2-ethyl-6-phenyl-5-(3-phenylpropanoyl)pyridazin-3(2H)-one Obtained as a solid (21%) from the title compound of Preparation 43 and 3-chlorophenylboronic acid following the procedure of Example 1.

δ(CDCl$_3$): 1.44 (t, 3H), 2.20 (t, 2H), 2.35 (t, 2H), 4.30 (q, 2H), 6.74 (d, 2H), 7.00-7.45 (m, 12H), 8.03 (s, 1H).

Example 121

4-[(3,5-Dichlorophenyl)amino]-2-ethyl-6-phenyl-5-(3-phenylpropanoyl)pyridazin-3(2H)-one Obtained as a solid (36%) from the title compound of Preparation 43 and 3,5-dichlorophenylboronic acid following the procedure of Example 1.

δ(CDCl$_3$): 1.44 (t, 3H), 2.37 (m, 4H), 4.29 (q, 2H), 6.59 (m, 2H), 6.76 (m, 2H), 6.9 (s, 2H), 7.08-7.18 (m, 3H), 7.357.44 (m, 3H), 8.07 (s, 1H).

Example 122

3-{[2-Ethyl-3-oxo-6-phenyl-5-(3-phenylpropanoyl)-2,3-dihydropyridazin-4-yl]amino}benzonitrile Obtained as a solid (56%) from the title compound of Preparation 43 and 3-cyanophenylboronic acid following the procedure of Example 1.

δ(CDCl$_3$): 1.43 (t, 3H), 2.36 (m, 4H), 4.28 (q, 2H), 6.76 (m, 2H), 6.76 (m, 2H), 7.11-7.17 (m, 4H), 7.39-7.45 (m, 8H), 8.33 (s, 1H).

Example 123

4-{[2-Ethyl-3-oxo-6-phenyl-5-(3-phenylpropanoyl)-2,3-dihydropyridazin-4-yl]amino}benzoic acid Obtained as a solid from the title compound of Preparation 43 following the experimental procedure of Example 111.

LRMS: m/Z 468 (M+1)$^+$ Retention Time: 9.5 min

Example 124

4-[(3-Chlorophenyl)amino]-2-ethyl-6-phenyl-5-(3-thien-3-ylpropanoyl)pyridazin-3(2H)-one Obtained as a solid (33%) from the title compound of Preparation 44 and 3-chlorophenylboronic acid following the experimental procedure of Example 1.

LRMS: m/Z 464 (M+1)$^+$ Retention Time: 10.7 min

Example 125

4-[(3-Chlorophenyl)amino]-2-ethyl-6-phenyl-5-(3-pyridin-3-ylpropanoyl)pyridazin-3(2H)-one Obtained as a solid (30%) from the title compound of Preparation 45 and 3-chlorophenylboronic acid following the experimental procedure of Example 1.

LRMS: m/Z 459 (M+1)$^+$ Retention Time: 8.1 min

Example 126

5-Acetyl-2-benzyl-4-(1-naphthylamino)-6-phenylpyridazin-3(2H)-one

Obtained as a solid from the title compound of Preparation 28 and 1-naphthylboronic acid following the experimental procedure of Example 1.

LRMS: m/Z 446 (M+1)$^+$ Retention Time: 10.4 min

Example 127

4-[(5-Acetyl-2-benzyl-3-oxo-6-phenyl-2,3-dihydropyridazin-4-yl)amino]benzoic acid Obtained as a solid from the title compound of Preparation 28 following the experimental procedure of Example 111.

LRMS: m/Z 440 (M+1)$^+$ Retention Time: 8.1 min

Examples 128-129

5-Acetyl-4-[(3,5-difluorophenyl)amino]-6-phenyl-2-(pyridin-4-ylmethyl)pyridazin-3(2H)-one 5-Acetyl-4-[(3-chlorophenyl)amino]-6-phenyl-2-(pyridin-4-ylmethyl)pyridazin-3(2H)-one The title compounds were synthesized from the title compound of Preparation 30 and the corresponding boronic acid following the experimental procedure of Example 1. The ESI/MS data and HPLC retention times are summarized in Table 12.

TABLE 12

| EXAMPLE | ESI/MS m/e (M + H)$^+$ | Retention Time (min) |
|---|---|---|
| 128 | 433 | 8.3 |
| 129 | 431 | 8.5 |

Example 130

4[(5-Acetyl-3-oxo-2,6-diphenyl-2,3-dihydropyridazin-4-yl)amino]benzoic acid

Obtained as a solid from 5-acetyl-4-amino-2,6-diphenylpyridazin-3(2H)-one (Dal Piaz, V., Ciciani, G, Giovannoni, M. P., *Heterocycles,* 1991, 32, 1173-9) following the experimental procedure of Example 111.

LRMS: m/Z 426 (M+1)$^+$ Retention Time: 8.7 min

Examples 131-133

5-Acetyl-2-(cyclopropylmethyl)-4-[(2-fluorophenyl)amino]-6-phenylpyridazin-3(2H)-one 5-Acetyl-4-[(2-chlorophenyl)amino]-2-(cyclopropylmethyl)-6-phenylpyridazin-3(2H)-one 5-Acetyl-2-(cyclopropylmethyl)-4-{[4-(hydroxymethyl)phenyl]amino}-6-phenylpyridazin-3(2H)-one The title compounds were synthesized from the title compound of Preparation 29 and the corresponding boronic acid following the experimental procedure of Example 1. The ESI/MS data and HPLC retention times are summarized in Table 13.

TABLE 13

| EXAMPLE | ESI/MS m/e (M + H)$^+$ | Retention Time (min) |
|---|---|---|
| 131 | 378 | 9.5 |
| 132 | 394 | 9.9 |
| 133 | 390 | 8.6 |

Example 134

3-{[5-Acetyl-2-(cyclopropylmethyl)-3-oxo-6-phenyl-2,3-dihydropyridazin-4-yl]amino}benzonitrile Obtained as a solid (40%) from the title compound of Preparation 29 and 3-cyanophenylboronic acid following the procedure of Example 1.

m.p. 212.9-214.0° C. δ(DMSO-d$_6$): 0.42-0.53 (m, 4H), 1.33 (m, I H), 1.82 (s, 3H), 4.02 (d, 2H), 7.34-7.46 (m, 9H), 9.17 (m, 1H).

Example 135

4-{[5-Acetyl-2-(cyclopropylmethyl)-3-oxo-6-phenyl-2,3-dihydropyridazin-4-yl]amino}benzoic acid Obtained as a solid (29%) from the title compound of Preparation 29 following the procedure of Example 111.

m.p. 250.7-251.6° C. δ(DMSO-d$_6$): 0.43-0.53 (m, 4H), 1.33 (m,1H), 1.85 (s, 3H), 4.02 (d, 2H), 7.05 (d, 2H), 7.33 (m, 2H), 7.42 (m, 3H), 7.79 (d, 2H), 9.21 (s, 1H); 12.8 (bs, 1H).

Example 136

5-Acetyl-2-isopropyl-4-(1-naphthylamino)-6-phenylpyridazin-3(2H)-one

Obtained as a solid (23%) from the title compound of Preparation 47 and 1-naphthaleneboronic acid following the procedure of Example 1.

m.p. 246.3-246.9° C. δ(CDCl$_3$): 1.31 (s, 3H), 1.47 (d, 6H), 5.42 (m, 1H), 7.22 (m, $_1$ H), 7.35 (m, 6H), 7.55 (m, 2H), 7.75 (d, 1H), 7.87 (m, 1H), 8.01 (d, 1H), 8.19 (s, 1H).

Example 137

5-Acetyl-4-[(3,5-difluorophenyl)amino]-2-isopropyl-6-phenylpyridazin-3(2H)-one

Obtained as a solid (54%) from the title compound of Preparation 47 and 3,5-difluorophenylboronic acid following the procedure of Example 1.

m.p. 200.9-201.6° C. δ(CDCl₃): 1.43 (d, 6H), 1.82 (s, 3H), 5.32 (m, 1H), 6.56 (m, 3H), 7.42 (m, 5H), 8.20 (s, 1H).

Example 138

5-Acetyl-4-[(3-fluorophenyl)amino]-2-isopropyl-6-phenylpyridazin-3(2H)-one

Obtained as a solid (41%) from the title compound of Preparation 47 and 3-fluorophenylboronic acid following the procedure of Example 1.

m.p. 173.1-173.5° C. δ(CDCl₃): 1.43 (d, 6H), 1.76 (s, 3H), 5.34 (m, 1H), 6.76 (m, 1H), 6.86 (m, 2H), 7.22 (m, 1H), .7.38 (m, 5H), 8.17 (s, 1H).

Example 139

5-Acetyl-4-[(3-chlorophenyl)]amino-3-2-isopropyl-6-phenylpyridazin-3(2H)-one

Obtained as a solid (80%) from the title compound of Preparation 47 and 3-chlorophenylboronic acid following the procedure of Example 1.

m.p. 191.7-192.2° C. δ(CDCl₃): 1.43 (d, 6H), 1.75 (s, 3H), 5.34 (m, 1H), 6.96 (m, 1H), 7.03 (m, 1H), 7.15 (m, 1H), 7.25 (m, 1H), 7.38 (m, 5H), 8.17 (s, 1H).

Example 140

5-Acetyl-4-[(3,5-dichlorophenyl)amino]-2-isopropyl-6-phenylpyridazin-3(2H)-one

Obtained as a solid (79%) from the title compound of Preparation 47 and 3,5-dichlorophenylboronic acid following the procedure of Example 1.

m.p. 201.1-202.3° C. δ(CDCl₃): 1.43 (d, 6H), 1.79 (s, 3H), 5.35 (m, 1H), 6.93 (s, 2H), 7.13 (s, 1H), 7.41 (m, 5H), 8.21 (s, 1H).

Example 141

4[(5-Acetyl-2-isopropyl-3-oxo-6-phenyl-2,3-dihydropyridazin-4-yl)amino]benzoic acid Obtained as a solid (23%) from the title compound of Preparation 47 following the procedure of Example 111.

m.p. 266.6-267.5° C. δ(DMSO-d₃): 1.34 (d, 6H), 1.86 (s, 3H), 5.23 (m, 1H), 7.03 (d, 2H), 7.32 (m, 2H), 7.42 (m, 3H), 7.79 (d, 2H), 9.17 (s, 1H), 12.71 (s, 1H).

Examples 142-145

5-Acetyl-4-[(2-fluorophenyl)amino]-2-isopropyl-6-phenylpyridazin-3(2H)-one

5-Acetyl-4-[(2-chlorophenyl)amino]-2-isopropyl-6-phenylpyridazin-3(2H)-one

3-[(5-Acetyl-2-isopropyl-3-oxo-6-phenyl-2,3-dihydropyridazin-4-yl)amino]benzonitrile 5-Acetyl-4-{4-(hydroxymethyl)phenyl]amino}-2-isopropyl-6-phenylpyridazin-3(2H)-one The title compounds were synthesized from the title compound of Preparation 47 and the corresponding boronic acid following the experimental procedure of Example 1. The ESI/MS data and HPLC retention times are summarized in Table 14.

TABLE 14

| EXAMPLE | ESI/MS m/e (M + H)⁺ | Retention Time (min) |
|---|---|---|
| 142 | 366 | 9.6 |
| 143 | 382 | 10.0 |
| 144 | 373 | 9.2 |
| 145 | 378 | 8.6 |

Examples 146-150

5-Acetyl-4-[(2-fluorophenyl)amino]-2-(2-hydroxyethyl)-6-phenylpyridazin-3(2H)-one 5-Acetyl-4-[(2-chlorophenyl)amino]-2-(2-hydroxyethyl)-6-phenylpyridazin-3(2H)-one 3-{[5-Acetyl-2-(2-hydroxyethyl)-3-oxo-6-phenyl-2,3-dihydropyridazin-4-yl]amino}benzonitrile 5-Acetyl-2-(2-hydroxyethyl)-4-{[4-(hydroxymethyl)phenyl]amino}-6-phenylpyridazin-3(2H)-one 5-Acetyl-4-[(3-chlorophenyl)amino]-2-(2-hydroxyethyl)-6-phenylpyridazin-3(2H)-one The title compounds were synthesized from the title compound of Preparation 49 and the corresponding boronic acid following the procedure of Example 1. The ESI/MS data and HPLC retention times are summarized in Table 15.

TABLE 15

| EXAMPLE | ESI/MS m/e (M + H)⁺ | Retention Time (min) |
|---|---|---|
| 146 | 368 | 7.8 |
| 147 | 384 | 8.3 |
| 148 | 375 | 7.5 |
| 149 | 380 | 6.5 |
| 150 | 384 | 8.5 |

Examples 151-155

5-Acetyl-6-(3-fluorophenyl)-4-[(2-fluorophenyl)amino]-2-(2-hydroxyethyl)pyridazin-3(2H)-one 5-Acetyl-4-[(2-chlorophenyl)amino]-6-(3-fluorophenyl)-2-(2-hydroxyethyl)pyridazin-3(2H)-one 3-{[5-Acetyl-6-(3-fluorophenyl)-2-(2-hydroxyethyl)-3-oxo-2,3-dihydropyridazin-4-yl]amino}benzonitrile 5-Acetyl-6-(3-fluorophenyl)-2-(2-hydroxyethyl)4-{[4-(hydroxymethyl)phenyl]amino}pyridazin-3(2H)-one 5-Acetyl-4-[(3-chlorophenyl)amino]-6-(3-fluorophenyl)-2-(2-hydroxyethyl)pyridazin-3(2H)-one The title compounds were synthesized from the title compound of Preparation 51 and the corresponding boronic acid following the experimental procedure of Example 1. The ESI/MS data and HPLC retention times are summarized in Table 16.

TABLE 16

| EXAMPLE | ESI/MS m/e (M + H)+ | Retention Time (min) |
|---|---|---|
| 151 | 386 | 8.1 |
| 152 | 402 | 8.5 |
| 153 | 393 | 7.8 |
| 154 | 398 | 6.8 |
| 155 | 402 | 8.7 |

Examples 156-160

3-{[5-Acetyl-6-(3-chlorophenyl)-2-cyclopropylmethyl)-3-oxo-2,3-dihydropyridazin-4-yl]amino}benzamide 5-Acetyl-6-(3-chlorophenyl)-2-(cyclopropylmethyl)-4-{[4-(hydroxymethyl)phenyl]amino}pyridazin-3(2H)-one 3-{[5-Acetyl-6-(3-chlorophenyl)-2-(cyclopropylmethyl)-3-oxo-2,3-dihydropyridazin-4-yl]amino}benzonitrile 5-Acetyl-6-(3-chlorophenyl)-2-cyclopropylmethyl)-4-[(2-fluorophenyl)amino]pyridazin-3(2H)-one 5-Acetyl-6-(3-chlorophenyl)-4-[(3-chlorophenyl)amino]-2-(cyclopropylmethyl)pyridazin-3(2H)-one The title compounds were synthesized from the title compound of Preparation 53 and the corresponding aniline following the experimental procedure of Example 49. The mixture was stirred at room temperature overnight. The ESI/MS data and HPLC retention times are summarized in Table 17.

TABLE 17

| EXAMPLE | ESI/MS m/e (M + H)+ | Retention Time (min) |
|---|---|---|
| 156 | 437 | 9.0 |
| 157 | 424 | 9.3 |
| 158 | 419 | 9.8 |
| 159 | 412 | 10.2 |
| 160 | 429 | 10.6 |

Examples 161-162

3-{[5-Acetyl-2-(cyclopropylmethyl)-6-(3-fluorophenyl)-3-oxo-2,3-dihydropyridazin-4-yl]amino}benzamide 5-Acetyl-2-(cyclopropylmethyl)-6-(3-fluorophenyl)-4-{[4-(hydroxymethyl)phenyl]amino}pyridazin-3(2H)-one The title compounds were synthesized from the title compound of Preparation 55 and the corresponding aniline following the experimental procedure of Example 49. The mixture was stirred at room temperature overnight. The ESI/MS data and HPLC retention times are summarized in Table 18.

TABLE 18

| EXAMPLE | ESI/MS m/e (M + H)+ | Retention Time (min) |
|---|---|---|
| 161 | 421 | 8.4 |
| 162 | 408 | 8.8 |

Examples 163-168

3-{[5-Acetyl-6-(3-fluorophenyl)-2-isopropyl-3-oxo-2,3-dihydropyridazin-4-yl]amino}benzamide 5-Acetyl-6-(3-fluorophenyl)-4-{[4-(hydroxymethyl)phenyl]amino}-2-isopropylpyridazin-3(2H)-one 3-{[5-Acetyl-6-(3-fluorophenyl)-2-isopropyl-3-oxo-2,3-dihydropyridazin-4-yl]amino}benzonitrile 5-Acetyl-6-(3-fluorophenyl)-4-[(2-fluorophenyl)amino]-2-isopropylpyridazin-3(2H)-one 5-Acetyl-4-[(3-chlorophenyl)amino]-6-(3-fluorophenyl)-2-isopropylpyridazin-3(2H)-one 5-Acetyl-4-[(2-chlorophenyl)amino]-6-(3-fluorophenyl)-2-isopropylpyridazin-3(2H)-one The title compounds were synthesized from the tile compound of Preparation 57 and the corresponding aniline following the experimental procedure of Example 49. The mixture was stirred at room temperature overnight. The ESI/MS data and HPLC retention times are summarized in Table 19.

TABLE 19

| EXAMPLE | ESI/MS m/e (M + H)+ | Retention Time (min) |
|---|---|---|
| 163 | 409 | 8.4 |
| 164 | 396 | 8.8 |
| 165 | 391 | 9.3 |
| 166 | 383 | 9.7 |
| 167 | 400 | 10.1 |
| 168 | 400 | 10.1 |

Examples 169-170

3-{[5-Acetyl-2-(cyclopropylmethyl)-6-(4-fluorophenyl)-3-oxo-2,3-dihydropyridazin-4-yl]amino}benzonitrile 3-{[5-Acetyl-2-(cyclopropylmethyl)-6-(4-fluorophenyl)-3-oxo-2,3-dihydropyridazin-4-yl]amino}benzamide The title compounds were synthesized from the title compound of Preparation 59 and the corresponding aniline following the experimental procedure of Example 49. The mixture was stirred at room temperature overnight. The ESI/MS data and HPLC retention times are summarized in Table 20.

TABLE 20

| EXAMPLE | ESI/MS m/e (M + H)+ | Retention Time (min) |
|---|---|---|
| 169 | 403 | 9.4 |
| 170 | 421 | 8.4 |

Examples 171-175

3-{[5-Acetyl-6-(3-chlorophenyl)-2-ethyl-3-oxo-2,3-dihydropyridazin-4-yl]amino}benzamide 5-Acetyl-6-(3-chlorophenyl)-2-ethyl-4-{[4-(hydroxymethyl)phenyl]amino}pyridazin-3(2H)-one 3-{[5-Acetyl-6-(3-chlorophenyl)-2-ethyl-3-oxo-2,3-dihydropyridazin-4-yl]amino}benzonitrile 5-Acetyl-6-(3-chlorophenyl)-2-ethyl-4-[(2-fluorophenyl)amino]pyridazin-3(2H)-one 5-Acetyl-6-(3-chlorophenyl)-4-[(2-chlorophenyl)amino]-2-ethylpyridazin-3(2H)-one The title compounds were synthesized from 5-acetyl-2-ethyl-4-nitro-6-(3-chlorophenyl)pyridazin-3(2H)-one (Dal Piaz, V et al, *J. Med. Chem.* 1997, 40, 1417) and the corresponding aniline following the experimental procedure of Example 49. The mixture was stirred at room temperature overnight. The ESI/MS data and HPLC retention times are summarized in Table 21.

TABLE 21

| EXAMPLE | ESI/MS m/e (M + H)+ | Retention Time (min) |
|---|---|---|
| 171 | 411 | 8.3 |
| 172 | 398 | 8.6 |
| 173 | 393 | 9.3 |
| 174 | 386 | 9.6 |
| 175 | 403 | 10.1 |

Example 176

5-Acetyl-2-ethyl-6-(3-fluorophenyl)-4-{[4-(hydroxymethyl)phenyl]amino}pyridazin-3(2H)-one Obtained (50%) from the title compound of Preparation 32 and 4-aminophenylmethanol following the procedure of Example 49. The mixture was stirred at room temperature overnight and the final product was purified by flash column chromatography (SiO$_2$, hexane-ethyl acetate)

m.p. 161.0-162.1 δ(CDCl$_3$): 1.44 (t, 3H), 1.73 (s, 3H), 4.29 (q, 2H), 4.67 (s, 2H), 7.10 (m, 5H), 7.33 (m, 3H), 8.20 (s, 1H).

Examples 177-180

3-{[5-Acetyl-2-ethyl-6-(3-fluorophenyl)-3-oxo-2,3-dihydropyridazin-4-yl]amino}benzamide 3-{[5-Acetyl-2-ethyl-6-(3-fluorophenyl)-3-oxo-2,3-dihydropyridazin-4-yl]amino}benzonitrile 5-Acetyl-2-ethyl-6-(3-fluorophenyl)-4-[(2-fluorophenyl)amino]pyridazin-3(2H)-one 5-Acetyl-4-[(2-chlorophenyl)amino]-2-ethyl-6-(3-fluorophenyl)pyridazin-3(2H)-one The title compounds were synthesized from the title compound of Preparation 32 and the corresponding aniline following the experimental procedure of Example 49. The mixture was stirred at room temperature overnight. The ESI/MS data and HPLC retention times are summarized in Table 22.

TABLE 22

| EXAMPLE | ESI/MS m/e (M + H)+ | Retention Time (min) |
|---|---|---|
| 177 | 395 | 7.7 |
| 178 | 377 | 8.8 |
| 179 | 370 | 9.1 |
| 180 | 386 | 9.5 |

Example 181

5-Acetyl-2-ethyl-6-(4-fluorophenyl)-4-{[4-(hydroxymethyl)phenyl]amino}pyridazin-3(2H)-one Obtained (43%) from the title compound of Preparation 31 and 4-aminophenylmethanol following the procedure of Example 49. The mixture was stirred at room temperature overnight and the final product was purified by flash column chromatography (SiO$_2$, hexane-ethyl acetate)

m.p. 154.3-156.0 δ(CDCl$_3$): 1.44 (t, 3H), 1.71 (s, 3H), 4.29 (q, 2H), 4.67. (s, 2H), 7:08 (m, 4H), 7.33 (m, 4H), 8.16 (s, 1H).

Example 182

4-{[-Acetyl-2-ethyl-6-(4-fluorophenyl)-3-oxo-2,3-dihydropyridazin-4-yl]amino}benzonitrile Obtained (80%) from the title compound of Preparation 31 and 4-aminobenzonitrile following the procedure of Example 49. The mixture was stirred at room temperature overnight.

m.p. 207.3-208.4 δ(CDCl$_3$): 1.44 (t, 3H), 1.86 (s, 3H), 4.29 (q, 2H), 7.06-7.16 (m, 4H), 7.40 (m, 1H), 7.57 (m, 1H), 7.59 (m, 1H), 7.70 (m, 1H), 8.55 (s, 1H).

Examples 183-186

3-{[5-Acetyl-2-ethyl-6-(4-fluorophenyl)-3-oxo-2,3-dihydropyridazin-4-yl]amino}benzamide 3-{[5-Acetyl-2-ethyl-6-(4-fluorophenyl)-3-oxo-2,3-dihydropyridazin-4-yl]amino}benzonitrile 5-Acetyl-2-ethyl-6-(4-fluorophenyl)-4-[(2-fluorophenyl)amino]pyridazin-3(2H)-one 5Acetyl-4-[(2-chlorophenyl)amino]-2-ethyl-6-(4-fluorophenyl)pyridazin-3(2H)-one The title compounds were synthesized from the title compound of Preparation 31 and the corresponding aniline following the experimental procedure of Example 49. The mixture was stirred at room temperature overnight. The ESI/MS data and HPLC retention times are summarized in Table 23.

TABLE 23

| EXAMPLE | ESI/MS m/e (M + H)+ | Retention Time (min) |
|---|---|---|
| 183 | 395 | 7.6 |
| 184 | 377 | 8.7 |
| 185 | 370 | 9.0 |
| 186 | 386 | 9.4 |

Example 187

5-Acetyl-4-[(3-chlorophenyl)amino]-2-ethyl-6-(1-naphthyl)pyridazin-3(2H)-one

Obtained as a solid (83%) from the title compound of Preparation 63 and 3-chlorophenylboronic acid following the procedure of Example. 1.
LRMS: m/Z 418 (M+1)+ Retention Time: 10.0 min Examples 188-227

5-Acetyl-4-[(2,4-difluorophenyl)amino]-2-ethyl-6-phenylpyridazin-3(2H)-one

5-Acetyl-4-[(3,4-dichlorophenyl)amino]-2-ethyl-6-phenylpyridazin-3(2H)-one

5-Acetyl-4-[(3-chloro-4-fluorophenyl)amino]-2-ethyl-6-phenylpyridazin-3(2H)-one

5-Acetyl-4-[(2-chloro-6-methylphenyl)amino]-2-ethyl-6-phenylpyridazin-3(2H)-one

5-Acetyl-2-ethyl-4-[(5-fluoro-2-methylphenyl)amino]-6-phenylpyridazin-3(2H)-one

5-Acetyl-2-ethyl-4-[(2-methyl-5-nitrophenyl)amino]-6-phenylpyridazin-3(2H)-one

5-Acetyl-4-[(2,3-dimethylphenyl)amino]-2-ethyl-6-phenylpyridazin-3(2H)-one

5-Acetyl-4-[(2,6-difluorophenyl)amino]-2-ethyl-6-phenylpyridazin-3(2H)-one

5-Acetyl-4-[(2,5-dimethylphenyl)amino]-2-ethyl-6-phenylpyridazin-3(2H)-one

5-Acetyl-4-[(2,5-difluorophenyl)amino]-2-ethyl-6-phenylpyridazin-3(2H)-one

5-Acetyl-2-ethyl-4-[(2-fluoro-5-nitrophenyl)amino]-6-phenylpyridazin-3(2H)-one

5-Acetyl-2-ethyl-4-[(3-fluoro-4-methylphenyl)amino]-6-phenylpyridazin-3(2H)-one

5-Acetyl-4-[(3,4-difluorophenyl)amino]-2-ethyl-6-phenylpyridazin-3(2H)-one

5-Acetyl-4-[(2-bromophenyl)amino]-2-ethyl-6-phenylpyridazin-3(2H)-one

5-Acetyl-4-[(2,3-difluorophenyl)amino]-2-ethyl-6-phenylpyridazin-3(2H)-one

5-Acetyl-4-[(5-chloro-2-methylphenyl)amino]-2-ethyl-6-phenylpyridazin-3(2H)-one

5-Acetyl-4-[(2-chloro-5-methylphenyl)amino]-2-ethyl-6-phenylpyridazin-3(2H)-one

4-[(5-Acetyl-2-ethyl-3-oxo-6-phenyl-2,3-dihydropyridazin-4-yl)amino]-3-methylbenzoic acid 5-Acetyl-4-[(2,4-dichlorophenyl)amino]-2-ethyl-6-phenylpyridazin-3(2H)-one 4-[(5-Acetyl-2-ethyl-3-oxo-6-phenyl-2,3-dihydropyridazin-4-yl)amino]-2-chlorobenzoic acid 5-Acetyl-4-[(2-chloro-5-nitrophenyl)amino]-2-ethyl-6-phenylpyridazin-3(2H)-one 5-Acetyl-2-ethyl-4-[(7-hydroxy-1-naphthyl)amino]-6-phenylpyridazin-3(2H)-one 5-Acetyl-2-ethyl-4-[(2-hydroxy-4-methylphenyl)amino]-6-phenylpyridazin-3(2H)-one 5-Acetyl-2-ethyl-4-[(2-hydroxy-4-nitrophenyl)amino]-6-phenylpyridazin-3(2H)-one 5-Acetyl-2-ethyl-4-[(2-hydroxy-5-methylphenyl)amino]-6-phenylpyridazin-3(2H)-one 5-Acetyl-2-ethyl-4-[(2-hydroxy-5-nitrophenyl)amino]-6-phenylpyridazin-3(2H)-one 5-Acetyl-2-ethyl-4-[(2-methoxy-4-nitrophenyl)amino]-6-phenylpyridazin-3(2H)-one 5-Acetyl-2-ethyl-6-phenyl-4-{[4-trifluoromethoxy)phenyl]amino}pyridazin-3(2H)-one 5-Acetyl-4-[(3-ethoxyphenyl)amino]-2-ethyl-6-phenylpyridazin-3(2H)-one 5-Acetyl-2-ethyl-4-[(2-methoxy-5-methylphenyl)amino]-6-phenylpyridazin-3(2H)-one 4-[(5-Acetyl-2-ethyl-3-oxo-6-phenyl-2,3-dihydropyridazin-4-yl)amino]-1-naphthonitrile 3-[(5-Acetyl-2-ethyl-3-oxo-6-phenyl-2,3-dihydropyridazin-4-yl)amino]-5-nitrobezoic acid 5-Acetyl-2-ethyl-4-[(3-mercaptophenyl)amino]-6-phenylpyridazin-3(2H)-one 5-Acetyl-4-[(2-chloro-5-methoxyphenyl)amino]-2-ethyl-6-phenylpyridazin-3(2H)-one 4-[(5-Acetyl-2-ethyl-3-oxo-6-phenyl-2,3-dihydropyridazin-4-yl)amino]-3-methoxybenzoic acid 5-Acetyl-2-ethyl-4-{[3-(1-hydroxyethyl)phenyl]amino}-6-phenylpyridazin-3(2H)-one 5-Acetyl-2-ethyl-4-{[3-(hydroxymethyl)phenyl]
amino}-6-phenylpyridazin-3(2H)-one 4-[(5-Acetyl-2-ethyl-3-oxo-6-phenyl-2,3-dihydropy-
ridazin-4-yl)amino]-3-hydroxybenzoic acid 5-Acetyl-2-ethyl-4-{[4-(1-hydroxyethyl)phenyl]
amino}-6-phenylpyridazin-3(2H)-one 5-Acetyl-4-[(3,5-dimethoxyphenyl)amino]-2-ethyl-
6-phenylpyridazin-3(2H)-one The title compounds were synthesized from 5-acetyl-2-ethyl-4-nitro-phenylpyridazin-3(2H)-one (Dal Piaz, V et al., *J. Med. Chem.* 1997, 40, 1417) and the corresponding aniline following the procedure of Example 49. The ESI/MS data and HPLC retention times are summarized in Table 24.

TABLE 24

| EXAMPLE | ESI/MS m/e (M + H)+ | Retention Time (min) |
|---|---|---|
| 188 | 370 | 9.1 |
| 189 | 403 | 9.9 |
| 190 | 386 | 9.5 |
| 191 | 382 | 9.7 |
| 192 | 366 | 9.4 |
| 193 | 393 | 9.3 |
| 194 | 362 | 9.6 |
| 195 | 370 | 9.0 |
| 196 | 362 | 9.7 |
| 197 | 370 | 9.1 |
| 198 | 397 | 9.2 |
| 199 | 366 | 9.4 |
| 200 | 370 | 9.1 |
| 201 | 413 | 9.5 |
| 202 | 370 | 9.2 |
| 203 | 382 | 9.9 |
| 204 | 382 | 9.8 |
| 205 | 392 | 8.4 |
| 206 | 403 | 10.0 |
| 207 | 412 | 8.4 |
| 208 | 413 | 9.6 |
| 209 | 400 | 8.9 |
| 210 | 364 | 8.7 |
| 211 | 395 | 8.7 |
| 212 | 364 | 8.7 |
| 213 | 395 | 8.6 |
| 214 | 409 | 9.3 |
| 215 | 418 | 9.8 |
| 216 | 378 | 9.4 |
| 217 | 378 | 9.4 |
| 218 | 409 | 9.4 |
| 219 | 423 | 8.8 |
| 220 | 366 | 8.5 |
| 221 | 398 | 9.5 |
| 222 | 408 | 8.4 |
| 223 | 378 | 8.2 |
| 224 | 364 | 7.8 |
| 225 | 394 | 7.8 |
| 226 | 378 | 8.2 |
| 227 | 394 | 9.1 |

Example 228

5-Acetyl-4-[(2,6-dimethylphenyl)amino]-2-ethyl-6-
phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 2,6-dimethylaniline following the procedure of Example 49 (5 h at room temperature, 58% yield).
m.p. 187.8-188.9° C. δ(CDCl$_3$): 1.36 (s, 3H), 1.46 (t, 3H), 2.23 (s, 6H), 4.30 (q, 2H), 7.05 (m, 3H), 7.34 (m, 5H), 7.68 (s, 1H).

Example 229

5-Acetyl-2-ethyl-4-{[4-(2-hydroxyethyl)phenyl]
amino}-6-phenylpyridazin-3(2H)-one Obtained as a solid from 5-acetyl-2-ethyl-4-nitro-6-phenylpyridazin-3(2H)-one (Dal Piaz, V et al, *J. Med. Chem.* 1997, 40, 1417) and 2-(4-aminophenyl)ethanol following the procedure of Example 49 (3.5 h at room temperature, flash column chromatography purification, 71% yield).
m.p. 145.8-146.6° C. δ(CDCl$_3$): 1.42 (t, 3H), 1.66 (s, 3H), 2.84 (m, 2H), 3.82 (m, 2H), 4.30 (q, 2H), 7.02 (d, 2H), 7.17 (d, 2H), 7.38 (m, 5H), 8.18 (s, 1H).

Example 230

5-Acetyl-2-ethyl-4-[(4-nitrophenyl)amino]-6-phe-
nylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 4-nitrophenylamine following the procedure of Example 49 (69 h at room temperature, 73% yield).
m.p. 209.8-210.7° C. δ(DMSO-d6): 1.34 (t, 3H), 2.04 (s, 3H), 4.19 (q, 2H), 7.04 (d, 2H), 7.39 (m, 2H), 7.44 (m, 3H), 8.08 (d, 2H), 9.46 (s, 1H).

Example 231

4-[(5-Acetyl-2-ethyl-3-oxo-6-phenyl-2,3-dihydropy-
ridazin-4-yl)amino]benzonitrile Obtained as a solid from 5-acetyl-2-ethyl-4-nitro-6-phenylpyridazin-3(2H)-one (Dal Piaz, V et al, *J. Med. Chem.* 1997, 40, 1417) and 4-aminobenzonitrile following the procedure of Example 49 (20 h at room temperature, 80% yield).
m.p. 204.1-204.5° C. δ(CDCl$_3$): 1.44 (t, 3H), 1.87 (s, 3H), 4.30 (q, 2H), 7.06 (d, 2H), 7.44 (mn, 5H), 7.58 (d, 2H), 8.61 (s, 1H).

Example 232

3-[(5-Acetyl-2-ethyl-3-oxo-6-phenyl-2,3-dihydropy-
ridazin-4-yl)amino]benzamide

Obtained as a solid from 5-acetyl-2-ethyl-4-nitro-6-phenylpyridazin-3(2H)-one (Dal Piaz, V et al, *J. Med. Chem.* 1997, 40, 1417) and 3-aminobenzamide following the procedure of Example 49 (1 h at room temperature, 90% yield).
m.p. 215.8-216.7° C. δ(DMSO-d6): 1.34 (t, 3H), 1.65 (s, 3H), 4.18 (q, 2H), 7.19 (d, 1H), 7.31 (m, 1H), 7.40 (m, 6H), 7.51 (s, 1H), 7.58 (d, 1H), 7.87 (s, 1H), 9.05 (s, 1H).

Example 233

5-Acetyl-2-ethyl-4-{[2-(hydroxymethyl)phenyl]
amino}-6-phenylpyridazin-3(2H)-one Obtained as a solid from 5-acetyl-2-ethyl-4-nitro-6-phenylpyridazin-3(2H)-one (Dal Piaz, V et al, *J. Med. Chem.* 1997, 40, 1417) and (2-aminophenyl)methanol following the procedure of Example 49 (1.5 h at room temperature, 48% yield).

Example 234

2-[(5-Acetyl-2-ethyl-3-oxo-6-phenyl-2,3-dihydropyridazin-4-yl)amino]benzamide

Obtained as a solid from 5-acetyl-2-ethyl-4-nitro-6-phenylpyridazin-3(2H)-one (Dal Piaz, V et al, *J. Med. Chem.* 1997, 40, 1417) and 2-aminobenzamide following the procedure of Example 49 (2 h at room temperature, 61% yield).

m.p. 185.5-186.8° C. δ(DMSO-d6): 1.33 (t, 3H), 1.79 (s, 3H), 4.17 (q, 2H), 6.88 (d, 1H), 7.03 (t, 1H), 7.26 (t, 1H), 7.35 (m, 2H), 7.44 (m, 3H), 7.63 (m, 2H), 8.14 (s, 1H), 10.08 (s, 1H).

Example 235

2-[(5-Acetyl-2-ethyl-3-oxo-6-phenyl-2,3-dihydropyridazin-4-yl)amino]benzene sulfonamide Obtained as a solid from 5-acetyl-2-ethyl-4-nitro-6-phenylpyridazin-3(2H)-one (Dal Piaz, V et al, *J. Med. Chem.* 1997, 40, 1417) and 2-aminobenzenesulfonamide following the procedure of Example 49 (96 h at room temperature, flash column chromatography purification, 35% yield).

m.p. 120.0-122.7° C. δ(DMSO-d6): 1.34 (t, 3H), 1.84 (s, 3H), 4.19 (q, 2H), 7.01 (d, 1H), 7.20 (t, 1H), 7.37 (m, 2H), 7.41 (m, 4H), 7.70 (s, 2H), 7.81 (d, 1H), 8.74 (s, 1H).

Example 236

2-[(5-Acetyl-2-ethyl-3-oxo-6-phenyl-2,3-dihydropyridazin-4-yl)amino]benzonitrile Obtained as a solid from 5-acetyl-2-ethyl-4-nitro-6-phenylpyridazin-3(2H)-one (Dal Piaz, V et al, *J. Med. Chem.* 1997, 40, 1417) and 2-aminobenzonitrile following the procedure of Example 49 (6 days at room temperature, 16% yield).

m.p. 169.7-170.2° C. δ(DMSO-d6): 1.34 (t, 3H), 1.69 (s, 3H), 4.18 (q, 2H), 7.30 (m, 4H), 7.41 (m, 3H), 7.54 (t, 1H), 7.76 (d, 1H), 9.26 (s, 1H).

Example 237

5-Acetyl-4-[(2,6-dichlorophenyl)amino]-2-ethyl-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 2,6-dichlorophenylamine following the procedure of Example 49 (6 days at 60° C., 12% yield).

m.p. 233.6-234.4° C. δ(DMSOd6): 1.33 (t, 3H), 1.55 (s, 3H), 4.17 (q, 2H), 7.31 (m, 3H), 7.41 (m, 3H), 7.48 (m, 2H), 9.03 (s, 1H).

Example 238

5-Acetyl-2-ethyl-4-[(2-nitrophenyl)amino]-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 2-nitrophenylamine following the procedure of Example 49 (4 days at 50° C., flash column chromatography purification, 50% yield).

m.p. 151.2-153.0° C. δ(DMSO-d6): 1.33 (t, 3H),1.87 (s, 3H), 4.17 (q, 2H),7.21(m, 2H), 7.40 (m, 2H), 7.47 (m, 3H), 7.58 (t, 1H), 8.07 (d, 1H), 9.46 (s, 1H).

Example 239

5-Acetyl-4-[(5-chloro-2-hydroxyphenyl)amino]-2-ethyl-6-phenylpyridazin-3(2H)-one Obtained as a solid from 5-acetyl-2-ethyl-4-nitro-6-phenylpyridazin-3(2H)-one (Dal Piaz, V et al, *J. Med. Chem.* 1997, 40, 1417) and 2-amino-4-chlorophenol following the procedure of Example 49 (2 h at room temperature, 91% yield).

m.p. 239.4-240.7° C. δ(DMSO-d6): 1.31 (t, 3H), 1.60 (s, 3H), 4.14 (q, 2H), 6.75 (m, 1H), 7.00 (m, 2H), 7.27 (m, 2H), 7.40 (m, 3H), 8.50 (s, 1H), 9.99 (s, 1H).

Example 240

5-Acetyl-4-[(3-chloro-4-hydroxyphenyl)amino]-2-ethyl-6-phenylpyridazin-3(2H)-one Obtained as a solid from 5-acetyl-2-ethyl-4-nitro-6-phenylpyridazin-3(2H)-one (Dal Piaz, V et al, *J. Med. Chem.* 1997, 40, 1417) and 4-amino-2-chlorophenol following the procedure of Example 49 (2 h at room temperature, 80% yield).

m.p. 207.1-207.6° C. δ(DMSO-d6): 1.31 (t, 3H), 1.62 (s, 3H), 4.14 (q, 2H), 6.83 (m, 2H), 7.06 (m, 1H), 7.25 (m, 2H), 7.38 (m, 3H), 8.76 (s, 1H), 10.13 (s, 1H).

Example 241

3-[(5-Acetyl-2-ethyl-3-oxo-6-phenyl-2,3-dihydropyridazin-4-yl)amino]benzenesulfonamide Obtained as a solid from 5-acetyl-2-ethyl-4-nitro-6-phenylpyridazin-3(2H)-one (Dal Piaz, V et al, *J. Med. Chem.* 1997, 40, 1417) and 3-aminobenzenesulfonamide following the procedure of Example 49 (3 h at room temperature, 87% yield).

m.p. 192.0-194.2° C. δ(DMSO-d6): 1.34 (t, 3H), 1.74 (s, 3H), 4.18 (q, 2H), 7.17 (d, 1H), 7.33 (m, 4H), 7.45 (m, 6H), 9.14 (s, 1H).

Example 242

4-[(5-Acetyl-2-ethyl-3-oxo-6-phenyl-2,3-dihydropyridazin-4-yl)amino]-1-naphthoic acid Obtained as a solid from 5-acetyl-2-ethyl-4-nitro-6-phenylpyridazin-3(2H)-one (Dal Piaz, V et al, *J. Med. Chem.* 1997, 40, 1417) and 4-aminonaphthalene-1-carboxylic acid following the procedure of Example 49 (24 h at room temperature, 54% yield).

m.p. 258.1-260.2° C. δ(DMSO-d6): 1.36 (t, 3H), 1.41 (s, 3H), 4.21 (q, 2H), 7.24 (m, 3H), 7.40 (m, 3H), 7.66 (m, 2H), 8.02 (d, 1H), 8.16 (d, 1H), 8.93 (d, 1H), 9.19 (s, 1H), 13.05 (bs, 1H).

m.p. 152.8-153.9° C. δ(DMSO-d6): 1.34 (t, 3H), 1.55 (s, 3H), 4.17 (q, 2H), 4.52 (d, 2H), 5.36 (t, 1H), 6.93 (m, 1H), 7.11 (m, 2H), 7.28 (m, 2H), 7.39 (m, 4H), 8.70 (s, 1H).

Example 243

3-[(5-Acetyl-2-ethyl-3-oxo-6-phenyl-2,3-dihydropyridazin-4-yl)amino]-4-methoxybenzamide Obtained as a solid from 5-acetyl-2-ethyl-4-nitro-6-phenylpyridazin-3(2H)one (Dal Piaz, V et al, *J. Med. Chem.* 1997, 40, 1417) and 3-amino-4-methoxybenzamide following the procedure of Example 49 (1 h at room temperature, 66% yield).

m.p. 246.1-247.5° C. δ(DMSO-d6): 1.33 (t, 3H), 1.53 (s, 3H), 3.80 (s, 3H), 4.17 (q, 2H), 7.04 (d, 1H), 7.1-7.5 (m, 6H), 7.59 (s, 1H), 7.7-7.8 (m, 2H), 8.52 (s, 1H).

Example 244

4-[(5-Acetyl-2-ethyl-3-oxo-6-phenyl-2,3-dihydropyridazin-4-yl)amino]-2-methoxybenzoic acid Obtained as a solid from 5-acetyl-2-ethyl-4-nitro-phenylpyridazin-3(2H)one (Dal Piaz, V et al, *J. Med. Chem.* 1997, 40, 1417) and 4-amino-2-methoxybenzoic acid following the procedure of Example 49 (30 h at room temperature, 83% yield).

m.p. 210.9-211.8° C. δ(DMSO-d6): 1.34 (t, 3H), 1.88 (s, 3H), 3.71 (s, 3H), 4.18 (q, 2H), 6.62 (d, 1H), 6.74 (s, 1H), 7.2-7.5 (m, 5H), 7.57 (d, 1H), 9.14 (s, 1H), 12.28 (bs, 1H).

Example 245

5-acetyl-2-ethyl-4-[(3-fluoro-4-hydroxyphenyl)amino]-6-phenylpyridazin-3(2H)-one Obtained as a solid from 5-acetyl-2-ethyl-4-nitro-6-phenylpyridazin-3(2H)-one (Dal Piaz, V et al, *J. Med. Chem.* 1997, 40, 1417) and 4-amino-2-fluorophenol following the procedure of Example 49 (1 h at room temperature, 83% yield).

m.p. 241.8-242.6° C. δ(DMSO6): 1.32 (t, 3H), 1.65 (s, 3H), 4.15 (q, 2H), 6.71 (t, 1H), 6.80 (t, 1H), 6.93 (d, 1H), 7.26 (m, 2H), 7.39 (m, 3H), 8.78 (s, 1H), 9.81 (s, 1H).

Example 246

5-acetyl-2-ethyl-4-[(5-fluoro-2-hydroxyphenyl)amino]-6-phenylpyridazin-3(2H)-one Obtained as a solid from 5-acetyl-2-ethyl-4-nitro-6-phenylpyridazin-3(2H)-one (Dal Piaz, V et al, *J. Med. Chem.* 1997, 40, 1417) and 2-amino-4-fluorophenol following the procedure of Example 49 (24 h at room temperature, 88% yield).

m.p. 190.1-190.5° C. δ(DMSO-d6): 1.19 (t, 3H), 1.49 (s, 3H), 4.02 (q, 2H), 6.6-6.8 (m, 3H), 7.0-7.4 (m, 5H), 8.36 (s, 1H), 9.56 (s, 1H).

Example 247

5-Acetyl-2-ethyl-4-[(6-hydroxy-1-naphthyl)amino]-6-phenylpyridazin-3(2H)-one

Obtained as a solid from 5-acetyl-2-ethyl-4-nitrophenylpyridazin-3(2H)-one (Dal Piaz, V et al, *J. Med. Chem.* 1997, 40, 1417) and 5-amino-2-naphthol following the procedure of Example 49 (1.5 h at room temperature, 76% yield).

m.p. 235.5-236.7° C. δ(DMSO-d6): 1.21 (s, 3H), 1.37 (t, 3H), 4.21 (q, 2H), 6.98 (d, 1H), 7.0-7.4 (m, 8H), 7.54 (d, 1H), 7.83 (d, 1H), 8.96 (s, 1H), 9.84. (s, 1H).

Example 248

5-Acetyl-2-ethyl-4-[(3-fluoro-2-methylphenyl)amino]-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 3-fluoro-2-methylaniline following the procedure of Example 49 (1 h at room temperature, 68% yield).

m.p. 189.3-190.6° C. δ(DMSO-d6):'1.35 (t, 3H), 1.46 (s, 3H), 2.11 (s, 3H), 4.18 (q, 2H), 6.89 (d, 1H), 7.0-7.2 (m, 3H), 7.2-7.5 (m, 5H), 8.74 (s, 1H).

Example 249

5-acetyl-2-ethyl-4-[(2-hydroxy-1-naphthyl)amino]-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 1-amino-2-naphthol following the procedure of Example 49 (4 h at room temperature, 52% yield).

m.p. 231.2-235.2° C. δ(DMSO-d6): 1.15 (s, 3H), 1.37 (t, 3H), 4.21 (q, 2H), 7.09 (d, 1H), 7.2-7,5 (m, 7H), 7.6-7.8 (m, 3H), 8.54 (s, 1H), 9.95 (s, 1H).

Example 250

5-Acetyl-2-ethyl-4-[(5-hydroxy-1-naphthyl)amino]-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 5-amino-1-naphthol following the procedure of Example 49 (24 h at room temperature, 24% yield).

m.p. 234.8-235.9° C. δ(DMSO-d6) 1.18 (s, 3H), 1.37 (t, 3H), 4.21 (q, 2H), 6.89 (d, 2H), 7.2-7.5 (m, 8H), 8.0 (d, 1H), 8.94 (s, 1H), 10.22 (s, 1H).

Example 251

4[(5-acetyl-2-ethyl-3-oxo-6-phenyl-2,3-dihydropyrdazin-4-yl)amino]-3-fluorobenzoic acid Obtained as a solid from 5-acetyl-2-ethyl-4-nitro-6-phenylpyridazin-3(2H)one (Dal Piaz, V et al, *J. Med. Chem.* 1997, 40, 1417) and 4-amino-3-fluorobenzenecarboxylic acid following the procedure of Example 49 (6 days at room temperature, 78% yield).

m.p. 238.1-240.9° C. δ(DMSO-d6): 1.33 (t, 3H), 1.78 (s, 3H), 4.17 (q, 2H), 7.26 (t, 1H), 7.3-7.5 (m, 5H), 7.60 (d, 1H), 7.66 (d, 1H), 9.07 (s, 1H), 13.14 (bs, 1H).

Example 252

3-[(5-Acetyl-2-ethyl-3-oxo-6-phenyl-2,3dihydropyridazin-4-yl)amino]-N,N-dimethylbenzamide Obtained as a solid from 5-acetyl-2-ethyl-4-nitro-6-phenylpyridazin-3(2H)-one (Dal Piaz, V et al, *J. Med. Chem.* 1997, 40, 1417) and 3-amino-N,N-dimethyl-benzamide following the procedure of Example 49 (24 h at room temperature, 80% yield).

m.p. 190.1-190.5° C. δ(DMSO-d6): 1.34 (t, 3H), 1.72 (s, 3H), 2.89 (s, 3H), 2.94 (s, 3H), 4.17 (q, 2H), 7.0-7.2 (m, 3H), 7.2-7.5 (m, 6H), 9.05 (s, 1H).

Example 253

3-[(5-Acetyl-2-ethyl-3-oxo-6-phenyl-2,3-dihydropyridazin-4-yl)amino]-N-methylbenzamide Obtained as a solid from 5-acetyl-2-ethyl-4-nitro-6-phenylpyridazin-3(2H)-one (Dal Piaz, V et al, *J. Med. Chem.* 1997, 40, 1417) and 3-aminobenzoylmethylamide following the procedure of Example 49 (24 h at room temperature, 74% yield).

m.p. 195.1-195.6° C. δ(DMSO-d6): 1.34 (t, 3H), 1.66 (s, 3H), 2.74 (d, 3H), 4.18 (q, 2H), 7.20 (d, 1H), 7.2-7.6 (m, 8H), 8.35 (d, 1H), 9.06 (s, 1H).

Example 254

5-Acetyl-2-ethyl-4-[(4-nitro-1-naphthyl)amino]-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 1-amino-4-nitronaphthalene following the procedure of Example 49 (2 h microwave oven, 11% yield).

m.p. 185.2-185.8° C. δ(DMSO-d6): 1.37 (t, 3H), 1.71 (s, 3H), 4.22 (q, 2H), 7.18 (m, 1H), 7.3-7.5 (m, 5H), 7.73 (t, 1H), 7.84 (t, 1H), 8.25 (d, 1H), 8.35 (d, 1H), 8.53 (d, 1H), 9.39 (s, 1H).

Example 255

4-[(5-Acetyl-2-ethyl-3-oxo-6-phenyl-2,3-dihydropyridazin-4-yl)amino]-2-fluorobenzoic acid Obtained as a solid from 5-acetyl-2-ethyl-4-nitro-6-phenylpyridazin-3(2H)-one (Dal Piaz, V et al, *J. Med. Chem.* 1997, 40, 1417) and 4-amino-2-fluorobenzoic acid following the procedure of Example 49 (20 h at room temperature, 72% yield).

m.p. 235.7-236.2° C. δ(DMSO-d6): 1.34 (t, 3H), 1.96 (s, 3H), 4.18 (q, 2H), 6.8-6.9 (m, 2H), 7.3-7.5 (m, 5H), 7.71 (t, 1H), 9.27 (s, 1H), 12.89 (s, 1H).

Example 256

4-[(5-Acetyl-2-ethyl-3-oxo-6-phenyl-2,3-dihydropyridazin-4-yl)amino]-3-chlorobenzoic acid Obtained as a solid from 5-acetyl-2-ethyl-4-nitro-6-phenylpyridazin-3(2H)-one (Dal Piaz, V et al, *J. Med. Chem.* 1997, 40, 1417) and 4-amino-3-chlorobenzoic acid following the procedure of Example 49 (15 days at room temperature, 35% yield).

m.p. 197.5-198.2° C. δ(DMSO-d6): 1.19 (t, 3H), 1.63 (s, 3H), 4.03 (q, 2H), 7.05 (d, 1H), 7.2-7.4 (m, 5H), 7.61 (dd, 1H), 7.76 (d, 1H), 8.69 (s, 1H).

Example 257

5-Acetyl 4-[(3-chloro-2-methylphenyl)amino]-2-ethyl-6-phenylpyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 3-chloro-2-methylaniline following the procedure of Example 49 (1.5 h at room temperature, 93% yield).

m.p. 219.7-220.5° C. δ(DMSO-d6): 1.35 (t, 3H), 1.45 (s, 3H), 2.24 (s, 3H), 4.18 (q, 2H), 7.07.1 (m, 2H), 7.2-7.5 (m, 6H), 8.81 (s, 1H).

Example 258

Methyl 4-[(5-acetyl-2-ethyl-3-oxo-6-phenyl-2,3-dihydropyridazin-4-yl)amino]benzoate Obtained as a solid from 5-acetyl-2-ethyl-4-nitro-6-phenylpyridazin-3(2H)-one (Dal Piaz, V et al, *J. Med. Chem.* 1997, 40, 1417) and methyl 4-aminobenzoate following the procedure of Example 49 (24 h at room temperature, 61% yield).

m.p. 177.8-179.1° C. δ(DMSO-d6): 1.34 (t, 3H), 1.86 (s, 3H), 3.80 (s, 3H), 7.07 (dd, 2H), 7.3-7.5 (m, 5H), 7.80 (dd, 2H), 9.24 (s, 1H).

Example 259

4-[(5-Acetyl-2-ethyl-3-oxo-6-phenyl-2,3-dihydropyridazin-4-yl)amino]-5-chloro-2-methoxybenzoic acid Obtained as a solid from 5-acetyl-2-ethyl-4-nitro-6-phenylpyridazin-3(2H)-one (Dal Piaz, V et al, *J. Med. Chem.* 1997, 40, 1417) and 4-amino-5-chloro-2-methoxybenzoic acid following the procedure of Example 49 (8 days at 50°, 30% yield).

δ(DMSO-d6): 1.34 (t, 3H), 1.79 (s, 3H), 3.71 (s, 3H), 4.18 (q, 2H), 6.89 (s, 1H), 7.3-7.5 (m, 5H), 7.69 (s, 1H), 8.72 (s, 1H), 12.6-12.8 (bs, 1H).

Example 260

3-[(5-Acetyl-2-ethyl-3-oxo-6-phenyl-2,3-dihydropyrdazin-4-yl)amino]-4-methylbenzamide Obtained as a solid from 5-acetyl-2-ethyl-4-nitro-6-phenylpyridazin-3(2H)-one (Dal Piaz, V et al, *J. Med. Chem.* 1997, 40, 1417) and 3-amino-4-methylbenzamide following the procedure of Example 49 (2 h at room temperature, 78% yield).

m.p. 236.1-237.9° C. δ(DMSO-d6): 1.36 (t, 3H), 1.37 (s, 3H), 2.27 (s, 3H), 4.19 (q, 2H), 7.2-7.5 (m, 7H), 7.51 (s, 1H), 7.63 (d, 1H), 7.82 (s, 1H), 8.69 (s, 1H).

Example 261

3-[(5-Acetyl-2-ethyl-3-oxo-6-phenyl-2,3-dihydropyridazin-4-yl)amino]-4-chlorobenzamide Obtained as a solid from 5-acetyl-2-ethyl-4-nitro-6-phenylpyridazin-3(2H)-one (Dal Piaz, V et al, *J. Med. Chem.* 1997, 40, 1417) and 3-amino-4-chlorobenzamide following the procedure of Example 49 (48 h at room temperature, 27% yield).

m.p. 219.2-220.1° C. δ(DMSO-d6): 1.34 (t, 3H), 1.58 (s, 3H), 4.18 (q, 2H), 7.3-7.5 (m, 5H), 7.47 (s, 1H), 7.57 (d, 1H), 7.69 (s, 1H), 7.71 (d, 1H), 7.97 (s, 1H), 8.83 (s, 1H).

Example 262

5-Acetyl-4-[(4-chloro-1-naphthyl)amino]-2-ethyl-6-phenylpyridazin-3(2H)-one

Obtained as a solid from 5-acetyl-2-ethyl-4-nitro-6-phenylpyridazin-3(2)-one (Dal Piaz, V et al, *J. Med. Chem.* 1997, 40, 1417) and 1-amino-4-chloronaphthalene following the procedure of Example 49 (4 h at room temperature, 80% yield).

m.p. 191.0-192.3° C. δ(DMSO-d6): 1.29 (s, 3H), 1.38 (t, 3H), 4.22 (q, 2H), 7.2-7.4 (m, 5H), 7.29 (s, 1H), 7.58 (d, 1H), 7.72 (m, 2H), 8.08 (d, 1H), 8.17 (d, 1H), 9.15 (s, 1H).

Example 263 LAS37729

5-Acetyl-2-ethyl-6-phenyl-4-[(2,4,6-trifluorophenyl)amino]pyridazin-3(2H)-one

Obtained as a solid from 5-acetyl-2-ethyl-4-nitro-6-phenylpyridazin-3(2H)-one (Dal Piaz, V et al, *J. Med. Chem.* 1997, 40, 1417) and 2,4,6-trifluoroaniline following the procedure of Example 49 (19 h at 500, 33% yield).

m.p. 200.2-201.0° C. δ(DMSO-d6): 1.33 (t, 3H), 1.62 (s, 3H), 4.17 (q, 2H), 7.2-7.5 (m, 7H), 8.71 (s, 1H).

Example 264

5-Acetyl-2-ethyl-6-phenyl-4-[(3,4,5-trifluorophenyl)amino]pyridazin-3(2H)-one

Obtained as a solid from 5-acetyl-2-ethyl-4-nitro-6-phenylpyridazin-3(2H)-one (Dal Piaz V et al, *J. Med. Chem.* 1997, 40, 1417) and 3,4,5-trifluoroaniline following the procedure of Example 49 (16 h at 50°, 56% yield).

m.p. 203.0-203.8° C. δ(DMSO-d6): 1.33 (t, 3H), 1.85 (s, 3H), 4.17 (q, 2H), 7.00 (dd, 2H), 7.3-7.5 (m, 5H), 9.09 (s, 1H).

Example 265

3-[(5-Acetyl-2-ethyl-3-oxo-6-phenyl-2,3-dihydropyridazin-4-yl)amino]chlorobenzoic acid To a stirred solution of 80 mg (0.28 mmol) of 5-acetyl-2-ethyl-4-nitro-6-phenylpyridazin-3(2H)-one (Dal Piaz, V et al, *J. Med. Chem.* 1997, 40, 1417) in ethanol (2 ml), 3-amino-4-chlorobenzoic acid (95 mg, 0.55 mmol) was added portionwise The resulting mixture was irradiated in microwave oven for three hours at 120° C. The final product was collected by filtration and washed with diethylether to yield the title compound (50 mg, 44% yield).

m.p. 254.6-255.9° C. δ(DMSO-d6): 1.36 (t, 3H), 1.62 (s, 3H), 4.17 (q, 2H), 7.31 (m, 2H), 7.42 (m, 3H), 7.59 (d, 1H), 7.65 (s, 1H), 7.35 (d, 1H), 8.88 (s, 1H), 13.21 (bs, 1H).

Example 266

5-Acetyl-4-{[4-(aminomethyl)phenyl]amino}-2-ethyl-6-phenylpyridazin-3(2H)-one

To a stirred solution of 100 mg (0.348 mmol) of 5-acetyl-2-ethyl-4-nitro-6-phenylpyridazin-3(2H)-one (Dal Piaz, V et al, *J. Med. Chem.* 1997, 40, 1417) in ethanol (6 ml), (4-aminobenzyl)carbamic acid tert-butyl ester (Gallo-Rodriguez, C et al *J. Med. Chem.* 1994, 37(5), 636-46) (1.16 mg, 0.52 mmol) was added portionwise. The resulting mixture was stirred at room temperature for 1 h. The precipitate thus formed was collected by filtration and washed with diethylether. Then it was solved in dichloromethane (1 mL) and trifluoroacetic acid (0.23 mL, 3.03 mmol) was added dropwise. The final mixture was stirred at room temperature for 20 minutes. Some more dichloromethane was added and this solution was washed with saturated K2CO3 solution until pH 6. The organic layer was dried and solvent removed to yield 70 mg (54% yield) of the title compound.

m.p. 138.9-139.3° C. δ(CDCl₃): 1.44 (t, 3H), 1.68 (s, 3H), 1;99 (bs, 2H), 3.87 (bs, 2H), 4.30 (q, 2H), 4.17 (q, 2H), 7.03 (d, 2H), 7.25 (d, 2H), 7.34 (m, 5H), 8.21 (s, 1H).

Example 267

5-Acetyl-4-{[4-(2-aminoethyl)phenyl]amino}-2-ethyl-6-phenylpyridazin-3(2H)-one

Obtained as a solid (84%) from 5-acetyl-2-ethyl-4-nitro-6-phenylpyridazin-3(2H)-one (Dal Piaz, V et al, *J. Med. Chem.* 1997, 40, 1417) and (2-(4-aminophenyl)-ethyl]-carbamic acid tert-butyl ester (Dannhardt, G. Et al *Archiv der Pharmazie*, 2000, 333(8), 267-74) following the procedure of Example 266.

m.p. 71.8-72.5° C. δ(CDCl₃): 1.44 (t, 3H), 1.67 (s, 3H), 1.91 (bs, 2H), 2.75 (t, 2H), 2.97 (t, 2H), 4.29 (q, 2H), 7.02 (d, 2H), 7.14 (d, 2H), 7.36 (m, 5H), 8.19 (s, 1H).

Example 268

5-Acetyl-2-ethyl-4-[(3-fluorophenyl)amino]-6-[4-(methylthio)phenyl]pyridazin-3(2H)-one Obtained as a solid (17%) from the title compound of Preparation 23 and 3-fluorophenylboronic acid following the procedure of Example 1.

m.p. 168.7-169.1° C. δ(DMSO-d6): 1.33 (t, 3H), 1.80 (s, 3H), 3.34 (s, 3H), 4.17 (q, 2H), 6.87 (m, 3H), 7.26 (m, 5H), 9.06 (s, 1H).

Example 269

1-Ethyl-5-[(3-fluorophenyl)amino]-6-oxo-3-phenyl-1,6-dihydropyridazine-4-carboxylic acid To a stirred solution of the title compound of preparation 65 (0.5 g, 1.43 mmol) in 35 mL of ethanol, ammonium formate (270 mg, 4.27 mmol) and 10% palladium on charcoal (55 mg) were added and the mixture was refluxed for 1 h. The catalyst was filtered off through a Celite pad and solvent was removed under reduced pressure to yield the title compound (0.42 g, 84% yield).

Example 270

5-[(3-Chlorophenyl)amino]-1-ethyl-6-oxo-3-phenyl-1,6-dihydropyridazine-4-carboxylic acid A mixture of the title compound of Preparation 64 (1.57 g, 6.1 mmol), 3-chlorophenylboronic acid (1.24 g, 7.9 mmol), anhydrous cupric acetate (1.66 g, 9.15 mmol), triethylamine (1.20 ml, 8.5 mmol) and activated molecular sieves (5 g, 4 Å) in dry dichloromethane (75 ml) was stirred under air exposure at room temperature overnight. The reaction mixture was filtered through a SiO₂ pad and eluted with dichloromethane. The solvent was removed under reduced pressure and the product was purified by column chromatography (SiO₂, hexane-ethylacetate). 380 mg of the final product (19% yield) were obtained.

LRMS: m/Z 370 (M+1)⁺ Retention Time: 8.3 min

Example 271

Methyl-1-ethyl-5-[(3-fluorophenyl)amino]-6-oxo-3-phenyl-1,6-dihydropyridazine-4-carboxylate To a stirred solution of the title compound of example 270 (140 mg, 0.40 mmol) in 6 mL of dry DMF, anhydrous potassium carbonate (157 mg, 0.40 mmol) was added and the mixture was stirred for a while. Finally, methyl iodide (157 mg, 1.11 mmol) was added and the final mixture was stirred at room temperature for 1 hour. Then some water was added until a solid appeared. It was collected by filtration and washed with cold water to yield the title compound (120 mg, 83% yield).

m.p. 187.4-188.3° C. $\delta$(DMSO-$d_6$): 1.34 (t, 3H), 2.92 (s, 3H), 4.17 (q, 2H), 6.92 (m, 3H), 7.34 (m, 6H), 9.25 (s, 1H).

Examples 272-273

Isopropyl 5-[(3-chlorophenyl)amino]-1-ethyl-6-oxo-3-phenyl-1,6-dihydropyridazine-4-carboxylate Ethyl 5-[(3-chlorophenyl)amino]-1-ethyl-6-oxo-3-phenyl-1,6-dihydropyridazine-4-carboxylate The title compounds were synthesized from the title compound of Example 270 and the corresponding alkylating agent following the experimental procedure of Example 271. The ESI/MS data and HPLC retention times are summarized in Table 25.

TABLE 25

| EXAMPLE | ESI/MS m/e (M + H)+ | Retention Time (min) |
|---|---|---|
| 272 | 412 | 10.4 |
| 273 | 398 | 10.1 |

Example 274

Benzyl 5-[(3-chlorophenyl)amino]-1-ethyl-6-oxo-3-phenyl-1,6-dihydropyridazine-4-carboxylate Obtained (20%) from the title product of Example 270 and benzyl bromide following the experimental procedure of Example 271.

m.p. 181.8-182.4° C. $\delta$(CDCl$_3$): 1.43 (t, 3H), 1.56 (s, 3H), 4.32 (q, 2H), 4.40 (s, 2H), 6.80 (d, 2H), 7.05 (d, 1H), 7.15-7.36 (m, 11H), 7.92 (s, 1H).

The following examples illustrate pharmaceutical compositions according to the present invention and procedure for their preparation.

Composition Example 1

Preparation of Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention are mixed with 340.8 g of lactose and 85.2 g of microcrystalline cellulose: The mixture is subjected to compression moulding using a roller compactor to give a flake-like compressed material. The flake-like compressed material is pulverised using a hammer mill, and the pulverised material is screened through a 20 mesh screen. A 4.5 g portion of light silicic anhydride and 4.5 g of magnesium stearate are added to the screened material and mixed. The mixed product is subjected to a tablet making machine equipped with a die/punch system of 7.5 mm in diameter, thereby obtaining 3,000 tablets each having 150 mg in weight.

Composition Example 2

Preparation of Coated Tablets

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidised bed granulating machine, 15 g of the compound of the present invention are mixed with 285.6 g of lactose and 122.4 g of corn starch. Separately, 22.5 g of polyvinylpyrrolidone is dissolved in 127.5 g of water t6 prepare a binding solution. Using a fluidised bed granulating machine, the binding solution is sprayed on the above mixture to give granulates. A 4.5 g portion of magnesium stearate is added to the obtained granulates and mixed. The obtained mixture is subjected to a tablet making machine equipped with a die/punch biconcave system of 6.5 mm in diameter, thereby obtaining 3,000 tablets, each having 150 mg in weight.

Separately, a coating solution is prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above are coated with the coating solution to give film-coated tablets, each having 154.5 mg in weight.

Composition Example 3

Preparation of Capsules

Formulation:

| | |
|---|---|
| Compound of the present invention | 5.0 mg |
| Lactose monohydrate | 200 mg |

| -continued | |
|---|---|
| Colloidal silicon dioxide | 2 mg |
| Corn starch | 20 mg |
| Magnesium stearate | 4 mg |

25 g of active compound, 1 Kg of lactose monohydrate, 10 g of colloidal silicon dioxide, 100 g of corn starch and 20 g of magnesium stearate are mixed. The mixture is sieved through a 60 mesh sieve, and then filled into 5,000 gelatine capsules.

Composition Example 4

Preparation of a Cream

Formulation:

| Compound of the present invention | 1% |
|---|---|
| Cetyl alcohol | 3% |
| Stearyl alcohol | 4% |
| Glyceryl monostearate | 4% |
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:
1. A compound chosen from:
5-Acetyl-4-[(3,5-difluorophenyl)amino]-2-ethyl-6-phenylpyridazin-3(2H)-one;
5-Acetyl-4-[(3,5-dichlorophenyl)amino]-2-ethyl-6-phenylpyridazin-3(2H)-one;
5-Acetyl-2-ethyl-4-[(3-nitrophenyl)amino]-6-phenylpyridazin-3(2H)-one;
5-Acetyl-2-ethyl-4-[(2-methylphenyl)amino]-6-phenylpyridazin-3(2H)-one;
5-Acetyl-2-ethyl-4-[(2-methoxyphenyl)amino]-6-phenylpyridazin-3(2H)-one;
5-Acetyl-2-ethyl-4-(1-naphthylamino)-6-phenylpyridazin-3(2H)-one;
5-Acetyl-2-ethyl-4-{[4-(methylthio)phenyl]amino}-6-phenylpyridazin-3(2H)-one;
5-Acetyl-4-[(4-acetylphenyl)amino]-2-ethyl-6-phenylpyridazin-3(2H)-one;
5-Acetyl-4-{[4-(dimethylamino)phenyl]amino}-2-ethyl-6-phenylpyridazin-3(2H)-one;
5-Acetyl-2-ethyl-4-(2-naphthylamino)-6-phenylpyridazin-3(2H)-one;
5-Acetyl-4-[(2-chlorophenyl)amino]-2-ethyl-6-phenylpyridazin-3(2H)-one;
5-Acetyl-2-ethyl-6-phenyl-4-([3-(trifluoromethoxy)phenyl]amino)pyridazin-3(2H)-one;
5-Acetyl-2-ethyl-6-phenyl-4-([2-(trifluoromethyl)phenyl]amino)pyridazin-3(2H)-one;
5-Acetyl-2-ethyl-4-[(2,5-dimethoxyphenyl)amino]-6-phenylpyridazin-3(2H)-one;
5-Acetyl-2-ethyl-4-[(2-fluoro-3-methoxyphenyl)amino]-6-phenylpyridazin-3(2H)-one;
5-Acetyl-4-[(2,3-dichlorophenyl)amino]-2-ethyl-6-phenylpyridazin-3(2H)-one;
5-Acetyl-4-[(5-chloro-2-methoxyphenyl)amino]-2-ethyl-6-phenylpyridazin-3(2H)-one;
5-Acetyl-2-ethyl-4-[(5-fluoro-2-methoxyphenyl)amino]-6-phenylpyridazin-3(2H)-one;
Methyl 4-({5-acetyl-2-ethyl-6-[4-(methylthio)phenyl]-3-oxo-2,3-dihydropyridazin-4-yl}amino)benzoate;
5-Acetyl-2-ethyl-4-[(3-fluorophenyl)amino]-6-[4-(methylthio)phenyl]pyridazin-3(2H)-one;
4-({5-Acetyl-2-ethyl-6-[4-(methylthio)phenyl]-3-oxo-2,3-dihydropyridazin-4-yl}amino)benzoic acid;
5-Acetyl-2-ethyl-6-[4-(methylthio)phenyl]-4-(1-naphthylamino)pyridazin-3(2H)-one;
5-Butyryl-2-ethyl-4-[(3-fluorophenyl)amino]-6-[4-(methylthio)phenyl]pyridazin-3(2H)-one;
2-Ethyl-5-(2-ethylbutanoyl)-4-[(3-fluorophenyl)amino]-6-[4-(methylthio)phenyl]pyridazin-3(2H)-one;
2-Ethyl-5-(2-ethylbutanoyl)-6-[4-(methylthio)phenyl]-4-(naphth-1-ylamino)pyridazin-3(2H)-one;
Methyl 4-({5-acetyl-2-ethyl-6-[4-(methylsulphinyl)phenyl]-3-oxo-2,3-dihydropyridazin-4-yl}amino)benzoate;
5-Acetyl-2-ethyl-4-[(3-fluorophenyl)amino]-6-[4-(methylsulphinyl)phenyl]pyridazin-3(2H)-one;
5-Acetyl-4-[(3-chlorophenyl)amino]-2-ethyl-6-[4-(methylsulphinyl)phenyl]pyridazin-3(2H)-one;
5-Acetyl-2-ethyl-4-[(2-methylphenyl)amino]-6-[4-(methylsulphinyl)phenyl]pyridazin-3(2H)-one;
5-Acetyl-2-ethyl-6-[4-(methylsulphinyl)phenyl]-4-(1-naphthylamino)pyridazin-3(2H)-one;
5-Acetyl-2-ethyl-6-[4-(methylsulphinyl)phenyl]-4-[(3-nitrophenyl)amino]pyridazin-3(2H)-one;
5-Acetyl-2-ethyl-6-[4-(methylsulphinyl)phenyl]-4-[(2-methoxyphenyl)amino]pyridazin-3(2H)-one;
5-Acetyl-2-ethyl-6-[4-(methylsulphinyl)phenyl]-4-[(3-methoxyphenyl)amino]pyridazin-3(2H)-one;
5-Acetyl-6-[3-(cyclopentyloxy)-4-methoxyphenyl]-2-ethyl-4-[(3-fluorophenyl)amino]pyridazin-3(2H)-one;
5-Acetyl-6-[3-(cyclopentyloxy)-4-methoxyphenyl]-2-ethyl-4-(1-naphthylamino)pyridazin-3(2H)-one;
5-Acetyl-2-methyl-4-(1-naphthylamino)-6-phenylpyridazin-3(2H)-one;
5-Acetyl-4-[(3,5-difluorophenyl)amino]-2-methyl-6-phenylpyridazin-3(2H)-one;
5-Acetyl-4-[(3-chlorophenyl)amino]-2-methyl-6-phenylpyridazin-3(2H)-one;
5-Acetyl-2-benzyl-4-[(3,5-difluorophenyl)amino]-6-phenylpyridazin-3(2H)-one;
5-Acetyl-2-benzyl-4-[(3-fluorophenyl)amino]-6-phenylpyridazin-3(2H)-one;
5-Acetyl-2-benzyl-4-[(3-chlorophenyl)amino]-6-phenylpyridazin-3(2H)-one;
5-Acetyl-2-(cyclopropylmethyl)-4-(1-naphthylamino)-6-phenylpyridazin-3(2H)-one;
5-Acetyl-2-(cyclopropylmethyl)-4-[(3-fluorophenyl)amino]-6-phenylpyridazin-3(2H)-one;
5-Acetyl-4-[(3-chlorophenyl)amino]-2-(cyclopropylmethyl)-6-phenylpyridazin-3(2H)-one;
5-Acetyl-4-(1-naphthylamino)-6-phenyl-2-pyridin-4-ylmethylpyridazin-3(2H)-one;
5-Acetyl-4-[(3-fluorophenyl)amino]-6-phenyl-2-pyridin-4-ylmethylpyridazin-3(2H)-one;
4-[(5-Acetyl-2-ethyl-3-oxo-6-phenyl-2,3-dihydropyridazin-4-yl)amino]benzoic acid;
2-[(5-Acetyl-2-ethyl-3-oxo-6-phenyl-2,3-dihydropyridazin-4-yl)amino]benzoic acid;
5-Acetyl-4-[(3-chlorophenyl)amino]-2-ethyl-6-phenylpyridazin-3(2H)-one;

5-Acetyl-4-[(3-bromophenyl)amino]-2-ethyl-6-phenylpyridazin-3(2H)-one;
5-Acetyl-4-[(3,4-dimethoxyphenyl)amino]-2-ethyl-6-phenylpyridazin-3(2H)-one;
5-Acetyl-2-ethyl-4-{[4-(hydroxymethyl)phenyl]amino}-6-phenylpyridazin-3(2H)-one;
5-Acetyl-4-(1,1'-biphenyl-4-ylamino)-2-ethyl-6-phenylpyridazin-3(2H)-one;
5-Acetyl-2-ethyl-6-phenyl-4-(5,6,7,8-tetrahydronaphthalen-1-ylamino)pyridazin-3(2H)-one;
5-acetyl-4-{[3-(cyclopentyloxy)-4-methoxyphenyl]amino}-2-ethyl-6-phenylpyridazin-3(2H)-one;
5-Acetyl-4-(1,3-benzodioxol-5-ylamino)-2-ethyl-6-phenylpyridazin-3(2H)-one;
5-Acetyl-2-ethyl-4-[(4-methoxyphenyl)amino]-6-phenylpyridazin-3(2H)-one;
5-Acetyl-4-[(4-chlorophenyl)amino]-2-ethyl-6-phenylpyridazin-3(2H)-one;
5-Acetyl-4-[(4-bromophenyl)amino]-2-ethyl-6-phenylpyridazin-3(2H)-one;
5-Acetyl-2-ethyl-6-phenyl-4-{[3-(trifluoromethyl)phenyl]amino}pyridazin-3(2H)-one;
5-Acetyl-4-[(3-chloro-4-methoxyphenyl)amino]-2-ethyl-6-phenylpyridazin-3(2H)-one;
5-Acetyl-2-ethyl-4-[(3-hydroxyphenyl)amino]-6-phenylpyridazin-3(2H)-one;
3-[(5-Acetyl-2-ethyl-3-oxo-6-phenyl-2,3-dihydropyridazin-4-yl)amino]benzoic acid;
5-Acetyl-2-ethyl-4-[(2-fluorophenyl)amino]-6-phenylpyridazin-3(2H)-one;
4-(5-Acetyl-2-ethyl-3-oxo-6-phenyl-2,3-dihydro-pyridazin-4-ylamino)-benzoic acid ethyl ester;
5-Acetyl-2-ethyl-4-[(4-fluorophenyl)amino]-6-phenylpyridazin-3(2H)-one;
2-[(5-acetyl-2-ethyl-3-oxo-6-phenyl-2,3-dihydropyridazin-4-yl)amino]-4-fluorobenzoic acid;
3-[(5-Acetyl-2-ethyl-3-oxo-6-phenyl-2,3-dihydropyridazin-4-yl)amino]benzonitrile;
4-[(5-Acetyl-2-ethyl-3-oxo-6-phenyl-2,3-dihydropyridazin-4-yl)amino]-2-hydroxybenzoic acid;
5-Acetyl-2-ethyl-4-[(3-hydroxy-4-methoxyphenyl)amino]-6-phenylpyridazin-3(2H)-one;
4-[(5-Acetyl-2-ethyl-3-oxo-6-phenyl-2,3-dihydropyridazin-4-yl)amino]benzamide;
5-Acetyl-2-ethyl-4-{[3-(methylthio)phenyl]amino}-6-phenylpyridazin-3(2H)-one;
5-Acetyl-2-ethyl-4-[(3-methoxyphenyl)amino]-6-phenylpyridazin-3(2H)-one;
5-Acetyl-4-[(3-acetylphenyl)amino]-2-ethyl-6-phenylpyridazin-3(2H)-one;
{4-[(5-Acetyl-2-ethyl-3-oxo-6-phenyl-2,3-dihydropyridazin-4-yl)amino]phenyl}acetic acid;
5-Acetyl-4-[4-(tert-butylphenyl)amino]-2-ethyl-6-phenylpyridazin-3(2H)-one;
4-[(5-Acetyl-2-ethyl-3-oxo-6-phenyl-2,3-dihydropyridazin-4-yl)amino]benzenesulphonamide;
4-{4-[(5-Acetyl-2-ethyl-3-oxo-6-phenyl-2,3-dihydropyridazin-4-yl)amino]phenyl}-4-oxobutanoic acid;
3-[(5-Acetyl-2-ethyl-3-oxo-6-phenyl-2,3-dihydropyridazin-4-yl)amino]-N-butylbenzenesulphonamide;
5-Acetyl-2-ethyl-4-[(1-oxo-2,3-dihydro-1H-inden-5-yl)amino]-6-phenylpyridazin-3(2H)-one;
N-{4-[(5-Acetyl-2-ethyl-3-oxo-6-phenyl-2,3-dihydropyridazin-4-yl)amino]phenyl}acetamide;
4-[5-Acetyl-6-(3-chlorophenyl)-2-ethyl-3-oxo-2,3-dihydropyridazin-4-ylamino]benzoic acid;
5-Acetyl-6-(3-chlorophenyl)4-[(3-chlorophenyl)amino]-2-ethylpyridazin-3(2H)-one;
5-Acetyl-6-(3-chlorophenyl)-2-ethyl-4-[(3-fluorophenyl)amino]pyridazin-3(2H)-one;
5-Acetyl-4-[(3-chlorophenyl)amino]-2-ethyl-6-(4-fluorophenyl)pyridazin-3(2H)-one;
5-Acetyl-4-[(3-bromophenyl)amino]-2-ethyl-6-(3-fluorophenyl)pyridazin-3(2H)-one;
5-Acetyl-2-ethyl-4-[(3-fluorophenyl)amino]-6-(3-fluorophenyl)pyridazin-3(2H)-one;
5-Acetyl-4-[(3-chlorophenyl)amino]-2-ethyl-6-(3-fluorophenyl)pyridazin-3(2H)-one;
5-Acetyl-4-[(3-chlorophenyl)amino]-2-ethyl-6-(3-nitrophenyl)pyridazin-3(2H)-one;
5-Acetyl-2-ethyl-4-[(3-fluorophenyl)amino]-6-(3-nitrophenyl)pyridazin-3(2H)-one;
4-{[5-Acetyl-2-ethyl-6-(3-nitrophenyl)-3-oxo-2,3-dihydropyridazin-4-yl]amino}benzoic acid;
5-Acetyl-4-[(3-bromophenyl)amino]-2-ethyl-6-(3-nitrophenyl)pyridazin-3(2H)-one;
5-Acetyl-2-ethyl-4-(naphthalen-1-ylamino)-6-(3-nitrophenyl)pyridazin-3(2H)-one;
5-Butyryl-4-[(3-chlorophenyl)amino]-2-ethyl-6-phenylpyridazin-3(2H)-one;
5-Acetyl-4-[(3-chlorophenyl)amino]-6-phenyl-2-propylpyridazin-3(2H)-one;
5-Acetyl-2-butyl-4-[(3-chlorophenyl)amino]-6-phenylpyridazin-3(2H)-one;
5-Acetyl-4-[(3-bromophenyl)amino]-2-butyl-6-phenylpyridazin-3(2H)-one;
5-Acetyl-4-[N-(3,5-dichlorophenyl)-N-(3-fluorophenyl)amino]-2-ethyl-6-phenylpyridazin-3(2H)-one;
5-Acetyl-4-[bis(3-fluorophenyl)amino]-2-ethyl-6-phenylpyridazin-3(2H)-one;
5-Acetyl-4-[bis(3-chlorophenyl)amino]-2-ethyl-6-phenylpyridazin-3(2H)-one;
5-Acetyl-2-ethyl-4-[bis(3-methylsulphanylphenyl)amino]-6-phenylpyridazin-3(2H)-one;
5-Acetyl-4-[bis(3-acetylphenyl)amino]-2-ethyl-6-phenylpyridazin-3(2H)-one;
5-Acetyl-4-[bis-(3,5-dichlorophenyl)amino]-2-ethyl-6-phenyl-2H-pyridazin-3-one;
methyl 4-{N-(5-acetyl-2-ethyl-6-(4-methylsulphinylphenyl)-3-oxo-2,3-dihydropyridazin-4-yl)-N-[4-(methoxycarbonyl)phenyl]amino}benzoate;
5-Acetyl-2-(cyclopropylmethyl)-4-[(3,5-difluorophenyl)amino]-6-phenylpyridazin-3(2H)-one;
5-Acetyl-4-[(3-fluorophenyl)amino]-2-methyl-6-phenylpyridazin-3(2H)-one;
4-[(5-Acetyl-2-methyl-3-oxo-6-phenyl-2,3-dihydropyridazin-4-yl)amino]benzoic acids;
5-Acetyl-4-[(3,5-dichlorophenyl)amino]-2,6-diphenylpyridazin-3(2H)-one;
5-Acetyl-4-[(3-fluorophenyl)amino]-2,6-diphenylpyridazin-3(2H)-one;
5-Acetyl-4-(1-naphthylamino)-2,6-diphenylpyridazin-3(2H)-one;
5-Acetyl-4-[(3,5-difluorophenyl)amino]-2,6-diphenylpyridazin-3(2H)-one;
5-Acetyl-4-[(3-chlorophenyl)amino]-2,6-diphenylpyridazin-3(2H)-one;
5-Benzoyl-4-[(3-chlorophenyl)amino]-2-ethyl-6-methylpyridazin-3(2H)-one;
5-[(3-Chlorophenyl)amino]-1-ethyl-6-oxo-3-phenyl-1,6-dihydropyridazine-4-carbaldehyde;
Methyl 5-[(3-chlorophenyl)amino]-1-ethyl-6-oxo-3-phenyl-1,6-dihydropyridazine-4-carboxylate;

5-Acetyl-4-[(3-chlorophenyl)amino]-2-(2-hydroxyethyl)-6-phenylpyridazin-3(2H)-one;
5-Acetyl-4-[(3-chlorophenyl)amino]-2-[2-(dimethylamino)ethyl]-6-phenylpyridazin-3(2H)-one;
5-Acetyl-2-cyclobutyl-4-[(3,5-dichlorophenyl)amino]-6-phenylpyridazin-3(2H)-one;
5-Acetyl-4-[(3-chlorophenyl)(2-hydroxyethyl)amino]-2-ethyl-6-phenylpyridazin-3(2H)-one;
N-(5-Acetyl-2-ethyl-3-oxo-6-phenyl-2,3-dihydropyridazin-4-yl)-N-(3-chlorophenyl)urea;
4-[(3-Chlorophenyl)amino]-5-[(dimethylamino)acetyl]-2-ethyl-6-phenylpyridazin-3(2H)-one;
4-{[2-Ethyl-5-(methoxyacetyl)-6-phenyl-3-oxo-2,3-dihydropyridazin-4-yl]amino}benzoic acid;
5-[(3-Cyanophenyl)amino]-1-ethyl-6-oxo-3-phenyl-1,6-dihydropyridazine-4-carboxamide;
5-[(3-Cyanophenyl)amino]-1-ethyl-6-oxo-3-phenyl-1,6-dihydropyridazine-4-carboxylic acid;
3-{4-Acetyl-5-[(3,5-difluorophenyl)amino]-1-ethyl-6-oxo-1,6-dihydropyridazin-3-yl}benzoic acid;
3-{4-Acetyl-5-[(3,5-difluorophenyl)amino]-1-ethyl-6-oxo-1,6-dihydropyridazin-3-yl}benzonitrile;
N-(3-{4-Acetyl-5-[(3,5-difluorophenyl)amino]-1-ethyl-6-oxo-1,6-dihydropyridazin-3-yl}phenyl)urea; and
5-Acetyl-4-[(3-chlorophenyl)amino]-6-phenylpyridazin-3(2H)-one.

2. A compound according to claim 1, chosen from:
5-Acetyl-2-ethyl-4-[(3-fluorophenyl)amino]-6-phenylpyridazin-3(2H)-one;
5-Acetyl-4-[(3,5-difluorophenyl)amino]-2-ethyl-6-phenylpyridazin-3(2H)-one;
5-Acetyl-2-ethyl-4-(1-naphthylamino)-6-phenylpyridazin-3(2H)-one;
5-Acetyl-4-[(2-chlorophenyl)amino]-2-ethyl-6-phenylpyridazin-3(2H)-one;
4-({5-Acetyl-2-ethyl-6-[4-(methylthio)phenyl]-3-oxo-2,3-dihydropyridazin-4-yl}amino)benzoic acid;
5-Acetyl-2-ethyl-4-[(2-methylphenyl)amino]-6-[4-(methylsulphinyl)phenyl]pyridazin-3(2H)-one;
5-Acetyl-6-[3-(cyclopentyloxy)-4-methoxyphenyl]-2-ethyl-4-[(3-fluorophenyl)amino]pyridazin-3(2H)-one;
5-Acetyl-4-[(3,5-difluorophenyl)amino]-2-methyl-6-phenylpyridazin-3(2H)-one;
5-Acetyl-2-(cyclopropylmethyl)-4-[(3-fluorophenyl)amino]-6-phenylpyridazin-3(2H)-one;
5-Acetyl-4-[(3-chlorophenyl)amino]-2-(cyclopropylmethyl)-6-phenylpyridazin-3(2H)-one;
4-[(5-Acetyl-2-ethyl-3-oxo-6-phenyl-2,3-dihydropyridazin-4-yl)amino]benzoic acids;
5-Acetyl-4-[(3-chlorophenyl)amino]-2-ethyl-6-phenylpyridazin-3(2H)-one;
3-[(5-Acetyl-2-ethyl-3-oxo-6-phenyl-2,3-dihydropyridazin-4-yl)amino]benzonitrile;
4-[5-Acetyl-6-(3-chlorophenyl)-2-ethyl-3-oxo-2,3-dihydropyridazin-4-ylamino]benzoic acid;
5-Acetyl-6-(3-chlorophenyl)-2-ethyl-4-[(3-fluorophenyl)amino]pyridazin-3(2H)-one;
5-Acetyl-2-ethyl-4-[(3-fluorophenyl)amino]-6-(3-fluorophenyl)pyridazin-3(2H)-one;
5-Acetyl-4-[(3-chlorophenyl)amino]-2-ethyl-6-(3-fluorophenyl)pyridazin-3(2H)-one;
5-Acetyl-2-ethyl-4-(naphthalen-1-ylamino)-6-(3-nitrophenyl)pyridazin-3(2H)-one; and
5-Acetyl-2-(cyclopropylmethyl)-4-[(3,5-difluorophenyl)amino]-6-phenylpyridazin-3(2H)-one.

3. A process for preparing a compound of formula I

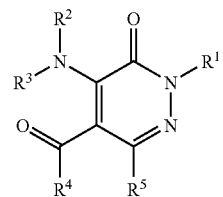

(I)

or a pharmaceutically acceptable salt thereof
wherein
$R^1$ represents:
a hydrogen atom;
a group chosen from acyl, alkoxycarbonyl, carbamoyl, monoalkylcarbamoyl and dialkylcarbamoyl;
an alkyl group, which is optionally substituted by one or more substituents chosen from halogen atoms, and hydroxy, alkoxy, aryloxy, alkylthio, oxo, amino, mono- and di-alkylamino, acylamino, carbamoyl and mono- and di-alkylcarbamoyl groups; or
a group of formula

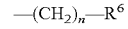

wherein n is an integer from 0 to 4 and wherein
$R^6$ represents:
a cycloalkyl group;
an aryl group, which is optionally substituted by one or more substituents chosen from halogen atoms, and alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups; or
a 3- to 7-membered ring comprising 1 to 4 heteroatoms chosen from nitrogen, oxygen and sulphur, wherein the 3- to 7-membered ring is optionally substituted by one or more substituents chosen from halogen atoms, and alkyl, hydroxy, alkoxy, alkylenedioxy, amino, mono- and di-alkylamino, nitro, cyano and trifluoromethyl groups;
$R^2$ is H;
$R^5$ represents a monocyclic or bicyclic aryl group, wherein the monocyclic or bicyclic aryl group is optionally substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
$R^3$ represents a monocyclic or bicyclic aryl group, wherein the monocyclic aryl group is substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
wherein the bicyclic aryl group is optionally substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N-alkylureido, N',N'-dialkylureido, alkylsulphamido, aminosuphonyl, mono- and di-alkylaminosulphonyl, cyano, difluoromethoxy and trifluoromethoxy groups;

$R^4$ represents:
a hydrogen atom;
a hydroxy, alkoxy, amino, mono- or di-alkylamino group;
an alkyl group, which is optionally substituted by one or more substituents chosen from halogen atoms, and hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups;: or
a group of formula —(CH$_2$)$_n$—R$^6$ with the proviso that when simultaneously $R^2$ is H, and $R^3$ and $R^5$ are unsubstituted phenyl, $R^1$ is not methyl;
comprising
reacting the corresponding 4-aminopyridazin-3(2H)-one derivative of formula (II)

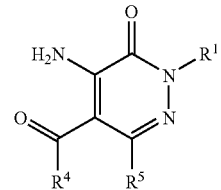

(II)

with the corresponding boronic acid of formula (IIIa)

$R^3$—B(OH)2         (IIIa);

and
optionally converting the compound of formula (I) into a pharmaceutically acceptable salt.

4. A process for preparing a compound of formula I

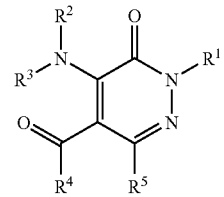

(I)

or a pharmaceutically acceptable salt thereof
wherein
$R^1$ represents:
a hydrogen atom;
a group chosen from acyl, alkoxycarbonyl, carbamoyl, monoalkylcarbamoyl and dialkylcarbamoyl;
an alkyl group, which is optionally substituted by one or more substituents chosen from halogen atoms, and hydroxy, alkoxy, aryloxy, alkylthio, oxo, amino, mono- and di-alkylamino, acylamino, carbamoyl and mono- and di-alkylcarbamoyl groups; or
a group of formula —(CH$_2$)$_n$—R$^6$ wherein n is an integer from 0 to 4 and wherein
$R^6$ represents:
a cycloalkyl group;
an aryl group, which is optionally substituted by one or more substituents chosen from halogen atoms, and alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups; or
a 3- to 7-membered ring comprising 1 to 4 heteroatoms chosen from nitrogen, oxygen and sulphur, wherein the 3- to 7-membered ring is optionally substituted by one or more substituents chosen from halogen atoms, and alkyl, hydroxy, alkoxy, alkylenedioxy, amino, mono- and di-alkylamino, nitro, cyano and trifluoromethyl groups;
$R^2$ is aryl or substituted aryl;
$R^5$ represents a monocyclic or bicyclic aryl group, wherein the monocyclic or bicyclic aryl group is optionally substituted by one or more substituents chosen from:
halogen atoms;

alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkoxycarbonyl, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
$R^3$ represents a monocyclic or bicyclic awl group,
wherein the monocyclic awl group is substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
wherein the bicyclic aryl group is optionally substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
$R^4$ represents:
a hydrogen atom;
a hydroxy, alkoxy, amino, mono- or di-alkylamino group;
an alkyl group, which is optionally substituted by one or more substituents chosen from halogen atoms, and hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; or a group of formula —$(CH_2)_n$—$R^6$ with the proviso that when simultaneously $R^2$ is H, and $R^3$ and $R^5$ are unsubstituted phenyl, $R^1$ is not methyl;
comprising
reacting the corresponding 4-aminopyridazin-3(2H)-one derivative of formula (IV):

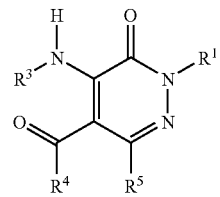

(IV)

with the corresponding boronic acid of formula (IIIb)

$R^2$—$B(OH)_2$ (IIIb)

and
optionally converting the compound of formula (I) into a pharmaceutically acceptable salt.

5. A process for preparing a compound of formula I

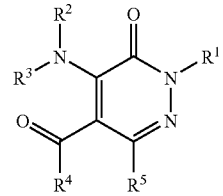

(I)

or a pharmaceutically acceptable salt thereof
wherein
$R^1$ represents:
a hydrogen atom;
a group chosen from acyl, alkoxycarbonyl, carbamoyl, monoalkylcarbamoyl and dialkylcarbamoyl;
an alkyl group, which is optionally substituted by one or more substituents chosen from halogen atoms, and hydroxy, alkoxy, aryloxy, alkylthio, oxo, amino, mono- and di-alkylamino, acylamino, carbamoyl and mono- and di-alkylcarbamoyl groups; or
a group of formula —$(CH_2)_n$—$R^6$ wherein n is an integer from 0 to 4 and wherein
$R^6$ represents:
a cycloalkyl group;
an aryl group, which is optionally substituted by one or more substituents chosen from halogen atoms, and alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups; or
a 3- to 7-membered ring comprising 1 to 4 heteroatoms chosen from nitrogen, oxygen and sulphur, wherein the 3- to 7-membered ring is optionally substituted by one or more substituents chosen from halogen atoms, and alkyl, hydroxy, alkoxy, alkylenedioxy, amino, mono- and di-alkylamino, nitro, cyano and trifluoromethyl groups;

$R^2$ represents a substituent chosen from $R^1$ and an alkyl group, wherein the alkyl group is substituted by a hydroxycarbonyl or an alkoxycarbonyl group;

$R^5$ represents a monocyclic or bicyclic aryl group, wherein the monocyclic or bicyclic aryl group is optionally substituted by one or more substituents chosen from:

halogen atoms;

alkyl and alkylene groups, wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;

$R^3$ represents a monocyclic or bicyclic aryl group, wherein the monocyclic aryl group is substituted by one or more substituents chosen from:

halogen atoms;

alkyl and alkylene groups, wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;

wherein the bicyclic aryl group is optionally substituted by one or more substituents chosen from:

halogen atoms;

alkyl and alkylene groups, wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;

$R^4$ represents:

a hydrogen atom;

a hydroxy, alkoxy, amino, mono- or di-alkylamino group;

an alkyl group, which is optionally substituted by one or more substituents chosen from halogen atoms, and hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; or a group of formula —(CH$_2$)$_n$—R$^6$ with the proviso that when simultaneously $R^2$ is H, and $R^3$ and $R^5$ are unsubstituted phenyl, $R^1$ is not methyl;

comprising reacting the corresponding 4-nitropyridazin-3(2H)-one derivative of formula (V):

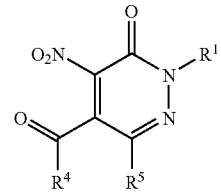

(V)

with the corresponding amine of formula (VI)

(VI)

and optionally converting the compound of formula (I) into a pharmaceutically acceptable salt.

6. A pharmaceutical composition comprising a compound as claimed in claim 1 and at least one pharmaceutically acceptable carrier or diluent.

7. A method for treating asthma in a subject in need thereof, comprising administering to said subject an effective amount of a compound of formula (I):

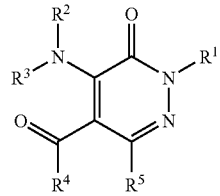

(I)

wherein $R^1$ represents:

a hydrogen atom;

a group chosen from acyl, alkoxycarbonyl, carbamoyl, monoalkylcarbamoyl and dialkylcarbamoyl:

an alkyl group, which is optionally substituted by one or more substituents chosen from halogen atoms, and hydroxy, alkoxy, aryloxy, alkylthio, oxo, amino, mono- and di-alkylamino, acylamino, carbamoyl and mono- and di-alkylcarbamoyl groups; or
a group of formula —(CH$_2$)$_n$—R$^6$ wherein n is an integer from 0 to 4 and wherein
R$^6$ represents:
 a cycloalkyl group;
 an aryl group, which is optionally substituted by one or more substituents chosen from halogen atoms, and alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups; or
 a 3- to 7-membered ring comprising 1 to 4 heteroatoms chosen from nitrogen, oxygen and sulphur, wherein the 3- to 7-membered ring is optionally substituted by one or more substituents chosen from halogen atoms, and alkyl, hydroxy, alkoxy, alkylenedioxy, amino, mono- and di-alkylamino, nitro, cyano and trifluoromethyl groups;
R$^2$ represents a substituent chosen from R$^1$ and an alkyl group, wherein the alkyl group is substituted by a hydroxycarbonyl or an alkoxycarbonyl group;
R$^5$ represents a monocyclic or bicyclic aryl group, wherein the monocyclic or bicyclic aryl group is optionally substituted by one or more substituents chosen from:
 halogen atoms;
 alkyl and alkylene groups,
  wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
 phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
R$^3$ represents a monocyclic or bicyclic aryl group,
 wherein the monocyclic aryl group is substituted by one or more substituents chosen from:
  halogen atoms;
  alkyl and alkylene groups,
   wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
  phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
 wherein the bicyclic aryl group is optionally substituted by one or more substituents chosen from:
  halogen atoms;
  alkyl and alkylene groups,
   wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
  phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
R$^4$ represents:
 a hydrogen atom;
 a hydroxy, alkoxy, amino, mono- or di-alkylamino group;
 an alkyl group, which is optionally substituted by one or more substituents chosen from halogen atoms, and hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; or
 a group of formula —(CH$_2$)$_n$—R$^6$ with the proviso that when simultaneously R$^2$ is H, and R$^3$ and R$^5$ are unsubstituted phenyl, R$^1$ is not methyl;
or a pharmaceutically acceptable salt of a compound of formula (I).

8. A method for treating atopic dermatitis in a subject in need thereof, comprising administering to said subject an effective amount of a compound of formula (I):

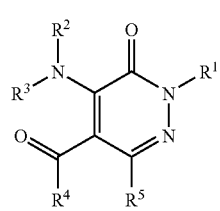

(I)

wherein
R$^1$ represents:
 a hydrogen atom;
 a group chosen from acyl, alkoxycarbonyl, carbamoyl, monoalkylcarbamoyl and dialkylcarbamoyl;
 an alkyl group, which is optionally substituted by one or more substituents chosen from halogen atoms, and hydroxy, alkoxy, aryloxy, alkylthio, oxo, amino, mono- and di-alkylamino, acylamino, carbamoyl and mono- and di-alkylcarbamoyl groups; or
 a group of formula —(CH$_2$)$_n$—R$^6$ wherein n is an integer from 0 to 4 and wherein
R$^6$ represents:
 a cycloalkyl group;

an aryl group, which is optionally substituted by one or more substituents chosen from halogen atoms, and alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups; or a 3- to 7-membered ring comprising 1 to 4 heteroatoms chosen from nitrogen, oxygen and sulphur, wherein the 3- to 7-membered ring is optionally substituted by one or more substituents chosen from halogen atoms, and alkyl, hydroxy, alkoxy, alkylenedioxy, amino, mono- and di-alkylamino, nitro, cyano and trifluoromethyl groups;

$R^2$ represents a substituent chosen from $R^1$ and an alkyl group, wherein the alkyl group is substituted by a hydroxycarbonyl or an alkoxycarbonyl group;

$R^5$ represents a monocyclic or bicyclic aryl group, wherein the monocyclic or bicyclic aryl group is optionally substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N', N'-dialkylureido, alkylsulphamido, aminosuphonyl, mono- and di-alkylaminosulphonyl, cyano, difluoromethoxy and trifluoromethoxy groups;

$R^3$ represents a monocyclic or bicyclic aryl group,
wherein the monocyclic awl group is substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and
phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;
wherein the bicyclic awl group is optionally substituted by one or more substituents chosen from:
halogen atoms;
alkyl and alkylene groups,
wherein the alkyl and alkylene groups are, each independently, optionally substituted by one or more substituents chosen from halogen atoms, and phenyl, hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; and p2 phenyl, hydroxy, alkylenedioxy, alkoxy, cycloalkyloxy, alkylthio, alkylsulphinyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulphamido, aminosuphonyl, mono- and di-alkylaminosulphonyl, cyano, difluoromethoxy and trifluoromethoxy groups;

$R^4$ represents:
a hydrogen atom;
a hydroxy, alkoxy, amino, mono- or di-alkylamino group;
an alkyl group, which is optionally substituted by one or more substituents chosen from halogen atoms, and hydroxy, alkoxy, aryloxy, alkylthio, oxo, amino, mono- and di-alkylamino, acylamino, hydroxycarbonyl, alkoxycarbonyl, carbamoyl and mono- and di-alkylcarbamoyl groups; or
a group of formula —(CH$_2$)$_n$—R$^6$ with the proviso that when simultaneously $R^2$ is H, and $R^3$ and $R^5$ are unsubstituted phenyl, $R^1$ is not methyl:
or a pharmaceutically acceptable salt of a compound of formula (I).

9. A pharmaceutical composition comprising a compound as claimed in claim 2 and at least one pharmaceutically acceptable carrier or diluent.

* * * * *

UNITED STATES PATENT AND TRADEMARK OFFICE
CERTIFICATE OF CORRECTION

PATENT NO. : 7,459,453 B2
APPLICATION NO. : 10/513219
DATED : December 2, 2008
INVENTOR(S) : Dal Piaz et al.

It is certified that error appears in the above-identified patent and that said Letters Patent is hereby corrected as shown below:

In claim 1, column 103, lines 1-2, "5-Acetyl-4-[(3-bromophenyl)amino]-2-ethyl-6-phenylpyridazin-3(2H-one;" should read --5-Acetyl-4-[(3-bromophenyl)amino]-2-ethyl-6-phenylpyridazin-3(2H)-one;--.

In claim 1, column 104, lines 1-2, "5-Acetyl-6-(3-chlorophenyl)4-[(3-chlorophenyl)amino]-2-ethylpyridazin-3(2H)-one;" should read --5-Acetyl-6-(3-chlorophenyl)-4-[(3-chlorophenyl)amino]-2-ethylpyridazin-3(2H)-one;--.

In claim 1, column 104, line 51, "acids;" should read --acid;--.

In claim 2, column 105, line 50, "acids;" should read --acid;--.

In claim 3, column 107, line 57, "groups;: or" should read --groups; or--.

In claim 4, column 109, line 17, "awl" should read --aryl--.

In claim 4, column 109, line 18, "awl" should read --aryl--.

In claim 7, column 112, line 64, "dialkylcarbamoyl:" should read --dialkylcarbamoyl;--.

In claim 8, column 115, line 40, "awl" should read --aryl--.

In claim 8, column 116, line 9, "awl" should read --aryl--.

In claim 8, column 116, line 20, after "groups; and" delete "p2" and insert a paragraph break.

UNITED STATES PATENT AND TRADEMARK OFFICE
CERTIFICATE OF CORRECTION

PATENT NO. : 7,459,453 B2
APPLICATION NO. : 10/513219
DATED : December 2, 2008
INVENTOR(S) : Dal Piaz et al.

It is certified that error appears in the above-identified patent and that said Letters Patent is hereby corrected as shown below:

In claim 8, column 116, line 44, "methyl:" should read --methyl;--.

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,459,453 B2 |
| APPLICATION NO. | : 10/513219 |
| DATED | : December 2, 2008 |
| INVENTOR(S) | : Dal Piaz et al. |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 143 days Delete the phrase "by 143 days" and insert -- by 452 days --

Signed and Sealed this

Twenty-second Day of June, 2010

David J. Kappos
*Director of the United States Patent and Trademark Office*